US012757944B2

(12) United States Patent
Cui et al.

(10) Patent No.: US 12,757,944 B2
(45) Date of Patent: Oct. 13, 2026

(54) ELECTRICAL HEATING MODULE AND POWER SUPPLY CONTROL METHOD THEREOF

(71) Applicant: SHENZHEN INNOKIN TECHNOLOGY CO., LTD., Shenzhen (CN)

(72) Inventors: Tao Cui, Shenzhen (CN); Jianwei Li, Shenzhen (CN); Zhengzhan Peng, Shenzhen (CN); Tingdong Hu, Shenzhen (CN)

(73) Assignee: SHENZHEN INNOKIN TECHNOLOGY CO., LTD., Shenzhen (CN)

( * ) Notice: Subject to any disclaimer, the term of this patent is extended or adjusted under 35 U.S.C. 154(b) by 889 days.

(21) Appl. No.: 18/154,034

(22) Filed: Jan. 12, 2023

(65) Prior Publication Data

US 2023/0148680 A1 May 18, 2023

Related U.S. Application Data

(63) Continuation of application No. PCT/CN2021/105404, filed on Jul. 9, 2021.

(30) Foreign Application Priority Data

Jul. 13, 2020 (CN) ......................... 202010667594.7
Jul. 13, 2020 (CN) ......................... 202021374624.7
(Continued)

(51) Int. Cl.
*A24F 40/57* (2020.01)
*A24F 40/10* (2020.01)
(Continued)

(52) U.S. Cl.
CPC .............. *A24F 40/57* (2020.01); *A24F 40/10* (2020.01); *H02M 3/1582* (2013.01); *H05B 1/023* (2013.01); *A61M 15/06* (2013.01)

(58) Field of Classification Search
CPC .......... A47F 40/50; A24F 40/10; A24F 40/57; H02M 7/538; H02M 3/1582; H05B 1/023;
(Continued)

(56) References Cited

U.S. PATENT DOCUMENTS

| | | | | |
|---|---|---|---|---|
| 5,814,792 A * | 9/1998 | Wildi | H05B 3/34 | 219/544 |
| 2015/0320116 A1 * | 11/2015 | Bleloch | A24F 40/44 | 219/628 |

(Continued)

FOREIGN PATENT DOCUMENTS

| | | |
|---|---|---|
| CN | 204518097 U | 7/2015 |
| CN | 109656283 A | 4/2019 |

(Continued)

OTHER PUBLICATIONS

International Search Report and Written Opinion issued Oct. 9, 2021, in PCT/CN2021/105404, and English machine translation thereof.

*Primary Examiner* — Justin C Dodson
(74) *Attorney, Agent, or Firm* — BAYES PLLC

(57) ABSTRACT

Disclosed is a personal vaping device provided with an electrical heating module as an atomizer or heater. The personal vaping device at least includes a power control circuit, which includes a current input terminal, a current input terminal, and a current control module. The power control circuit further includes a power supply control module, a current control module, a voltage modulation module, and a forward and reverse connection current generation module. The microprocessor is configured to
(Continued)

control the voltage modulation module and the forward and reverse connection current generation module. The voltage modulation module is configured to regulate a voltage of the DC power supply to a first target voltage and a second target voltage. The forward and reverse connection current generation module is configured to generate a forward connection current and a reverse connection current according to the second target voltage to drive the atomizer or heater for heating.

16 Claims, 32 Drawing Sheets

(30) Foreign Application Priority Data

| | | |
|---|---|---|
| Aug. 17, 2020 | (CN) | 202010826977.4 |
| Sep. 11, 2020 | (CN) | 202010953765.2 |
| Nov. 20, 2020 | (CN) | 202011313500.2 |
| Nov. 26, 2020 | (CN) | 202011347216.7 |
| Dec. 7, 2020 | (CN) | 202011416882.1 |
| Dec. 11, 2020 | (CN) | 202011444964.7 |
| Jan. 18, 2021 | (CN) | 202110065284.2 |
| Jan. 23, 2021 | (CN) | 202120184644.6 |

(51) Int. Cl.

| | |
|---|---|
| ***H02M 3/158*** | (2006.01) |
| ***H05B 1/02*** | (2006.01) |
| *A61M 15/06* | (2006.01) |

(58) Field of Classification Search

CPC ................ H05B 1/0269; H05B 1/0297; H05B 2203/035; A61M 15/06; A61M 11/02; A61M 2205/3368; A61M 2205/3653; A61M 2205/50; A61M 2205/8212

See application file for complete search history.

(56) References Cited

U.S. PATENT DOCUMENTS

| | | | | |
|---|---|---|---|---|
| 2020/0037664 A1* | 2/2020 | Fursa | H05B 6/105 |
| 2020/0046021 A1* | 2/2020 | Sur | H01M 50/213 |

FOREIGN PATENT DOCUMENTS

| | | | |
|---|---|---|---|
| CN | 109730360 A | 5/2019 |
| CN | 111713755 A | 9/2020 |
| CN | 112512139 A | 3/2021 |
| JP | 6639720 B1 | 2/2020 |

* cited by examiner

ELECTRICAL HEATING MODULE AND POWER SUPPLY CONTROL METHOD THEREOF

CROSS-REFERENCE TO RELATED APPLICATIONS

This application is a continuation of International Application No. PCT/CN2021/105404, filed on Jul. 9, 2021, which claims priority to Chinese Patent Application Nos. CN 202010667594.7, filed on Jul. 13, 2020, CN 202021374624.7, filed on Jul. 13, 2020, CN 202010826977.4, filed on Aug. 17, 2020, CN 202010953765.2, filed on Sep. 11, 2020, CN 202011313500.2, filed on Nov. 20, 2020, CN 202011347216.7, filed on Nov. 26, 2020, CN 202011416882.1, filed on Dec. 7, 2020, CN 202011444964.7, filed on Dec. 11, 2020, CN 202110065284.2, filed on Jan. 18, 2021, CN 202120184644.6, filed on Jan. 23, 2021. The contents of the above-referenced applications are incorporated herein by reference.

TECHNICAL FIELD

This application relates to electrical heating, and more particularly to an electrical heating module of a personal vaping device and a power supply control method thereof, and a personal vaping device having the electrical heating module.

BACKGROUND

Currently, the portable electrical resistance heating device for conversion of state of substances (hereinafter referred to as "electrical heating device") has been applied to various industries, including the medical atomization and the electronic cigarette (e-cigarette). The electrical heating device not only can heat a semi-liquid or solid substance to a liquid substance, but also can heat and atomize the liquid substance to a vapor substance.

In the portable electrical heating device, a direct-current (DC) power supply method is generally adopted for heating, where the driving method of the DC power supply circuit is extremely simple, the DC power supply voltage is usually controlled through a simple logic circuit, and the voltage output to the heating assembly of the electrical heating device is generally stable without variation in value.

In other words, the electrical heating device in the current market is normally heated by a constant-power DC, that is, the power supply circuit provides a constant voltage and a constant current to various heating assembly in the portable electrical heating device.

Under the constant voltage and current, the heating assembly, which is generally a heating wire, is heated undesirably. In this case, the portable electrical heating device cannot work in the optimal state of the heating assembly, which affects the use performance of the portable electrical heating device and shortens the service life of the heating assembly.

Moreover, such a simple power supply method has some disadvantages. For instance, during the power-on process of the electrical heating device, the temperature of the heating assembly is continuously and rapidly increased, and the heating assembly is continuously at a high temperature, which tends to cause local carbon deposition in the heating assembly and thus shorten its service life.

For example, in a traditional personal vaping device, the electrical heating module is generally heated by adopting a DC with a constant instantaneous value such that the direction of the current is fixed, and the instantaneous value of the current is also constant. Referring to FIG. 1, the current I flows from M of the heating wire to N of the heating wire to refine the M-N segment of the heating wire. The electrical heating module per se can be regarded as a resistor. The current I is first heated in the direction close to M, that is, along the direction of the current I, and at the same time, the current I generates an electrical field E. To be specific, the M-M1 segment of the heating wire is heated first, then the current flows to the N point, the M1-M2 segment, the M3-M4 segment, . . . , and the N point of the heating wire are heated in sequence, that is, the heating wire is electrified to generate heat in a sequence of M-M1 segment, M1-M2 segment, M2-M3 segment, M3-M4 segment, . . . , and the N point. In this way, the highest temperature of the heating wire is near the M point, that is, the temperature of the heating wire is gradually decreased along the M-N direction, and the temperature distribution on the heating wire is not uniform.

Moreover, if the heating assembly (i.e., heating wire) is used for a long time, foreign substances (i.e., carbides) will be produced. The current of the heating wire always flows from M to N, therefore, the direction of the electrical field in the heating wire is always from M to N. Once the surface of the heating wire generates foreign substances (i.e., carbides), parts of the foreign substances have electrical charges due to the existence of the fixed-directional electrical field such that foreign substances will be adsorbed on the surface of the heating wire and are always in a backlog and accumulated state, thereby damaging to the heating wire.

As a typical portable electrical heating device and a personal vaping device, the e-cigarette is deeply popular among most smokers. The e-cigarette mainly includes the e-cigarette atomizing e-cigarette oil or tobacco paste and the e-cigarette baking non-combustible tobacco at a low temperature. The e-cigarette atomizing e-cigarette oil, commonly known as the e-cigarette, adopts an atomizer to atomize the e-cigarette oil or the tobacco paste, which includes an atomizer, an oil storage bin, a mouthpiece, a power supply, a circuit board, and a power connection circuit board. The circuit board is connected to the atomizer. The atomizer includes an oil guide cotton and a heating wire wound around the oil guide cotton. The power supply provides electric energy to the heating wire. The oil guide cotton is used for adsorbing e-cigarette oil in the oil storage bin. The heating wire is used for atomizing the e-cigarette oil adsorbed by the oil guide cotton to create smoke, and the smoke is then vaped by users through the mouthpiece.

When the personal vaping device is the e-cigarette atomizing e-cigarette oil, the electrical heating module is an atomizer. Since the current is constant, the heat of individual regions of the atomizer cannot be flexibly adjusted such that the region at an over-high temperature cannot be effectively cooled. In this way, after a long-time use, the oil guide cotton near the M point is burnt and damaged, while at the moment, the oil guide cotton near the N point may be still in a good state. The local damage to the atomizer leads to the scrapping of the atomizer, thereby shortening the service life of the atomizer. At the same time, deposits generated by the partial insufficient atomization of the e-cigarette oil or the partial coking of the oil guide/storage medium (i.e., cotton fiber) have a severe influence on the user experience, which is described below.

A lot of the deposits may bring some bad effects. In the first aspect, small particles of the deposits fill the gap of the oil guide medium to hinder the delivery of the e-cigarette oil such that the e-cigarette oil cannot be atomized sufficiently, resulting in a bad vaping experience and a direct blockage of the vaping device. In the second aspect, the deposits may suffer secondary evaporation at a high temperature, which may contain unpredictable substances harmful to health. In the third aspect, the atomization of the e-cigarette oil is limited, which may shorten the service life of the atomizer and thus forms unnecessary waste.

The e-cigarette industry not only contains the traditional e-cigarette that burns and atomizes e-cigarette oil, but also includes the e-cigarette that bakes non-combustible tobacco at a low temperature. When the personal vaping device is the e-cigarette that bakes non-combustible tobacco at a low temperature, the electrical heating module is a low-temperature baking device, and the working substance can be a medicine, a tobacco paste, e-cigarette oil, non-combustible tobacco, and an herb. The e-cigarette that bakes non-combustible tobacco at a low temperature also adopts a low-voltage DC power supply for heating, and the direction of the current is also fixed. After being used for a long time, the surface of the electrical heating module can generate deposits that are difficult to remove and pose a severe influence on the user experience.

At present, a portable personal vaping device (i.e., e-cigarette) is generally provided with an integrated power supply circuit, where the electronic components are separately packaged on the circuit board. However, as the function of the small electronic terminal using the power supply circuit is diversified, the requirements of components are continuously increased such that the space occupied by the electronic components in the small electronic terminal becomes larger and larger, leading to an increased production cost, thereby lowering the practicability of the integrated power supply circuit and the electronic terminal using the power supply circuit.

SUMMARY OF THE DISCLOSURE

To overcome the deficiencies in the prior art, this disclosure provides a power supply control method for an electrical heating module of a personal vaping device, which can prolong the service life of the electrical heating device, balance the heating temperature in the electrical heating device, avoid the carbon deposition in the electrical heating device, improve the taste of the personal vaping device, and reduce the electric energy consumed by the electrical heating module. Moreover, it can also prolong the service life of the electrical heating device provided with the heating assembly, improve the use performance of the electrical heating module, avoid pollution due to the deposit accumulation in the heating module of the existing electronic cigarette, and raise the user experience.

This application also provides a power supply control circuit using the power supply control method, an electrical heating module provided with the power supply control circuit, and an electronic cigarette (e-cigarette) or a personal vaping device provided with the electrical heating module.

In a first aspect, this application provides a power supply control method for an electrical heating module including a personal vaping device. The power supply control method includes: providing a direct current (DC) power supply; converting a DC output from the DC power supply into a supply current having a periodic variation in at least one of direction, instantaneous value, and on-state time; and applying the supply current to the electrical heating module.

In some embodiments, the conversion of the DC includes: controlling the periodic variation of the supply current at a frequency not higher than 1000 Hz, preferably 300-1000 Hz in a cleaning state; or preferably 20-50 Hz or 80-150 Hz in a vaping state.

In some embodiments, the supply current is controlled by a plurality of preset parameters.

In some embodiments, the plurality of preset parameters include: a first parameter for controlling a variation range of the instantaneous value of the supply current; a second parameter for controlling direction variation of the supply current; a third parameter for controlling a duty ratio of the supply current; and a fourth parameter for controlling a variation frequency of the supply current.

In some embodiments, in a duty cycle, the variation range of the instantaneous value of the supply current is not less than 50%, preferably not less than 100%.

In some embodiments, the supply current has different instantaneous value during a duty cycle.

In some embodiments, the supply current is continuously maintained in the on-state.

In some embodiments, during a duty cycle, the on-state time of the supply current varies.

In some embodiments, a direction of the supply current is reversed at least once within a duty cycle.

In some embodiments, the supply current is a pulsating DC.

In some embodiments, an output energy of the supply current is maintained at a preset constant level during each duty cycle.

In some embodiments, the power supply control method further includes: providing the electrical heating module, wherein the electrical heating module has a first terminal and a second terminal; wherein in a duty cycle, a total energy provided by an electrical field to the electrical heating module is Q; the duty cycle is composed of a first time interval and a second time interval; during the first time interval, a first current $I_1$ flows from the first end to the second end, and a first energy value generated by the first current $I_1$ passing through the electrical heating module is $\alpha$*Q; during the second time interval, a second current $I_2$ flows from the second end to the first end; a second energy value generated by the second current $I_2$ passing through the electrical heating module is $\beta$*Q; and the total energy Q meets the following formulas:

$$Q=\alpha*Q+\beta*Q \quad (1);\text{ and}$$

$$\alpha+\beta=1 \quad (2);$$

wherein $\alpha$ represents an energy coefficient of the first current $I_1$ generating energy values through the electric heating module; and $\beta$ represents an energy coefficient of the second current $I_2$ generating energy values through the electric heating module.

In some embodiments, the first current is not equal to the second current; and/or the first time interval is not equal to the second time interval.

In some embodiments, the power supply control method further includes: providing the electrical heating module, wherein the electrical heating module has a first end and a second end; and applying an alternating current (AC) to the electrical heating module, wherein a direction of the AC is reversed at least once during a duty cycle.

In some embodiments, a voltage U of the AC meets the following formula:

$$U=U_m*\mathrm{Sin}(\omega t+\mu);$$

wherein $U_m$ represents a peak value of the AC; ω represents an angular frequency of the AC; μ represents an initial phase; t represents time; and the duty cycle meets: T=2π/ω, wherein T represents a duration of the duty cycle.

In some embodiments, a voltage U of the AC conforms to a triangular wave curve, as shown in the following formula:

$$U=kt+b;$$

wherein k is a slope of the triangular wave curve; b is a constant; and t represents time.

In some embodiments, the duty cycle of the AC includes at least three duty sub-time intervals; and a voltage in at least one of the at least three duty sub-time intervals is a constant or a variable value.

In some embodiments, the power supply control method further includes: regulating a voltage of the DC power supply to a first target voltage and a second target voltage; generating a forward connection current and a reverse connection current according to the second target voltage; and applying the forward connection current and the reverse connection current to the electrical heating module at different time interval within a same duty cycle of the second target voltage.

In some embodiments, the forward connection current and the reverse connection current are generated by different switch control modules. In some embodiments, a working duration of the AC is less than or equal to a time interval threshold.

In some embodiments, the step of "applying an alternating current (AC) to the electrical heating module" includes: detecting a heating current in the electrical heating module; determining a heating end time of the electrical heating module according to the heating current; and if heating of the electrical heating module is finished, driving the electrical heating module to generate physical oscillation.

In some embodiments, the step of "driving the electrical heating module to generate physical oscillation" includes: acquiring a heating parameter of the electrical heating module; and determining a generation time of the physical oscillation and a waveform of the physical oscillation according to the heating parameter, wherein the heating parameter includes heating time, heating current waveform and heating voltage.

In some embodiments, the power supply control method further includes: presetting a control command; storing the control command; reading the control command; and according to the control command, converting the DC into the supply current having the periodic variation in at least one of the direction, instantaneous value, and on-state time.

In a second aspect, this application provides a power supply control circuit for an electrical heating module of a personal vaping device. The power supply control circuit includes: a current input terminal configured to be connected to a DC power supply; a current output terminal separated from the current input terminal and configured to be connected to the electrical heating module; and a power supply control module arranged between the current input terminal and the current output terminal; wherein the power supply control module is configured to control connection and disconnection of current output, and to convert a DC into a supply current having a periodic variation in at least one of direction, instantaneous value and on-state time.

In some embodiments, conversion of the DC includes: controlling the periodic variation of the supply current at a frequency not higher than 1000 Hz, preferably 300-1000 Hz in a cleaning state; or preferably 2-200 Hz in a vaping state, and more preferably 80-150 Hz in the vaping state; or 2-100 Hz in the vaping state, and more preferably 20-50 Hz in the vaping state.

In some embodiments, the power supply control module includes: a voltage modulation module; and a microprocessor configured to provide an actuation signal to the voltage modulation module.

In some embodiments, the microprocessor is configured to output the actuation signal according to a plurality of preset parameters.

In some embodiments, the plurality of preset parameters include a variation range of the current instantaneous value and a frequency of the current variation.

In some embodiments, the voltage modulation module is configured to convert the DC flowing from the current input terminal into the supply current by modulating the actuation signal, and to establish a circuit to connect the electrical heating module through the current output terminal.

In some embodiments, the voltage modulation module includes a power conversion circuit; wherein the power conversion circuit is configured to modulate a voltage of the DC power supply according to a modulation signal sent by the microprocessor, and to output a boost voltage, a buck voltage or a pass-through voltage according to the modulation signal.

In some embodiments, the power conversion circuit includes a boost control circuit and a buck circuit; the boost control circuit is configured to modulate the voltage of the DC power supply to obtain a first target voltage and a first target current according to a first preset parameter set sent by the microprocessor in a first time range, wherein the first target voltage is higher than the voltage of the DC power supply; and the buck circuit is configured to modulate the first target voltage to obtain a second target voltage and a second target current according to a second preset parameter set sent by the microprocessor in a second time range, wherein the second target voltage is lower than the first target voltage.

In some embodiments, the power conversion circuit further includes a pass-through voltage circuit.

In some embodiments, the power conversion circuit is a combined circuit, which is designed to be switched into a boost control circuit in one time interval and switched to a buck circuit in another time interval; or the power conversion circuit includes a boost control circuit and a buck circuit independent of each other.

In some embodiments, a peak current magnitude of the DC varies in a duty cycle.

In some embodiments, in a duty cycle, the on-state time of the supply current varies.

In some embodiments, the power supply control module is configured to maintain the supply current on state.

In some embodiments, the power supply control module is configured to reverse a direction of the supply current at least once in a duty cycle to form an AC.

In some embodiments, a working duration of the AC is less than or equal to a time interval threshold.

In some embodiments, the power supply control module is configured to maintain an output energy of the supply current at a preset constant level during each duty cycle.

In some embodiments, the power supply control module further includes: a forward and reverse connection current generation module; wherein the microprocessor is configured to control the voltage modulation module and the forward and reverse connection current generation module; the voltage modulation module is configured to regulate a voltage of the DC power supply to a first target voltage and a second target voltage, and couple the second target voltage to the forward and reverse connection current generation module, wherein the first target voltage is configured to control on and off of the forward and reverse connection current generation module; and the forward and reverse connection current generation module is configured to generate a forward connection current and a reverse connection current according to the second target voltage, and couple the forward connection current and the reverse connection current to the electrical heating module at different time intervals within the same signal time interval of the second target voltage.

In some embodiments, the forward and reverse connection current generation module includes a first switch control module and a second switch control module; the first switch control module is configured to be switched on in a first time interval, generate the forward connection current according to the second target voltage, and couple the forward connection current to the electrical heating module, wherein the first time interval is a first duration of the second target voltage preset in the same voltage signal time interval; and the second switch control module is configured to be switched on in a second time interval, generate the reverse connection current according to the second target voltage, and couple the reverse connection current to the electrical heating module, wherein the second time interval is a second duration of the second target voltage preset in the same voltage signal time interval, and a sum of the first time interval and the second time interval is not larger than a duration threshold of the same voltage signal time interval.

In some embodiments, in the power supply control circuit, the microprocessor, the voltage modulation module, a driving module, and the forward and reverse connection current generation module are respectively integrated and packaged on a circuit board.

In some embodiments, the packaging is performed by in-line packaging or surface mount packaging; the in-line packaging includes single in-line packaging, single in-curve packaging, dual in-line packaging, and ball grid array packaging; and a packaging material is made of a metal, a plastic, or ceramic.

In some embodiments, the power supply control circuit further includes: a memory configured to store an instruction for controlling conversion of the DC into the supply current; wherein the microprocessor is configured to read the instruction stored by the memory to control the conversion of the DC into the supply current having periodic variations in at least one of direction, instantaneous value and on-state time.

In a third aspect, this application provides an electrical heating module for a personal vaping device, comprising: an electrical heating module; and the power supply control circuit configured to supply power to the electrical heating module.

In a fourth aspect, this application provides a portable personal vaping device, including: the electrical heating module; wherein the electrical heating module is an atomizer configured to atomize electronic cigarette (e-cigarette) oil.

In a fifth aspect, this application provides a portable personal vaping device, comprising: the electrical heating module; wherein the electrical heating module is a heater configured to heat a non-combustible tobacco.

In a sixth aspect, this application provides a portable personal vaping device, comprising: the electrical heating module; wherein the electrical heating module is a heater configured for personal physical therapy.

In some embodiments, the portable personal vaping device further includes: a DC power supply.

BRIEF DESCRIPTION OF THE DRAWINGS

The present disclosure will be further described with reference to the accompanying drawings and embodiments. It should be noted that the embodiments shown in the drawings are merely illustrative, and are not intended to limit the disclosure. Individual elements and element combinations illustrated in the following description and accompanying drawings may be arranged and organized differently to produce other embodiments that are still within the scope of the present disclosure.

The same reference numerals indicate the same parts throughout the drawings.

DETAILED DESCRIPTION

Figure 1:
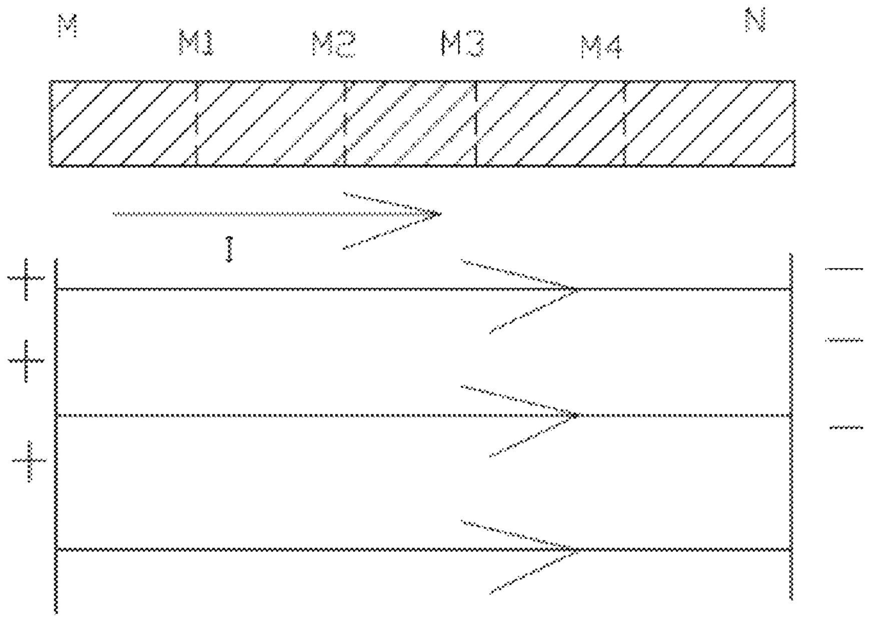
Fig. 1 (Prior Art)
FIG. 1 schematically illustrates an electrical field distribution of an electrical heating module according to conventional technologies.

Although this application may be susceptible to embodiments shown in the drawings in different forms, these embodiments will be described in detail below, and the following description should be regarded as an example of the principle of this application. The present disclosure is not limited to the details of structures, functions, and details of structures or components described in the following description or illustrated in the drawings. The present disclosure can be implemented in a variety of ways. In addition, the phraseology and terminology used herein are for description and should not be construed as limitations to the present disclosure. The use of various phrases and terms is to include the identified items or functions and equivalents thereof, as well as other items or functions. Unless otherwise limited, various phrases, terms, and variations thereof in the present disclosure are widely used and include all variants of such phrases and terms. Moreover, as described below, the specific configurations shown in the drawings are intended to illustrate embodiments of the present disclosure. Other alternative structures, functions, and configurations may be considered under the teachings of this application. Furthermore, unless stated otherwise, the term "or" should be considered as "include."

This application provides a power supply control method for an electrical heating module of a personal vaping device and a power supply control circuit using the same. The direct current (DC) is converted into a supply current having a periodical variation in at least one of direction, instantaneous value, and on-state time. In this way, the rapid ascent of the temperature of the electrical heating module is suppressed, so that the electrical heating module can be heated uniformly, thereby prolonging the service life of the electrical heating module and improving the use performance of the electrical heating module.

In this application, the personal vaping device is defined as a portable electronic device for personal vaping, including, but not limited to, tobacco and products thereof, *cannabis* and products thereof, e-cigarette oil and products thereof, tobacco paste and products thereof, non-combustible tobacco and products thereof, and solid or liquid products for medical or physiotherapy purposes. The electrical heating module is defined as an energy conversion device to directly generate Joule heat by the current passing through the conductor for heating. The DC power supply is defined as a device for maintaining a constant-voltage current formed in the circuit, including, but not limited to, a dry battery, a storage battery, a DC generator, and a DC voltage-stabilized power supply. The current input terminal is defined as a point where the power supply control circuit is connected to the DC power supply, where the point should be understood as a term describing the relationship among individual components of the circuit rather than a certain point in the spatial or physical significance, and may correspond to a single or multiple points in spatial or physical significance. The current output terminal is defined as a point where the power supply control circuit is connected to the electrical heating module, where the point should be understood as a term describing the relationship among individual components of the circuit rather than a certain point in the spatial or physical significance, and may correspond to a single or multiple points in spatial or physical significance. The microprocessor is defined as a logic circuit having functions (such as recording, storing, reading, and executing). The microprocessor can be a programmable special circuit (i.e., an integrated circuit), and can also be a processor in which all the elements are miniaturized into one or a plurality of integrated circuits to store and execute a control instruction, so as to output a control signal to the peripheral circuit. The packaging is a process for assembling a logic circuit into a final product of a microprocessor, the produced integrated circuit die is placed on a substrate that serves as a bearing to be fixedly packaged into a whole with the pins being led out.

In the present disclosure, the direction of the current is defined as a direction from a high potential to a low potential in a circuit. The instantaneous value is defined as a value of voltage or current at each moment and can be described as a function of time. If the positive direction of the current or voltage is specific, the value of the current or voltage is positive in the positive direction and negative in the negative direction. The on-state time is defined as the time interval in which the instantaneous value of the current output terminal is not zero, that is, the time interval where the current passes through the current output terminal. The current phase is defined as the position where the specific current instantaneous value is in the current instantaneous value periodic cycle. The set of preset parameters is defined as a series of control instructions pre-stored in the microprocessor, where the control instruction includes information on the power supply current applied to the electrical heating module (i.e., instantaneous value, direction, on-state time, and frequency), and acts on circuit modules other than the microprocessor. The alternating current (AC) is defined as the current with directions varying with time. The pulsating DC is defined as the current with instantaneous value varying with time while the current direction remains unchanged. The time interval is defined as the minimum time unit describing the variation of the instantaneous value of the current. The duty cycle is defined as the time unit consisting of a limited number of time intervals to form regular repetition of the power supply current. The duty cycle includes a cleaning duty cycle in a cleaning state of the electrical heating module and/or a vaping duty cycle in different vaping states of the electrical heating module, such as a small-flow state (that is, a mouth-suction working state) and a large-flow state (that is, a lung-suction working state). The time range is defined as the time span composed of a limited number of identical duty cycles. The current amplitude is defined as the maximum absolute value of the instantaneous value of the current in a time interval. The variation range of the instantaneous value of the current or voltage, referred to as the variation range of the current or voltage amplitude, is defined as the difference between the maximum value and the minimum value of the current or voltage in one duty cycle, that is, the ratio of the peak-to-peak value of the current or voltage to the maximum value of the absolute value of the current or voltage. The width (duty ratio) is defined as the ratio of the on-state time to the total time in one duty cycle. The waveform of the current is defined as the form of the instantaneous value of the current over time. The pulsating wave is defined as the waveform with non-continuous variation of the current instantaneous value. The continuous wave is defined as the waveform with continuous variation of the current instantaneous value. The regular wave is defined as the waveform with periodic variation in a duty cycle. The irregular wave is defined as the waveform with non-periodical variation in a duty cycle. The regular repetition of the waveform is defined as the waveform consisting of a limited number of identical duty cycles in a time range. The irregular repetition of the waveform is defined as the waveform consisting of a plurality of different duty cycles in a time range.

When an inductive load or a capacitive load is contained in the circuit, a phase difference can be generated between the current and the voltage of the load. For easy description, the electrical heating module of the personal vaping device can be considered as a resistive load in circuit analysis without a special description. It can be seen from Ohm's law that when the circuit supplies power to the electrical heating module, there is no phase difference between the current passing through the electrical heating module and the voltage at the two terminals of the electrical heating module, and the current I and the voltage U satisfy Ohm's Law, shown as $U=IR$, where R is the resistance value of the resistive load represented by the electrical heating module. Therefore, in most of the descriptions of the current supplied to the electrical heating module, the change of the voltage can be used to describe the change of the current, and the change of the current can also be used to describe the change of the voltage. For the case where the electrical heating module contains an inductive load or a capacitive load, it will be described in detail when necessary.

The terms (i.e., first and second) used herein are intended to describe elements and used to distinguish one element from another, which are not intended to limit these elements. For example, but not limited to, a first element may be referred to as a second element, and similarly, a second element may be referred to as a first element without departing from the scope of embodiments of the present disclosure. The term "and/or" used herein includes any and all combinations of one or more of the associated listed items. The term "positive/negative" used herein means the relativity between two objects, such as, but not limited to, a forward connection current may be referred to as a reverse connection current, and similarly, a reverse connection current may be referred to as a forward connection current without departing from the scope of the embodiments of the present disclosure.

The technical solutions of the embodiments of the present disclosure are clearly and completely described below with reference to the accompanying drawings, and the described embodiments are only a part of the embodiments of the present disclosure. As shown in FIGS. 2-28, a power supply control method for an electrical heating module of a personal vaping device is illustrated, which is the first aspect of the present disclosure. As shown in FIGS. 29-50, a power supply control circuit for implementing the method according to the above embodiments and a control method thereof, and the technical solution of encapsulating several electronic components by a module discrete integrating mode to reduce the occupied space of the power supply control circuit, are illustrated, which are the second aspect of the present disclosure. Although the technical effects of this application are described with reference to the electronic cigarette atomizing the e-cigarette oil and the electronic cigarette baking the non-combustible tobacco at low temperature, they can also be embodied in other equipment in which substances are heated and volatilized into aerosol or gas when used. All other embodiments obtained by those skilled in the art based on the embodiments of the present disclosure without paying creative efforts shall fall within the scope of protection of the present disclosure. The following embodiments and the technical features thereof can be combined with each other without conflict.

The personal vaping device provided herein generally includes an electrical heating module designed for heating vaping products (such as e-cigarette oil and tobacco), a DC power supply designed for providing a heating power supply for the electrical heating device, and a power supply control circuit designed for controlling the on/off of the current output and converting a DC output from the DC power supply into a supply current having a periodical variation in at least one of direction, instantaneous value, and on-state time. It should be noted that the electrical heating module provided herein can be an atomizer for atomizing e-cigarette oil or tobacco paste and a heater for baking and heating non-combustible tobacco.

A power supply control method for an electrical heating module of a personal vaping device provided herein includes the following steps. A DC power supply is provided. A DC output from the DC power supply is converted into a supply current having a periodical variation in at least one of direction, instantaneous value, and on-state time. The supply current is applied to the electrical heating module. The conversion of periodical variation in at least one of direction, instantaneous value, and on-state time is described in detail with specific embodiments as follows.

Figure 2:
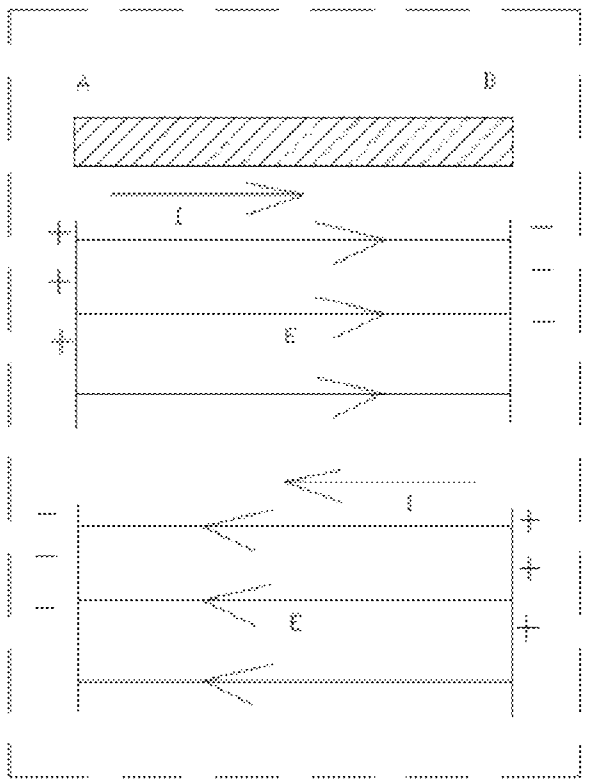
FIG. 2 schematically illustrates an electrical heating module and an electrical field distribution of the electrical heating module according to an embodiment of the present disclosure.

An electrical heating module for a personal vaping device is illustrated in FIG. 2. When a direction-constant current is applied to the electrical heating module, an electrical field E with a constant direction is generated. Foreign substances (i.e., carbide) generated by heating the oil guide cotton will be adsorbed on the surface of the electrical heating module due to the electrical field E. If the direction of the current continues to be constant, foreign substances will be accumulated on the surface of the electrical heating module, lowering the thermal conductivity of the electrical heating module and damaging the electrical heating module. However, if the direction of the electrical field E is changed, the foreign substances attached to the surface of the electrical heating module are separated from the electrical heating module due to the repulsion force of the electrical field E, which plays a role in cleaning the electrical heating module. That is, if the direction of the current is changed once, the electrical heating module is cleaned once. If the external force is applied to the surface of the electrical heating module at the moment, the foreign substances can be completely separated from the surface of the electrical heating module. The electrical heating module is powered by adopting a direction-alternative current in a heating cycle, that is, an alternating current (AC) is applied to the electrical heating module, which can enhance the heating balance of the electrical heating module, and drive the electrical heating module to generate thermal expansion and cold contraction through controlling the on-off where the current changes the direction or the value of the heating power, so as to produce tiny mechanical oscillation, thereby allowing the deposits on the surface of the electrical heating module to fall off. By controlling the alternate transform of the direction of the electrical field force of the electrical heating module, the current skin effect on the outer surface of the electrical heating module is not continuous, air and smoke ions near the outer surface are alternately vibrated, and the thermal field oscillation can be generated. Therefore, by applying the AC to the electrical heating module, the carbon deposition in the electrical heating module of the e-cigarette can be effectively prevented. It should be noted that foreign substances are only parts of the impurities, and other impurities are not listed one by one.

Therefore, by applying a current having a periodical variation in direction under a preferred frequency range that is determined according to a preset parameter to the electrical heating module, the cleanliness of the surface of the electrical heating module can be maintained. Meanwhile, by changing the instantaneous value of the supply current according to a preset parameter, the temperature of the electrical heating module can be controlled designedly, and the service life of the electrical heating module can be prolonged. Moreover, by changing the on-state time of the power supply current according to a preset parameter, the temperature of the electrical heating module can be controlled designedly and inhibited from rising too quickly, which saves energy consumption and enhances the use performance of the electrical heating module.

Figure 3:
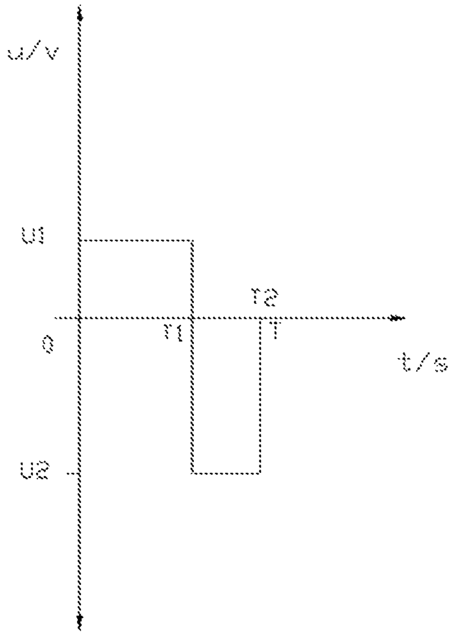
FIG. 3 is a coordinate diagram showing a relationship between voltage and time in a duty cycle of a power supply method according to an embodiment of the present disclosure.

FIG. 3 is a coordinate diagram showing a relationship between voltage variation and time in a duty cycle in a method for supplying an AC to a personal vaping device. In the method, the waveform variation of the AC is mainly concentrated in one time interval. By applying a current with waveform variation in one time interval, the frequency of the current can be changed, which can clean the electrical heating module while ensuring the electrothermal conversion efficiency. The method includes the following steps.

Referring FIG. 3, the electrical heating module is provided, which has a first end A and a second end B. In a first duty cycle 0-T (minimum duty cycle), where 0-T is equal to 0-$T_2$, and $T_2$ is coincident with T. In a duty cycle, a total energy provided by an electrical field to the electrical heating module is a constant as Q to ensure a constant heating power and a stable taste of the smoke provided by the personal vaping device. The first duty cycle 0-T is composed of a first time interval (0-$T_1$) and a second time interval ($T_1$-T). In the first time interval 0-$T_1$, a first current $I_1$ flows from the first end A to the second end B, and a first energy value generated by the first current $I_1$ passing through the electrical heating module is α*Q. In the second time interval $T_1$-T, a second current $I_2$ flows from the second end B to the first end A, and a second energy value generated by the second current $I_2$ passing through the electrical heating module is β*Q. The total energy Q meets the following formulas:

$$Q=\alpha*Q+\beta*Q \quad (1); \text{ and}$$

$$\alpha+\beta=1 \quad (2);$$

where α represents an energy coefficient of the first energy value; β represents an energy coefficient of the second energy value; 1>α>0; and 1>β>0.

In the first time interval 0-$T_1$, the first energy obtained by the electrical heating module is α*Q, and in the second time interval $T_1$-T, the second energy obtained by the electrical heating module is β*Q. However, in one duty cycle, the total energy Q obtained by the electrical heating module is a constant and is proportionally distributed in different time intervals.

The total energy of the electrical heating module is constant and is proportionally distributed to the electrical heating module in a forward and reverse distribution mode. The energy is randomly distributed on the electrical heating module, and combined with the direction variation of the current, the heating uniformity of the electrical heating module is achieved and the stability of the heating temperature is improved compared with a traditional design. In addition, foreign substances (i.e., carbides) can be effectively prevented from accumulating on the surface of the electrical heating module, so that the electrical heating module can be cleaned, and the pure taste of the atomized e-cigarette oil or the baked non-combustible tobacco is ensured.

The constant total energy obtained by the electrical heating module in one duty cycle makes the generated heat constant and ensures that the smoke provided by the personal vaping device has a stable taste. The total energy Q is distributed proportional in different time intervals such that a first electrical field $E_1$ is generated in the first time interval, and a second electrical field $E_2$ is generated in the second time interval. The first time interval and the second time interval can be equal or different such that the electrical field can be repeatedly oscillated according to a certain frequency or irregularly oscillated in the electrical heating module, and impurities attached to the surface of the electrical heating module can be effectively cleaned.

In some embodiments, referring to FIG. 3, a voltage when the first current $I_1$ passes through the electrical heating module is a first voltage $U_1$, and a voltage when the second current $I_2$ passes through the electrical heating module is a second voltage $U_2$, where the first voltage $U_1$ and the second voltage $U_2$ satisfy the following formula:

$$U_1\neq U_2 \quad (3).$$

It should be noted that the electrical heating module can also be powered under $U_1=U_2$.

Figure 4:
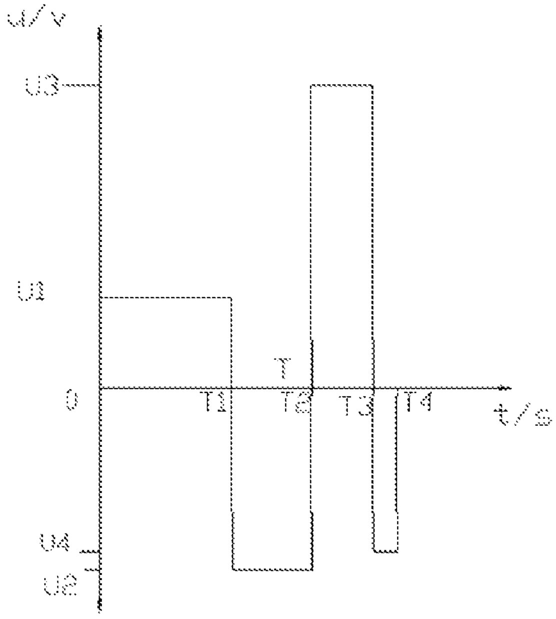
FIG. 4 is a coordinate diagram showing a relationship between voltage and time in a first duty cycle and a second duty cycle of the power supply method according to an embodiment of the present disclosure.
Figure 5:
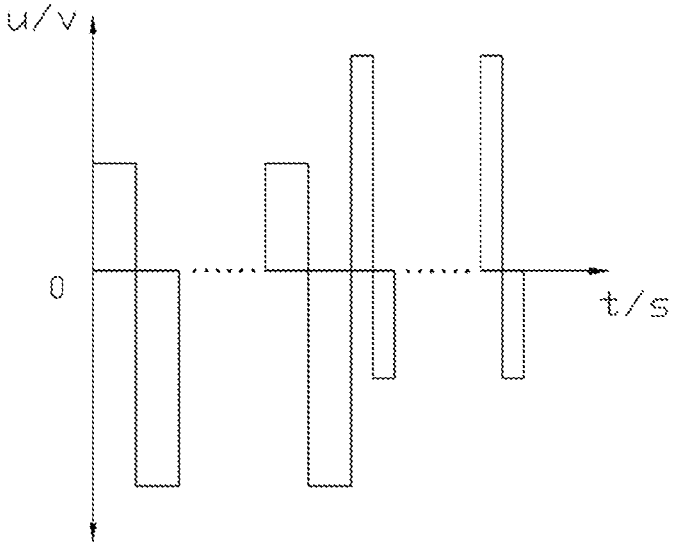
FIG. 5 is a coordinate diagram showing a relationship between voltage and time in a first time interval and a second time interval of the power supply method according to an embodiment of the present disclosure.

In some embodiments, referring to FIG. 4, after the first AC is applied to the electrical heating module, a second AC is applied to the electrical heating module, and a duty cycle of the second AC is defined as a second duty cycle T ($T_2$)-$T_4$. The second duty cycle T-$T_4$ includes a third time interval (T-$T_3$) and a fourth time interval ($T_3$-$T_4$). In the second duty cycle T ($T_2$)-$T_4$, a total energy provided by an electrical field to the electrical heating module is Q, and Q>0. In the third time interval T-$T_3$, a third current $I_3$ flows from the first end A to the second end B, and a third energy value generated by the third current $I_3$ passing through the electrical heating module is μ*Q. In the fourth time interval $T_3$-$T_4$, a fourth current $I_4$ flows from the second end B to the first end A, and a fourth energy value generated by the fourth current $I_4$ passing through the electrical heating module is γ*Q. The total energy Q meets the following formulas:

$$Q=\mu*Q+\gamma*Q \quad (4); \text{ and}$$

$$\mu+\gamma=1 \quad (5);$$

where μ represents an energy coefficient of the third energy value; γ represents an energy coefficient of the fourth energy value; Q is randomly distributed; 1>μ>0; and 1>γ>0.

In some embodiments, referring to FIG. 4, μ and γ meets the following formulas:

$$\mu\neq\alpha \quad (6); \text{ and}$$

$$\gamma\neq\beta \quad (7).$$

In some embodiments, a voltage when the third current $I_3$ passes through the electrical heating module is a third voltage $U_3$, and a voltage when the fourth current $I_4$ passes through the electrical heating module is a fourth voltage $U_4$, where the first voltage $U_1$, the second voltage $U_2$, the third voltage $U_3$, and the fourth voltage $U_4$ satisfy the following formulas:

$$U_3\neq U_4 \quad (8);$$

$$U_3\neq U_1 \quad (9); \text{ and}$$

$$U_4\neq U_2 \quad (10).$$

It should be noted that the frequency f of the AC is not higher than 1000 Hertz (Hz). It has been found through experiments that the frequency of the AC cannot be too high, otherwise, the electrical heating module will generate a skin effect due to high-frequency current such that the current mainly passes through the surface of the electrical heating module, leading to the damage to the electrical heating module as the excessive heating on the surface of the electrical heating module. Moreover, the frequency of the AC cannot be too low, otherwise, the cleaning effect on the electrical heating module cannot be achieved. In the above set frequency range, the ideal heating effect can be achieved, and the preferred frequency in the state of cleaning the electrical heating module is 300-1000 Hz, that is 300 Hz≤f≤1000 Hz. The preferred frequency in the small-flow vaping state is 80-150 Hz, that is, 80 Hz≤f≤150 Hz, or the preferred frequency in the large-flow vaping state is 25-50 Hz, that is, 25 Hz≤f≤50 Hz. Compared with the condition that the voltage instantaneous value remains unchanged, the electrical heating module can be effectively cleaned by adjusting the frequency of the AC, and the service life of the electrical heating module can be increased by 50-100%, thereby ensuring that the personal vaping device can provide smoke with a stable taste to the user.

It should be noted that the duration of the first duty cycle is not equal to that of the second duty cycle to adjust the frequency of the AC, so as to render energy with different frequencies to be applied to the electrical heating module at different time intervals.

In some embodiments, the T ($T_2$)-$T_3$ time interval is not equal to the $T_3$-$T_4$ time interval. One part of the total energy Q is released in the T ($T_2$)-$T_3$ time interval, and the other part is released in the $T_3$-$T_4$ time interval. Moreover, the directions of energy in the T-$T_3$ time interval and the $T_3$-$T_4$ time interval are different such that the heat distribution is more uniform.

As shown in FIG. 4, a first time range is defined as T', which includes at least two first duty cycles 0-T. A second time range is defined as T", which includes at least two second duty cycles T-$T_4$. By controlling the duration of T' and T", voltages with different waveforms are applied to the electrical heating module as required, so as to prolong the service life of the electrical heating module and avoid carbon deposition of the electrical heating module.

It should be noted that the first time range T' defined in the present embodiment may further include at least one first duty cycle 0-T and at least one second duty cycle T-$T_4$, and the second time range T" may also include at least one first duty cycle 0-T and at least one second duty cycle T-$T_4$. For example, the first time range T' may include two first duty cycles and one second duty cycle, and the second time range T" may include three first duty cycles and two second duty cycles, which are not limited in here.

It should be further noted that the principle of avoiding of carbon deposition on the electrical heating module is described as follows.

It should be further noted that the principle of avoiding carbon deposition on the electrical heating module is described as follows.

In the first aspect, the direction of the electrical field force changes alternately such that the skin effect of the current on the outer surface of the electrical heating module is not continuous, and air and smoke ions near the outer surface alternately oscillate.

In the second aspect, a forward connection current is applied to the electrical heating module in the first time interval 0-$T_1$ of a duty cycle to provide the energy of $\alpha$*Q for the electrical heating module, and then a reverse connection current is applied to the electrical heating module in the second time interval $T_1$-$T_2$ of the duty cycle to provide the energy of $\beta$*Q for the electrical heating module. If $\alpha$*Q>$\beta$*Q, the energy of the electrical heating module provided by the forward connection current is larger than that provided by the reverse connection current, and then the electrical heating module is continuously supplied with the energy provided by forward and reverse connection currents alternately arranged to form forward and reverse electrical fields alternately distributed inside the electrical heating module and the alternate oscillation of charged particles, so as to achieve the uniform distribution of heating energy in the electrical heating module. Other change forms are similar to the above forms and will not be described.

It should be noted that the heating assembly can be a heating wire, a heating sheet, a heating net, and a heating resistor. In view of the personal vaping device using the e-cigarette oil, the heating assembly is generally arranged in the oil guide component, that is, the oil guide component covers the heating assembly. The oil guide component is generally a ceramic oil guide component, an oil guide cotton, etc. The heating assembly can also be arranged outside the oil guide component, which is not limited herein. With respect to the personal vaping device using the non-combustible tobacco, the heating assembly is generally inserted into the non-combustible tobacco.

Figure 6:
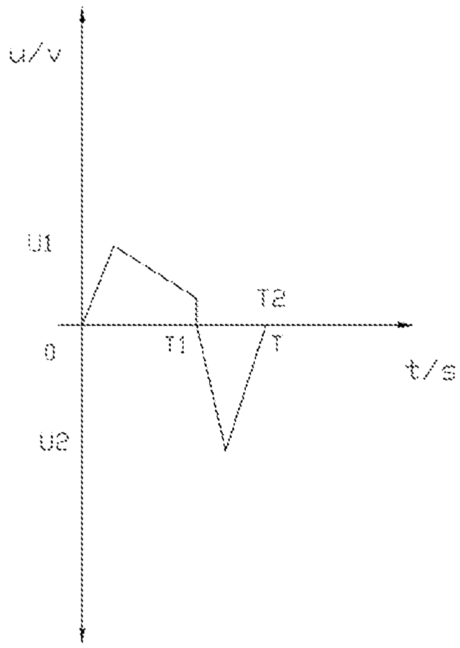
FIG. 6 is a coordinate diagram showing a relationship between voltage and time in a duty cycle of the power supply method according to an embodiment of the present disclosure.
Figure 7:
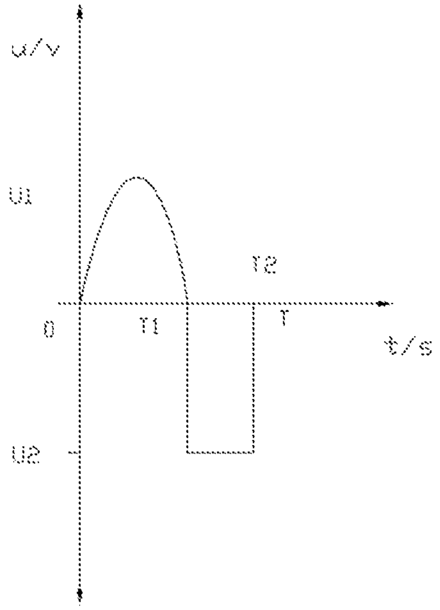
FIG. 7 is a coordinate diagram showing a relationship between voltage and time in a duty cycle of the power supply method according to another embodiment of the present disclosure.

In some embodiments, as shown in FIGS. 6-7, a voltage instantaneous value when the first current $I_1$ passes through the electrical heating module is a first voltage $U_1$. In a first time interval 0-$T_1$, the first voltage $U_1$ is variable over time and forms at least one peak or trough. For example, in the first time interval 0-$T_1$, the first voltage $U_1$ forms a peak as illustrated in FIGS. 6-7. By allowing the first voltage $U_1$ to form a peak or a trough, the first current $I_1$ can generate an instantaneous fluctuation, or the variation of the instantaneous electrical field becomes large, so that foreign substances (i.e., carbides) on the surface of the electrical heating module are instantaneously subjected to the repulsive force of the electrical field, facilitating to the separation of the foreign substances from the electrical heating module. In addition, the obvious fluctuation of the voltage is favorable for the volatilization of the volatile substances in the e-cigarette oil or the non-combustible tobacco, so that the saturation and the restoration degree of the volatile substances are higher, improving the taste of the e-cigarette oil or the non-combustible tobacco, and thus raising the user satisfaction. It can be understood that the waveforms in the accompanying drawings are merely schematic, and are not intended to limit the protection scope of the present disclosure. The first voltage $U_1$ can form different waveforms by using a corresponding rectification circuit, and details are not described herein again.

Figure 8:
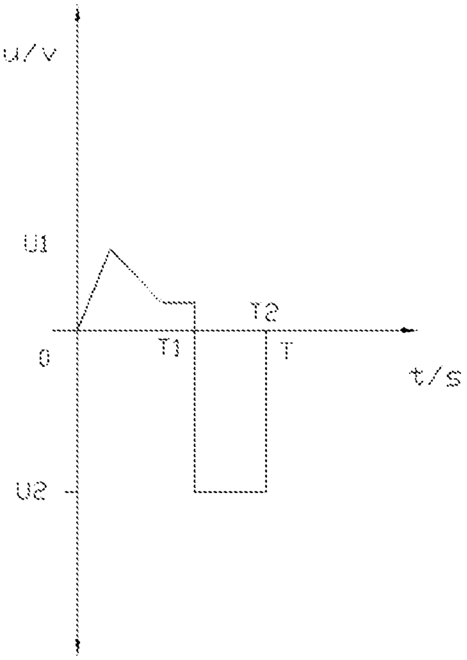
FIG. 8 is a coordinate diagram showing a relationship between voltage and time in a duty cycle of the power supply method according to another embodiment of the present disclosure.
Figure 9:
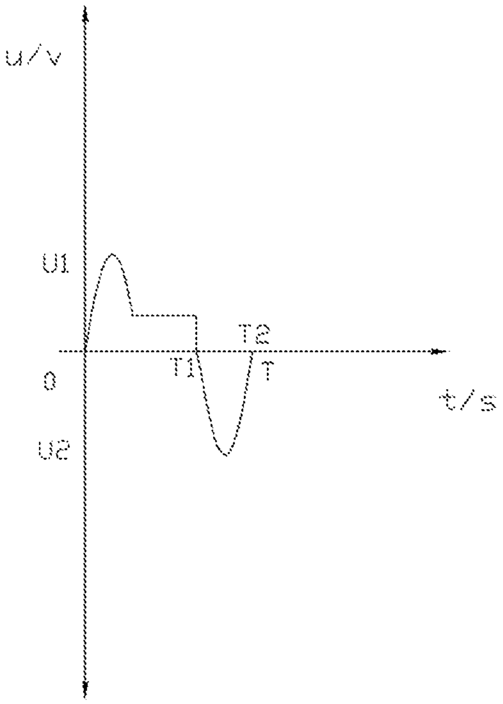
FIG. 9 is a coordinate diagram showing a relationship between voltage and time in a duty cycle of the power supply method according to another embodiment of the present disclosure.

In some embodiments, referring to FIGS. 8-9, in the first time interval 0-$T_1$, the first voltage $U_1$ further forms a constant-voltage section. The constant-voltage section is generated while the first voltage $U_1$ forms a peak or a trough, which can improve the conversion efficiency of the electric energy to the heat energy. It should be noted that the number of the constant section may also be at least two, which is not limited herein.

Figure 10:
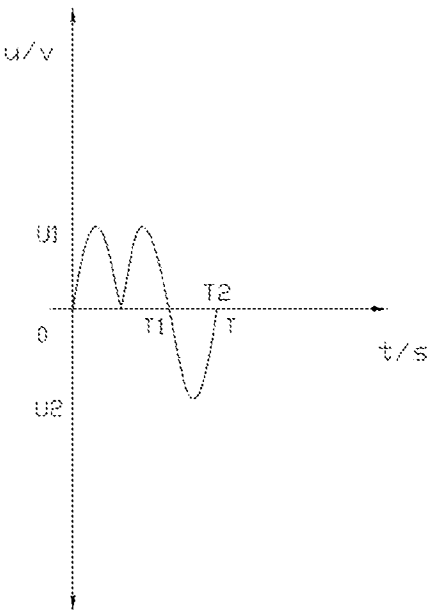
FIG. 10 is a coordinate diagram showing a relationship between voltage and time in a duty cycle of the power supply method according to another embodiment of the present disclosure.

In some embodiments, referring to FIG. 10, in the first time interval 0-$T_1$, the first voltage $U_1$ forms two peaks. It should be noted that in the first time interval 0-$T_1$, the first voltage $U_1$ may also form more than two peaks, or more than two troughs. Through the above arrangement, the change frequency of the electrical field can be increased, the volatilization of the volatile substances in the e-cigarette oil or the non-combustible tobacco can be induced better, and thus improving the taste of the e-cigarette oil or the non-combustible tobacco.

It should be noted that the voltage instantaneous value when the second current $I_2$ passes through the electrical heating module is the second voltage $U_2$, and in the second time interval $T_1$-T, the second voltage $U_2$ is a variable that varies with time and forms at least one peak or trough. Through the above arrangement, the separation of the foreign substances from the electrical heating module is facilitated. In addition, the obvious fluctuation of the voltage is favorable for the volatilization of the volatile substances in the e-cigarette oil or the non-combustible tobacco, so that the saturation and the reduction degree of the volatile substances are higher, improving the taste of the e-cigarette oil or the non-combustible tobacco, and thus raising the user satisfaction. In some embodiments, in the second time interval $T_1$-T, the second voltage $U_2$ forms at least a constant-voltage section, or the second voltage $U_2$ forms more than two peaks or more than two troughs.

In an embodiment, a method of supplying AC for the personal vaping device is also provided, in which the waveform variation of the AC is distributed in different time intervals, that is, there is only one waveform in one time interval. By using this method, the conversion efficiency of electric heating can be ensured while cleaning the electrical heating module, and the control difficulty of the current waveform is also reduced. The method includes the following steps.

The electrical heating module is provided, which has a first end A and a second end B. The AC is applied to the electrical heating module, where a duty cycle of the AC includes at least three time intervals; in a first time interval, the current flows from the first end A to the second end B; in a second time interval, the current flows from the second end B to the first end A; and in s third time interval, the current flows from the first end A to the second end B or the second end B to the first end A, which is not specifically specified herein.

Figure 11:
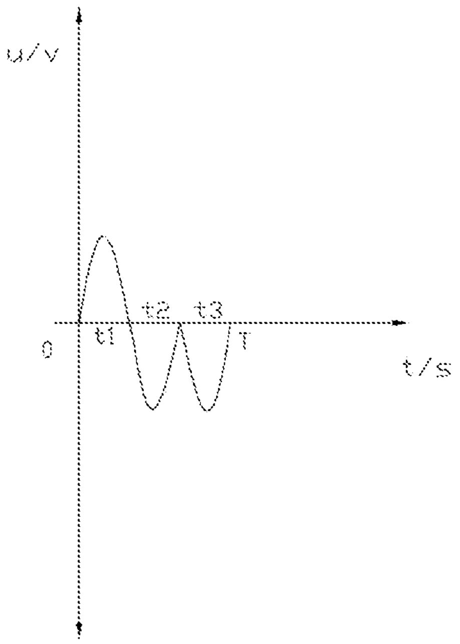
FIG. 11 is a coordinate diagram showing a relationship between voltage and time in a duty cycle of another power supply method according to another embodiment of the present disclosure.

For a more perceptual intuitive description of the above-mentioned solution, the voltage variation is described. Referring to FIG. 11, the duty cycle 0-T of the AC includes at least the first time interval 0-$T_1$, the second time interval $T_1$-$T_2$, and the third time interval $T_2$-$T_3$. In the first time interval 0-$T_1$, the current is positive in direction and flows from the first end A to the second end B. In the second time interval $T_1$-$T_2$, the current is negative in direction and flows from the second end B to the first end A. In the third $T_2$-$T_3$, the current is negative in direction and flows from the second end B to the first end A. It should be noted that a duty cycle 0-T of the AC includes at least the first time interval 0-$T_1$, the second time interval $T_1$-$T_2$, and the third time interval $T_2$-$T_3$, and the number of specific time intervals can be selected according to requirements, which is not specifically specified herein.

According to the method of the electrical heating module provided herein, by continuously changing the direction of the current, energy from different directions is distributed to the electrical heating module, and the change frequency of the direction of the current in the electrical heating module is reasonably controlled. Compared with the traditional design, the heating uniformity of the electrical heating module is realized, which stabilizes the heating temperature of the electrical heating module and prevents foreign substances (i.e., carbides) from being accumulated on the surface of the electrical heating module, so as to achieve the self-cleaning of the electrical heating module and the improve the taste of atomized e-cigarette oil or baked non-combustible tobacco.

Figure 12:
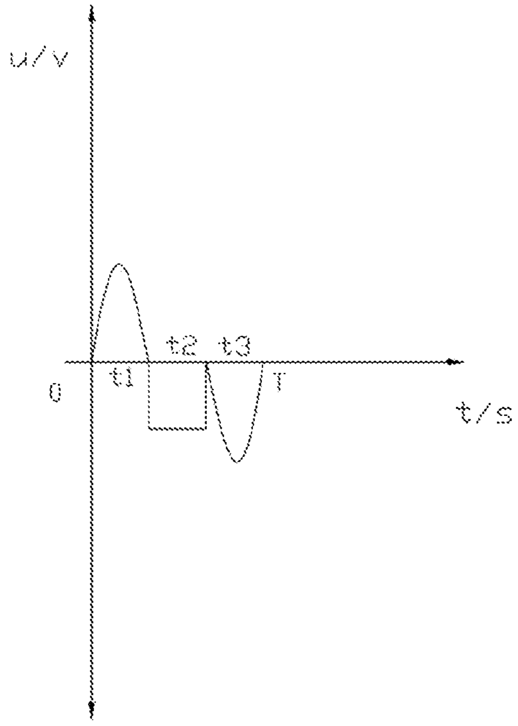
FIG. 12 is a coordinate diagram showing a relationship between voltage and time in a duty cycle of another power supply method according to another embodiment of the present disclosure.

In some embodiments, referring to FIG. 12, in the second time interval $T_1$-$T_2$, the voltage is constant. It should be noted that the voltage is constant in at least one of the first time interval 0-$T_1$, the second time interval $T_1$-$T_2$, and the third time interval $T_2$-$T_3$. In this case, the conversion efficiency of the electric energy to the heat energy can be enhanced, and the relationship between the electric energy conversion efficiency and the heating uniformity of the electrical heating module can be balanced.

In some embodiments, referring to FIG. 11, the voltage is variable in the first time interval 0-$T_1$, the second time interval $T_1$-$T_2$, and the third time interval $T_2$-$T_3$. It should be noted that the voltage is variable in at least one of the first time interval 0-$T_1$, the second time interval $T_1$-$T_2$, and the third time interval $T_2$-$T_3$. For example, in FIG. 12, the voltage is variable in the first time interval 0-$T_1$ and the third time interval $T_2$-$T_3$. By setting the voltage to be variable, the heating uniformity of the electrical heating module can be improved, and the volatilization of volatile substances in the e-cigarette oil or the non-combustible tobacco is facilitated, so that the saturation and the reduction degree of the volatile substances are higher, improving the taste of the e-cigarette oil or the non-combustible tobacco, and thus raising the user satisfaction.

It should also be noted that the output voltage, the output current, the waveform of the voltage, the alternating frequency, the phase and the zero displacement can be adjusted, besides, the duration of the on-state time can be adjusted, so as to achieve the flexible use.

Figure 13:
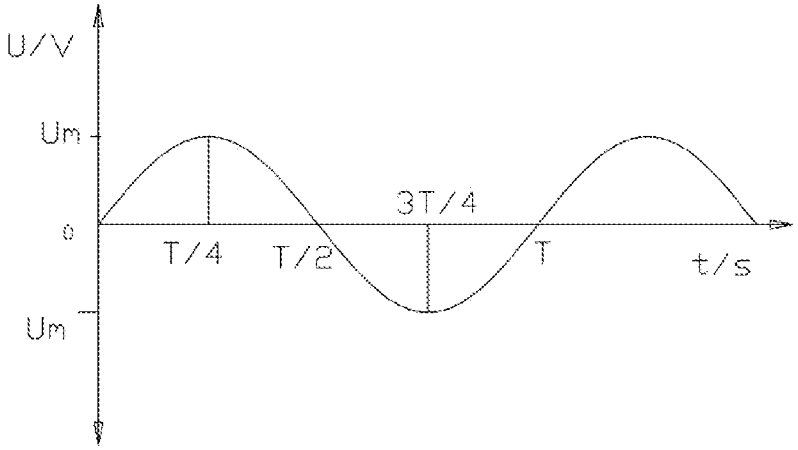
FIG. 13 is a schematic diagram of a sine wave output voltage provided by another power supply method according to an embodiment of the present disclosure.
Figure 14:
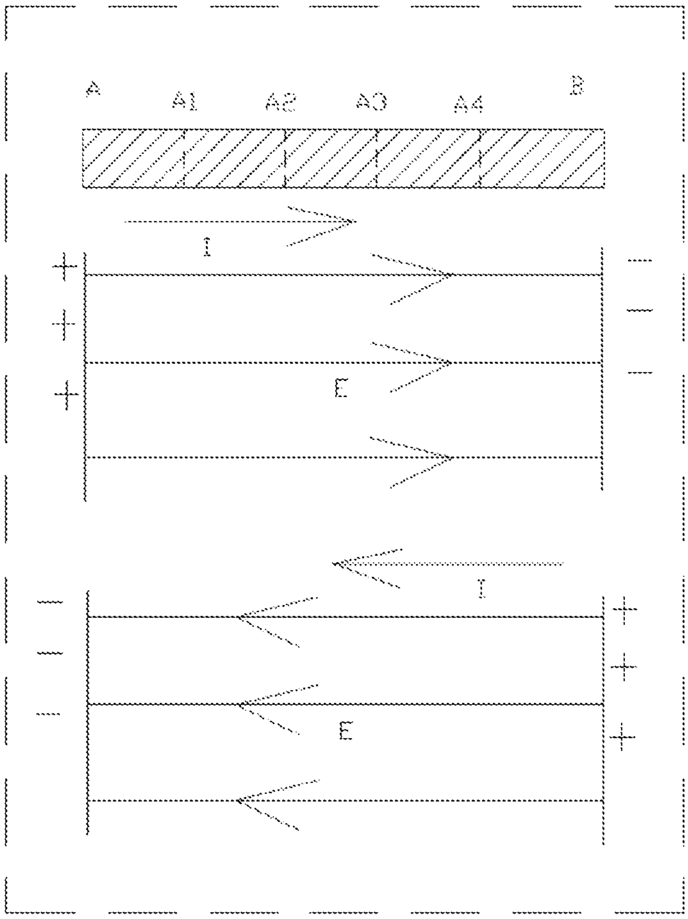
FIG. 14 schematically illustrates transformation of an electrical field provided by another power supply method according to an embodiment of the present disclosure.
Figure 15:
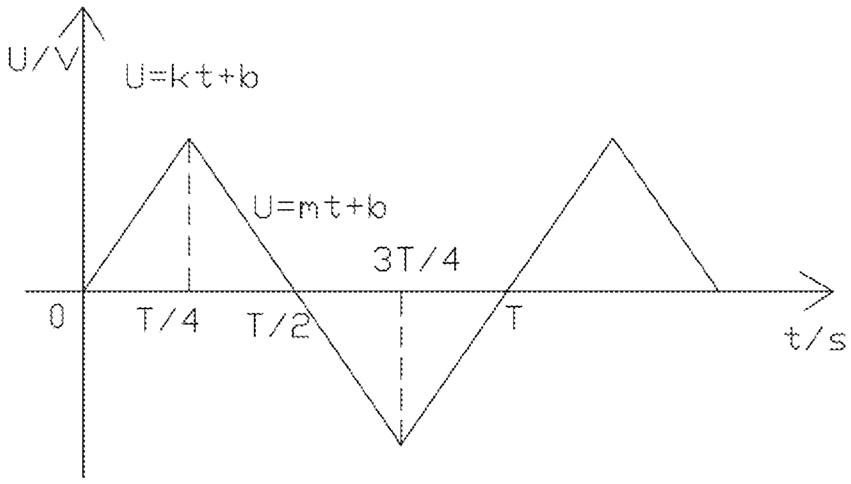
FIG. 15 is a schematic diagram of a triangular wave output voltage provided by the power supply method according to an embodiment of the present disclosure.

Referring to FIGS. 13-15, another method of supplying AC for the electrical heating module is provided, in which the waveform of the AC remains unchanged, and the instantaneous value of the current is slowly changed over time, so that the electrical heating module can be cleaned while avoiding the high local temperature in the electrical heating module. The method includes the following steps.

The electrical heating module is provided, which has the first end A and the second end B. A current flowing from the first end A to the second end B is defined as a forward connection current, and a current flowing from the second end B to the first end A is defined as a reverse connection current.

An AC is provided to supply the electrical heating module in an alternately forwarding and reversing manner in a duty cycle.

For easy description, time is defined to be started from 0, and a duty cycle is defined as 0-T. The forward current or voltage of the AC slowly rises from 0 to a peak value in 0-T/4 of a first time interval, and slowly falls from the peak value to 0 in T/4-T/2 of the first time interval. The reverse current or voltage of the AC slowly rises from 0 to a peak value in T/2-3T/4 of a second time interval, and slowly falls from the peak value to 0 in 3T/4-T of the second time interval.

The ACs conforming to the sine wave curve and the triangular wave curve are described below.

Referring to FIG. 13, an AC conforming to a sine wave (referred to as cosine wave) curve is provided, where a voltage U of the AC meets the following formula:

$$U=U_m*\mathrm{Sin}(\omega t+\mu) \tag{11}$$

where $U_m$ represents a peak value of the AC; ω represents an angular frequency of the AC; μ represents an initial phase; t represents time; and the minimum duty cycle meets:

$$T=2\pi/\omega \tag{12}$$

where T represents a duration of the duty cycle.

A duty cycle includes a first time interval 0-T/2 and a second time interval T/2-T, where a forward current flows. The electrical heating module (heating wire) having a first end A and a second end B is illustrated in FIG. 14. In the first time interval 0-T/2 the forward current flows from the first end A to the second end B to render the AB segment of the heating wire become thinner, and the time is infinitely enlarged. In this case, a heat-generating region moves slowly from the first end A to the second end B along the electrical heating module in the sequence of A-A1, A1-A2, A2-A3, A3-A4, . . . B. In this way, the front region of the heating wire is firstly heated followed by the heating of the rear region of the heating wire, which causes the situation that the first end A is overheated, while the second end B may not suffer heating, leading to an unbalanced heat distribution on the heating wire. In the second time interval T/2-T, the current direction is reversed, and flows in the reverse direction, namely, flowing from B to A, to render the B-A segment of the heating wire become thinner, and the time is infinitely enlarged. In this case, a heat-generating region moves slowly from the second end B to the first end A along the heating wire in the sequence of B-$A_4$, $A_4$-$A_3$, $A_3$-$A_2$, $A_2$-$A_1$, . . . A. In this way, and the front region of the heating wire is firstly heated followed by the heating of the rear region of the heating wire, which causes the situation that the second end B is overheated, while the first end A may not suffer heating. Since the forward current is applied in the first time interval, and the reserve current is applied in the second time interval, the temperature of the first end A is reduced compared with the forward current being applied in the whole duty cycle. It can be seen that in a duty cycle, the heat generated at the first end A and the second end B are relatively higher than that at the middle of the heating wire. If the length of the heating wire is short enough, the temperature of any point on the heating wire tends to be the same. However, in actual situations, the difference in temperature between points on the heating wire always exists. Anyway, the power supply control method provided herein can balance the distribution of heat in the electrical heating module.

In the time interval 0-T/4, the forward current or voltage of the AC slowly rises from 0 to a peak value, the electrical heating module is heated slowly to reach the peak value. In the time interval T/4-T/2, the forward current or voltage of the AC slowly falls from the peak value to 0, and the heat of the electrical heating module declines steadily. In the time interval T/2-3T/4, the reverse current or voltage of the AC slowly rises from 0 to a peak value, the electrical heating module is heated reversely to reach the peak value. In the time interval 3T/4-T, the reverse current or voltage of the AC slowly falls from the peak value to 0, and the heat of the electrical heating module declines steadily. In this way, the thermal shock to the electrical heating module is reduced, and the service life of the electrical heating module is effectively prolonged. In addition, when the electrical heating module is cooperated with the oil guide cotton, as the adsorption rate of the oil guide cotton on the e-cigarette oil is fixed, the adsorption of the e-cigarette oil by the oil guide cotton is more stable, so that there has sufficient time to adsorb enough and moderate e-cigarette oil, effectively avoiding the dry burning and insufficient oil supply of the electrical heating module, thereby preventing the oil guide cotton from burning owing to the over-high local temperature of the electrical heating module.

Referring to FIG. 15, an AC conforming to a triangular wave curve is provided, where a voltage U of the AC meets the following formula:

$$U=kt+b \tag{13}$$

where k is a slope of the triangular wave curve; b is a first constant; and t represents time.

For example, in a time interval 0-T/4, a forward current or voltage of an AC slowly rises from 0 to a peak value, the electrical heating module is heated steadily until the forward current reaches the peak value, and the voltage U meets: U=kt. In the time interval T/4-T/2, the forward current or voltage of the AC slowly falls from the peak value to 0, and the heat of the electrical heating module declines steadily. In the time interval T/2-3T/4, a reverse current or voltage of the AC slowly rises from 0 to a peak value, the electrical heating module is steadily heated in a reverse direction until the reverse current reaches the peak value, and the voltage U meets:

$$U=mt+n \tag{14}$$

where m is a negative slope of the triangular wave curve; n is a second constant; and t represents time.

In the fourth time interval 3T/4-T, the reverse connection current or voltage of the AC slowly falls from the peak value to 0, and the voltage U meets formula (13).

The above-mentioned waveforms are common, which are not limited in the present disclosure. The values of $U_m$, ω, and μ can be adjusted to adjust the direction, amplitude, and phase of the AC. For example, the amplitude of the voltage can be adjusted by regulating the value of $U_m$, the frequency of the AC can be adjusted by regulating the value of ω, and the initial phase (referred to as phase angle) of the AC can be adjusted by regulating the value of μ.

The method of supplying AC for the personal vaping device provided herein has the following beneficial effects.

(1) The electrical heating module is heated or cooled slowly such that the impact force on the electrical heating module is greatly reduced, thereby effectively prolonging the service life of the electrical heating module.

(2) The periodic variation of current/voltage in direction can equalize the heat distribution in the electrical heating module, which can avoid the over-high local temperature of the electrical heating module and local burning of the oil-guiding cotton.

(3) When the electrical heating module is used, the oil guide cotton needs to be arranged on the outer side or the inner side of the electrical heating module. Since the oil guiding capacity of the oil guiding cotton is limited, and the heat generated by the electrical heating module is slowly increased to a maximum value and then decreased slowly, the high and low circulation of the heat can avoid the local burning of the oil guiding cotton caused by insufficient oil supply.

(4) The periodic variation of current/voltage in direction makes the electrical field around the electrical heating module change periodically, avoiding carbon deposition on the surface of the electrical heating module.

Figure 16:
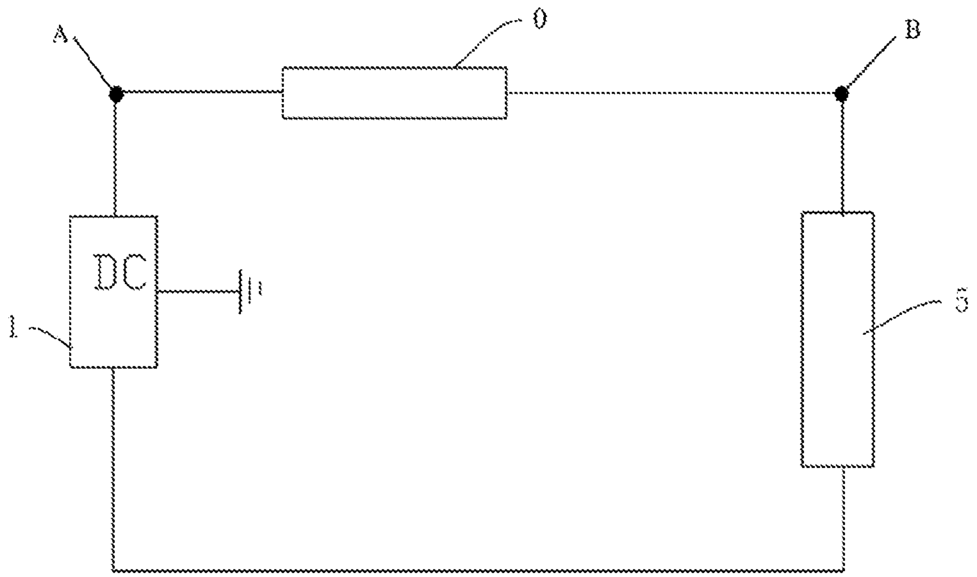
FIG. 16 is a schematic diagram of a power supply control circuit of an electrical heating device in another power supply method according to an embodiment of the present disclosure.

Referring to FIG. 16, an electric heating device is provided in another embodiment, which includes a power supply control circuit, an electrical heating module 5, and a DC power supply 1. The power supply control circuit is composed of a current input terminal A, a current output terminal B, and a current control module 0. The DC power supply 1 supplies a DC to the current control module 0 through the current input terminal A. The current control module 0 is configured to convert the DC into a supply current having a periodical variation in at least one of direction, instantaneous value, and on-state time by using a power supply control method provided in any one of embodiments of the present disclosure. The supply current is applied to the electrical heating module 5 through the current output terminal B. It should be noted that the electrical heating module can be an atomizer configured to atomize e-cigarette oil or paste, a heater configured to heat non-combustible tobacco, or can bake or atomize medical or physiotherapy products by using a heater or atomizer.

It should be noted that in some embodiments of an aspect of the present disclosure, as shown in FIGS. 3-15, the average value point (the bias voltage) of the maximum value and the minimum value of the voltage U in the longitudinal axis can be moved upwards or downwards along the longitudinal axis, so that the waveform of the output voltage moves upwards or downwards along with the up-and-down translation of the average value point, and likewise, the waveform of the output current also moves upwards or downwards accordingly along with the up-and-down translation of the average value point of the time t.

The electrical heating device adopts the power supply method provided hereabove, the heat distribution of the electrical heating module is uniform, avoiding the over-high local temperature of the electrical heating module, and thus prolonging the service life of the electrical heating module. The directions of the electrical field on the electrical heating module are alternate, so that foreign substances (i.e., carbides) can be effectively prevented from accumulating on the surface of the electrical heating module, guaranteeing the cleaning of the electrical heating module and the taste of the atomized e-cigarette oil or the baked non-combustible tobacco. The technical advantages of the electrical heating device have the same effects on heating volatile liquid and solid active substances, and the application range of the present disclosure is not limited to e-cigarette oil and non-combustible tobacco.

A method of supplying a pulsating DC to the electrical heating module of the personal vaping device and a power supply control circuit for implementing the method are also provided. The power supply control circuit is used for modulating a voltage of a DC power supply into a first target voltage and a second target voltage which are alternately changed followed by heating the electrical heating module, suppressing the temperature rise of the electrical heating module, enabling the electrical heating module to be uniformly heated, prolonging the service life of the electrical heating module, and improving the use performance of the electrical heating module.

In the traditional personal vaping device, the electrical heating module generally adopts a DC with a constant instantaneous value for heating. In this case, the temperature at the surface of the electrical heating module is continuously raised without control until an over-high level, the heat in different regions of the electrical heating module tends to be different due to the production variance, and the temperature at different regions shows difference under the action of the constant current, so that the region with an over-high temperature of the electrical heating module is damaged in advance. According to the method of applying the pulsating DC to the personal vaping device provided in embodiments of the present disclosure, by using the current control module, the constant-voltage DC output by the DC power supply is modulated into a pulsating DC with constantly varying instantaneous values presenting various waveforms according to a certain frequency, and the pulsating DC with various waveforms is applied to the electrical heating module. The waveform variation of the pulsating DC is described with the terms shown in Table 1.

TABLE 1

Relating terms of waveform description of the pulsating DC

| Waveform description | Regular wave | Irregular wave |
|---|---|---|
| Regular repetition | Regular repetition of regular wave | Regular repetition of Irregular wave |
| Irregular repetition | Irregular repetition of regular wave | Irregular repetition of Irregular wave |

The pulsating DC with various waveforms enables the temperature of the electrical heating module to continuously change with the variation of the instantaneous value of the voltage, so that the electrical heating module is not always at a high temperature and is heated uniformly, which can prolong the service life of the electrical heating module. Besides, the power supply control method used in the personal vaping device can also improve the restoration degree of the e-cigarette oil and the tobacco paste, and raises the taste of the heated non-combustible tobacco and the atomized aerosol.

Figure 17:
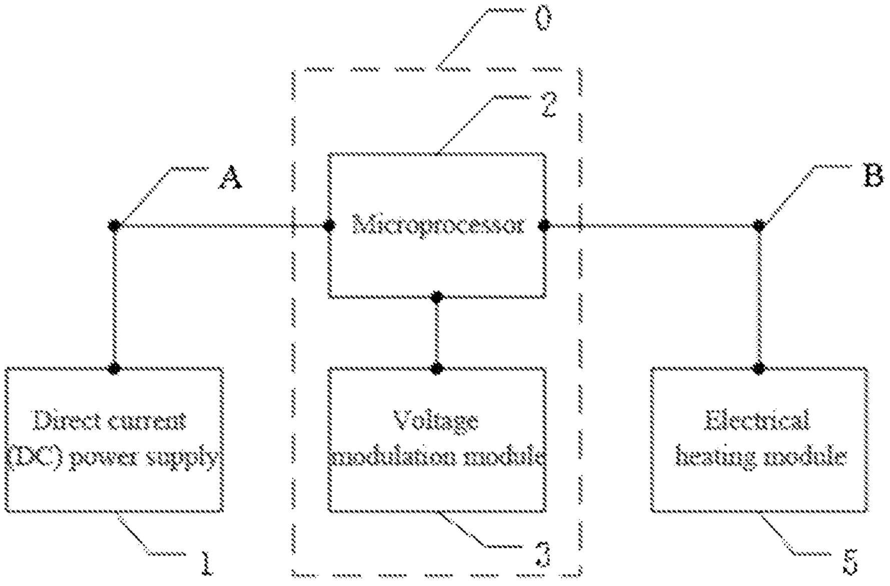
FIG. 17 is a structural diagram of a power supply control circuit according to an embodiment of the present disclosure.
Figure 18:
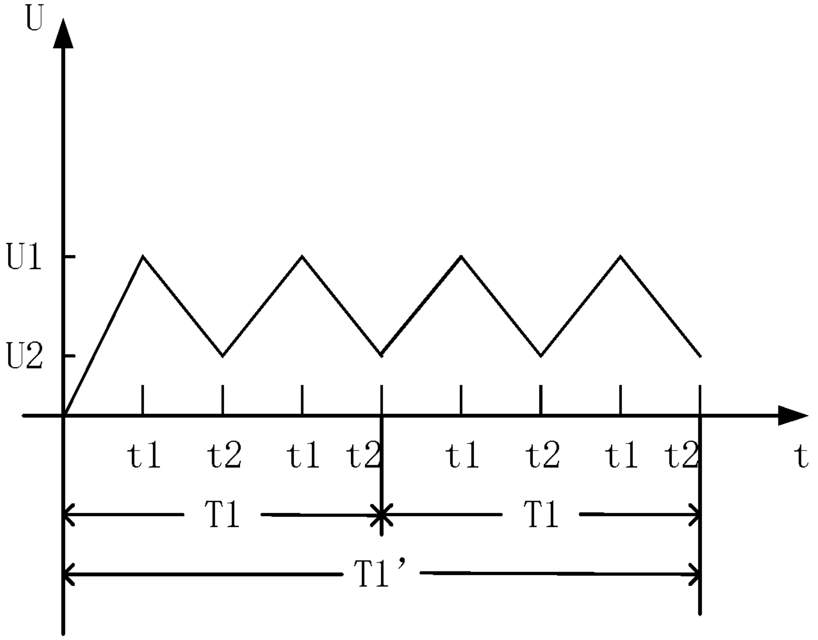
FIG. 18 is a timing diagram of a power supply method according to an embodiment of the present disclosure.

Referring to FIGS. 17-18, a power supply control circuit and a control method thereof are provided.

FIG. 17 illustrates a schematic structural diagram of the power supply control circuit, and FIG. 18 illustrates a timing diagram of an output voltage of the power supply control circuit.

The power supply control circuit is configured to modulate a DC output from a DC power supply into a supply current having a periodic variation in instantaneous value. The supply current is generally a pulsating DC and configured to be applied to an electrical heating module 5. The power supply control circuit includes a current input terminal A, a current control module 0, and a current output terminal B, where the current control module 0 includes a microprocessor 2 and a voltage modulation module 3. The microprocessor 2 is configured to control the voltage modulation module 3. The voltage modulation module 3 is configured to convert the output voltage U of the DC power supply 1 into the pulsating direct current to be fed to the electrical heating module 5. The waveform characteristic of the pulsating DC is a regular repetition of a regular wave. The electrical heating module 5 can use the pulsating DC output from the voltage modulation module 3 to heat.

The control method of the power supply control circuit is described below.

The voltage modulation module 3 controls the voltage U of the DC power supply to obtain a first output voltage $U_1$ and a first output current $I_1$ according to a first preset parameter set sent by the microprocessor 2 in a first time interval $t_1$ of a first duty cycle $T_1$ in a first time range $T_1'$, and a second output voltage $U_2$ and a second output current $I_2$ according to a second preset parameter set sent by the microprocessor 2 in a second time interval $t_2$ of the first duty cycle $T_1$. The instantaneous values of the first output voltage $U_1$ and the second output voltage are different, and the instantaneous values of the first output current $I_1$ and the second output current $I_2$ are different. The first duty cycle $T_1$ includes at least a first time interval $t_1$ and a second time interval $t_2$. Obviously, the waveform characteristic of the output current generated by the control method is a regular repetition of a regular wave.

It should be emphasized that the difference between the instantaneous value of the output current or the output voltage is determined by the preset parameter sets, which is essentially different from the non-preset ripple generated in the general circuit or the voltage modulation process.

The electrical heating module 5 uses the first output voltage $U_1$, the first output current $I_1$, the second output voltage $U_2$, and the second output current $I_2$ output from the voltage modulation module 3 for heating.

It should be noted that the first duty cycle $T_1$ may include a plurality of first time interval $t_1$ and a plurality of second time interval $T_2$.

It should be noted that the first preset parameter set may include a variation range of the instantaneous value of the first voltage $U_1$ and the frequency of the first voltage $U_1$, and the second preset parameter set may include a variation range of the instantaneous value of the second voltage $U_2$ and a frequency of the second voltage $U_2$. In this way, the voltage modulation module 3 can control the voltage U of the DC power supply to obtain the first output voltage $U_1$ and the first output current $I_1$ according to the instantaneous value and the frequency of the first voltage $U_1$ sent by the microprocessor 2 in the first time interval $t_1$ of the first duty cycle $T_1$ in the first time range $T_1'$, and the second output voltage $U_2$ and the second output current $I_2$ according to the instantaneous value and the frequency of the first voltage $U_2$ sent by the microprocessor 2 in the second time interval $t_2$ of the first duty cycle $T_1$.

In addition, the electrical heating module 5 can be arranged in an atomizer of an electronic cigarette for atomizing the e-cigarette oil, a heater for baking the non-combustible tobacco at a low temperature, or an electric heating or atomizing device for medical or other applications, which is not limited herein.

It should be noted that the first time interval $t_1$ and the second time interval $t_2$ may be equal or not, which is not limited herein.

According to the control method of the power supply control circuit in this embodiment, the electrical heating module 5 can use the output voltage and the output current, of which the instantaneous values vary continuously for heating, so that the rapid increase in the temperature of the electrical heating module 5 after being electrified is inhibited and the local carbon deposition of the electrical heating module 5 is released. The temperature of the electrical heating module 5 varies along with the instantaneous value of the voltage, so that the electrical heating module 5 is not always at a high temperature and is heated uniformly, which can prolong the service life of the electrical heating module. Besides, the power supply control method used in the personal vaping device can also improve the restoration degree of the e-cigarette oil and the tobacco paste, and raises the taste of the heated non-combustible tobacco and the atomized aerosol.

A power supply control circuit and a control method thereof of the present disclosure are described above with reference to a schematic diagram of a power supply control circuit. Another power supply control circuit and a control method thereof will be described below.

Figure 19:
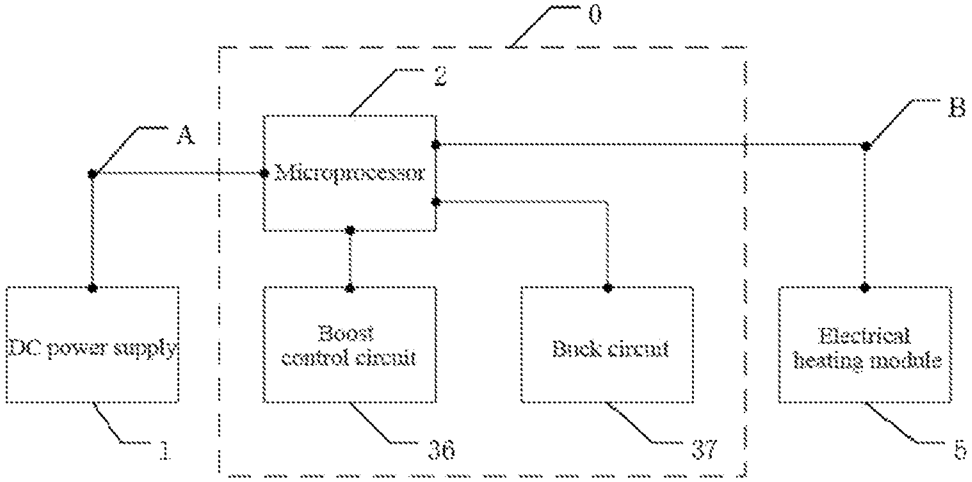
FIG. 19 is a schematic structural diagram of another power supply control circuit according to an embodiment of the present disclosure.
Figure 20:
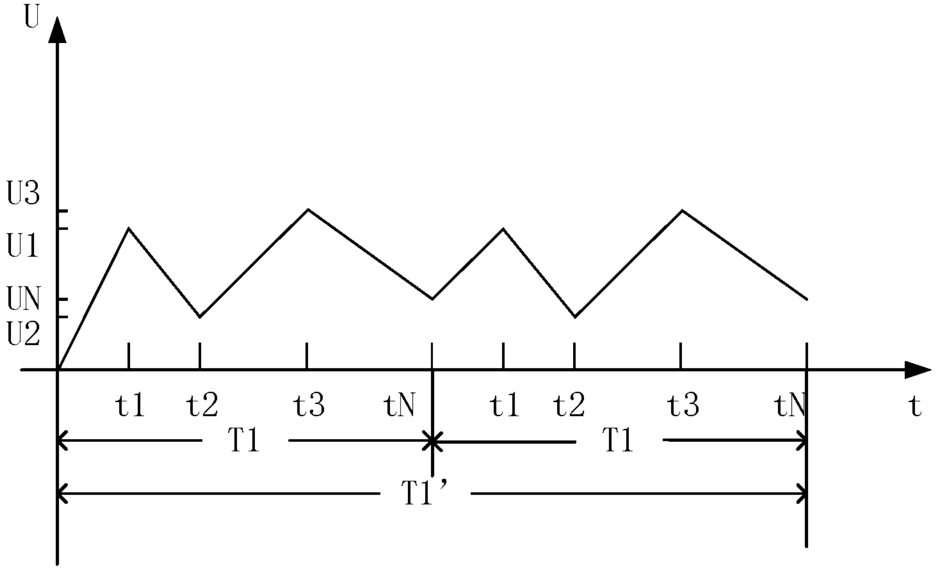
FIG. 20 is a timing diagram of another power supply method according to an embodiment of the present disclosure.
Figure 21:
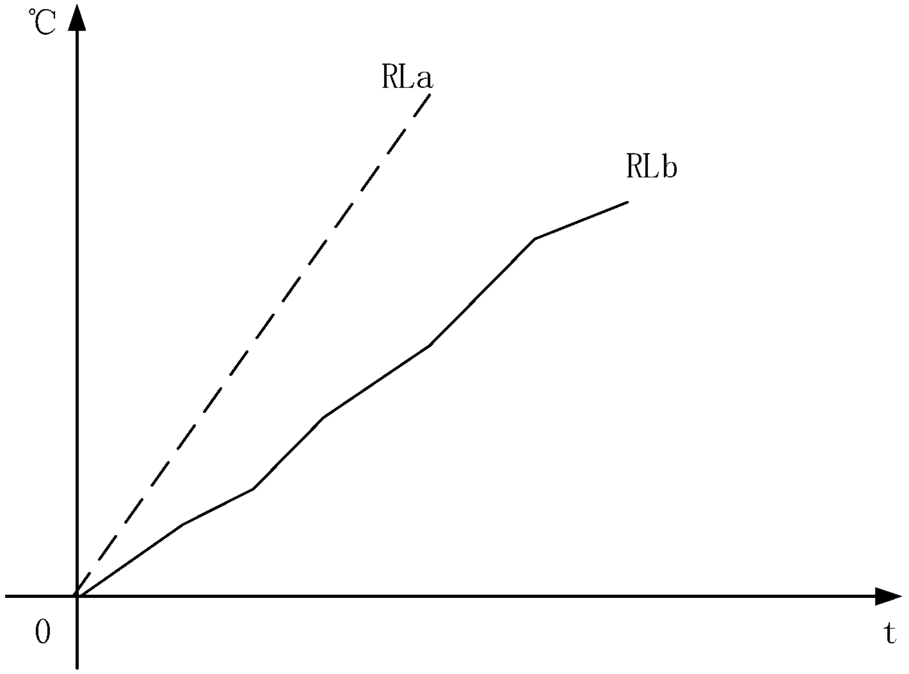
FIG. 21 schematically shows temperature variation with time in an electrical heating module using a conventional power supply method and a power supply method according to an embodiment of the present disclosure, respectively.

FIG. 19 is a schematic structural diagram of another power supply control circuit according to an embodiment of the disclosure. FIG. 20 is a timing diagram of a control method of another power supply control circuit according to an embodiment of the disclosure. FIG. 21 schematically depicts temperature variation over time in the control method of another power supply control circuit and a control method of the conventional power supply control circuit according to an embodiment of the disclosure.

In an embodiment, a power supply control circuit is provided, which includes a DC power supply 1, a current input terminal A, a current output terminal B, a current control module 0, and an electrical heating module 5. The current control module 0 includes a microprocessor 2 and a voltage modulation module.

The voltage modulation module may include a power conversion circuit. The power conversion circuit includes a boost control circuit 36, a buck circuit 37, and a pass-through circuit (not shown in drawings). The power conversion circuit is configured to modulate a voltage U of the DC power supply according to a preset parameter set sent by the microprocessor 2, and output a pulsating DC consisting of a boost voltage, a buck voltage, or a pass-through voltage corresponding to the preset parameter set. In this embodiment, a waveform of the pulsating DC is either a regular repetition of a regular wave or a regular repetition of an irregular wave. Employing a complex current conversion, the electrical heating module has a more uniform temperature distribution, further enhancing the restoration degree of e-cigarette oil and tobacco paste, as well as the taste of heated non-combustible tobacco and atomized aerosol.

It should be noted that the power conversion circuit can be designed to be switched into the boost control circuit 36 in one time interval and switched into the buck circuit 37 in another time interval. In an embodiment, the boost control circuit 36 and the buck circuit 37 are designed to be independent of each other, so as to achieve boosting and bucking without alternate switching of circuits in one circuit. The structure of the boost control circuit 36 and the buck circuit 37 are not limited herein.

A control method of the power supply control circuit is performed through the following steps.

The voltage U of the DC power supply is modulated by the boost control circuit 36 to obtain a first output voltage $U_1$ and the first output current $I_1$ according to a first preset parameter set sent by the microprocessor 2 in the first time interval $t_1$ of the first duty cycle $T_1$ in the first time range T1', where the first output voltage $U_1$ is higher than the output voltage U.

The first output voltage $U_1$ is modulated by the buck circuit 37 to obtain the second voltage $U_2$ and the second output current $I_2$ according to a second preset parameter set sent by the microprocessor 2 in the second time interval $t_2$ of the first duty cycle $T_1$, where the second voltage $U_2$ is lower than the first output voltage $U_1$.

In an embodiment, the first duty cycle $T_1$ further includes a third time interval $t_3$, or a third time interval $t_3$, . . . , and an $N^{th}$ time interval $t_N$, where N is an ordinal number, and $N \geq 3$.

If the first duty cycle $T_1$ further includes the third time interval $t_3$, the boost control circuit 36 is configured to modulate the voltage U of the DC power supply to obtain a third voltage $U_3$ and a third output current $I_3$ according to a third preset parameter set sent by the microprocessor 2 in the third time interval $t_3$ of the first duty cycle $T_1$ in the first time range $T_1'$.

In an embodiment, the buck circuit 37 is configured to further modulate the voltage U of the DC power supply to obtain the first output voltage $U_1$ and the first output current $I_1$ according to the first preset parameter set sent by the microprocessor 2 in the first time interval $t_1$ of the first duty cycle $T_1$ in the first time range $T_1'$. The boost control circuit 36 can be configured to further modulate the output voltage U of the DC power supply to obtain the second output voltage $U_2$ and the second output current $I_2$ according to the second preset parameter set sent by the microprocessor 2 in the second time interval $t_2$ of the second duty cycle $T_2$ in the second time range $T_2'$. The second voltage $U_2$ can be lower than the first target voltage $U_1$, or equal to the voltage U, which is not limited herein.

If the first duty cycle $T_1$ further includes the third time interval $t_3$, the boost control circuit 36 is configured to modulate the voltage U of the DC power supply to obtain the third voltage $U_3$ and the third output current $I_3$ according to the third preset parameter set sent by the microprocessor 2 in the third time interval $t_3$ of the first duty cycle $T_1$ in the first time range $T_1'$. The buck circuit 37 is configured to further modulate the voltage U of the DC power supply to obtain a fourth voltage $U_4$ and a fourth output current $I_4$ according to a fourth preset parameter set sent by the microprocessor 2 in a fourth time interval $t_4$ of the first duty cycle $T_1$ in the first time range $T_1'$, or is configured to further modulate the voltage U of the DC power supply to obtain an $N^{th}$ voltage UN and an $N^{th}$ output current IN according to a $N^{th}$ preset parameter set sent by the microprocessor 2 in an $N^{th}$ time interval ty of the first duty cycle $T_1$ in the first time range $T_1'$, which is not limited herein.

Accordingly, when the first duty cycle $T_1$ further includes the third time interval $t_3$, . . . , and the $N^{th}$ time interval $t_N$, the boost control circuit 36 and the buck circuit 37 can alternately modulate the voltage U of the DC power supply to obtain the third voltage $U_3$, . . . , and the $N^{th}$ voltage UN and the third output current $I_3$, . . . , and the $N^{th}$ output current IN according to the third preset parameter set, . . . , and the $N^{th}$ preset parameter set sent by the microprocessor 2 in the third time interval $t_3$, . . . , and the $N^{th}$ time interval $t_N$ of the first duty cycle $T_1$ in the first time range $T_1'$. In addition, the third voltage $U_3$, . . . , and the $N^{th}$ voltage UN are all higher than the voltage U, while instantaneous values of the third voltage $U_3$, . . . , and the $N^{th}$ voltage UN acquired by different operations of the boost control circuit 36 and the buck circuit 37 are different. Obviously, a waveform of an output current is a regular repetition of an irregular wave.

It should be noted that the unequal instantaneous values of the above-mentioned output current or output voltage are depended on the preset parameter set, which is fundamentally different from a non-predetermined ripple wave generated in general circuits or during voltage modulation.

It should be noted that the first duty cycle $T_1$ includes at least one third time interval $t_3$, or at least one third time interval $t_3$, . . . , and at least one $N^{th}$ time interval $t_N$. That is, the first duty cycle $T_1$ can include multiple third time intervals $t_3$, or multiple third time intervals $t_3$, . . . , and multiple $N^{th}$ time intervals $t_N$. Accordingly, the output voltage varies in different time intervals along with the variation of the preset parameter set. Obviously, the waveform of the output current is a regular repetition of an irregular wave.

A specific power conversion circuit will be described below to illustrate the operating principle of the boost control circuit and the buck circuit in detail, so as to facilitate the understanding of the control method of the power supply control circuit, which can achieve boosting and bucking at different time intervals to suppress an uncontrolled increase in temperature of the electrical heating module.

Figure 22:
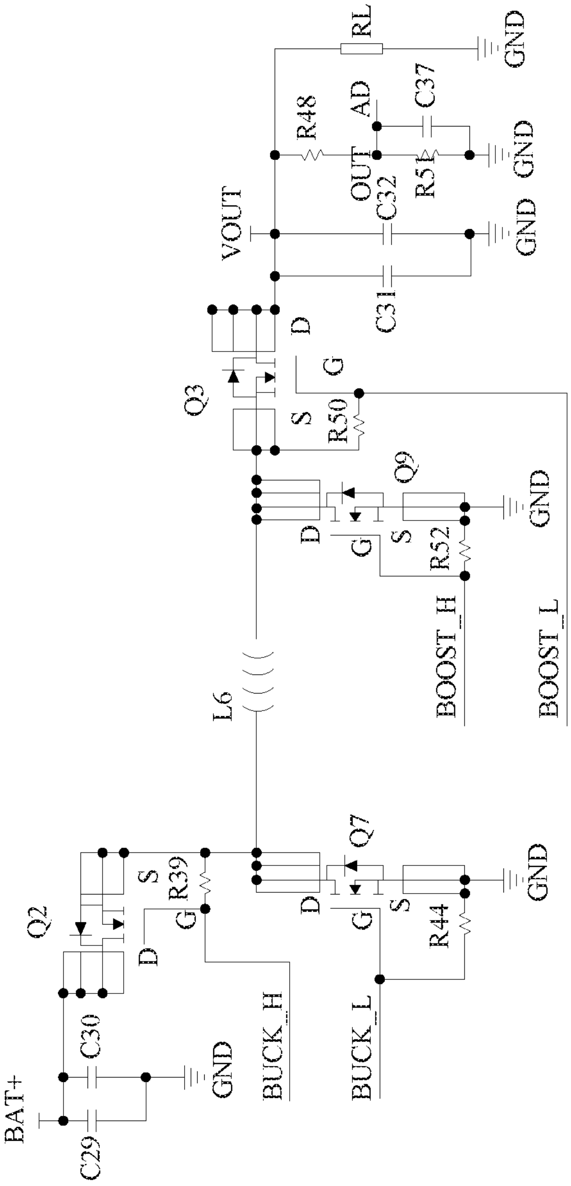
FIG. 22 is a circuit diagram of a power conversion circuit according to an embodiment of the present disclosure.

FIG. 22 is a circuit diagram of the power conversion circuit. The power conversion circuit is actually a full-bridge circuit including a boost mode, a buck mode and a pass-through mode, which is configured to switch to a boost control circuit, a buck circuit, and a pass-through circuit for control. Operating principles of the three circuits will be described below.

(1) Operating Principle of the Boost Control Circuit

The boost control circuit includes $C_{29}$, $C_{30}$, $L_6$, $Q_9$, $Q_3$, $C_{31}$, and $C_{32}$, where $C_{29}$ and $C_{30}$ are an energy storage capacitor and a current renewal capacitor, respectively; $L_6$ is an energy storage inductor; $Q_9$ and $Q_3$ are both a switch component; and $C_{31}$ and $C_{32}$ are a filter capacitor and a loop capacitor, respectively.

During operation of the boost control circuit, $Q_7$ is kept to be off, and $Q_2$ is kept to be on. In a unit cycle, the microprocessor controls $Q_9$ to be on and $Q_3$ to be off. A current flowing out of a supply voltage BAT+ flows through $L_6$ and $Q_9$, to the ground GND to realize charging and energy storage for $L_6$. After the energy storage, the microprocessor controls $Q_9$ to be switched off and $Q_3$ to be switched on, such that energy stored in $L_6$ is released outwards. At this moment, the energy stored in $L_6$ and a voltage on the supply voltage BAT+ are superimposed to form a boost effect. A voltage after superimposition is transmitted to a voltage output terminal Vout to output a boost voltage.

During boosting, an increase in the voltage instantaneous value is proportional to the energy stored in $L_6$.

After executing one unit cycle of the boost control circuit, the power supply control circuit executes another unit cycle of the buck circuit.

(2) Operating Principle of the Buck Circuit

The buck circuit includes $C_{29}$, $C_{30}$, $Q_2$, $Q_7$, $L_6$, $C_{31}$, and $C_{32}$, where $C_{29}$ and $C_{30}$ are an energy storage capacitor and a current renewal capacitor, respectively; $L_6$ is an energy storage inductor; $Q_7$ and $Q_2$ are both a switching component; and $C_{31}$ and $C_{32}$ are a filter capacitor and a loop capacitor, respectively.

During operation of the boost control circuit, $Q_9$ is kept to be off, and $Q_3$ is kept to be on. In a unit cycle, the microprocessor controls $C_{31}$ and $C_{32}$ to be connected to $L_6$, that is, controls $Q_2$ to be switched on and $Q_7$ to be switched off. The supply voltage BAT+ outputs a current to Vout through $Q_2$ and $L_6$ to realize the charging and energy storage for $L_6$. After the energy storage, the microprocessor controls $Q_2$ to be switched off and $Q_7$ to be switched on such that energy stored in $L_6$ is released outwards. At this moment, the voltage of energy stored in $L_6$ is lower than BAT+. A voltage provided by $L_6$ flows through $Q_7$ to the voltage output terminal Vout to output a buck voltage.

During bucking, a decrease in the voltage instantaneous value is proportional to the energy stored in $L_6$.

(3) Operating Principle of the Pass-Through Circuit

The pass-through circuit is capable of transmitting constant unidirectional DC, which is an incidental function of the full-bridge circuit. The microprocessor only needs to control the $Q_7$ and $Q_9$ to be switched off, and $Q_2$ and $Q_3$ to be switched on, a constant unidirectional supply voltage BAT+ can be transmitted to the voltage output terminal Vout, to output a constant unidirectional voltage.

Furthermore, in the circuit diagram shown in FIG. 22, BOOSTH and BOOSTL are a high value and a low value of the boost voltage, respectively. BUCKH and BUCKL are a high value and a low value of the buck voltage. All transistors are N-channel metal-oxide-semiconductor (NMOS) transistors, which are not described herein.

In some embodiments, a preset frequency, preset phase, preset width, and measured effect, as well as a preferred frequency, preferred phase, preferred width, and preferred measured effect are obtained through experimental verification, as shown in Table 2.

TABLE 2

| | Frequency (Hz) | Phase (°) | Width (duty ratio) |
|---|---|---|---|
| Preset | Lower than 1000 | 0-180° | 0-100% |
| Preferred | 25-150 | 12-30° | 5-95% |
| Illustration | Within a preset variation range of frequency, an ideal experience can be achieved. An actual set range of frequency is preferred to 25 Hz-150 | In general, the output voltage/current is in the same phase. A power consumption of product is measured to be reduced by about 8-12% at a | Under a preset power, a duty ratio is regulated properly, which avoids the appearance of deadbands and pass- |

TABLE 2-continued

| Frequency (Hz) | Phase (°) | Width (duty ratio) |
|---|---|---|
| Hz. A service life of an atomizer is measured to be increased by 50-100%. | preferred phase of 12-30°. | through phenomena, and has a power-saving effect. |

It should be noted that when a circuit includes an inductive load or a capacitive load, there is a phase difference between the current and the voltage passing through that load, as shown in the second column of Table 2.

According to Table 2, parameters in the preset parameter set includes the preset frequency, preset phase and preset width (duty ratio) of voltage. The preset frequency is not higher than 1000 Hz. Generally, the preferred frequency range of the electrical heating module is 300 Hz-1000 Hz in a cleaning state (that is, 300 Hz≤f≤1000 Hz) and 2-200 Hz in a low-flow vaping state (that is, 2 Hz≤f≤200 Hz). Preferably, the preferred frequency can be 80-150 Hz (that is, 80 Hz≤f≤150 Hz), or the preferred frequency is 2-100 Hz in a high-flow vaping (that is, 2 Hz≤f≤100 Hz). Preferably, the preferred frequency range is 20-50 Hz, that is, 20 Hz≤f≤50 Hz. It can be seen from the experimental data, the output voltage based on the preferred frequency can increase the service life of an atomizer provided with the electrical heating module by 50% to 100% compared to that of the existing atomizer, that is, the service life is increased by 0.5 to 1 time.

The output voltage has a preset phase range of 0-180° and a preferred phase range of 12-30°. The output voltage based on the preferred phase range can reduce the power consumption of atomizer by 8-12%.

The preset width (duty ratio) is 0-100%, preferably, 5-95%. The output voltage based on the preferred width, can regulate the duty ratio to avoid the appearance of dead zones and pass-through phenomena between the boost control circuit and the buck circuit. Furthermore, electric heat conversion efficiency can be improved and the power consumption of the electrical heating module can be reduced by setting the width within the preferred range.

It can be seen from the operating principles of the boost control circuit and the buck circuit that the voltage variation can be achieved by the boost control circuit, the buck circuit, and the pass-through circuit in different time intervals, so as to provide alternating boosted voltage and current, and bucked voltage and current to the electrical heating module. The electrical heating module can heat according to the output voltage and current of which the instantaneous values are continuously variable, so as to suppress an uncontrolled rise of the temperature of the electrical heating module and make the electrical heating module to be heated evenly, thereby extending a service life of the electrical heating module and improving the use performance of the electrical heating module.

A variation range of the current instantaneous value, also known as variation range of current amplitude or variation range of voltage magnitude, should be not less than 50%, preferably not less than 100%. The variation range of 100% represents that the instantaneous value of a current changes from 0 to a maximum value in a specific direction, forming a unidirectional pulsating current if the current is discontinuous, or a unidirectional pulsating current if the current is continuous. When the variation range is more than 100%, that is, the direction of the current and voltage is changed, and the AC is formed.

Accordingly, the above-mentioned preset parameters include preset frequency, preset phase, and preset width (duty ratio) of the output voltage, and may include variation range of instantaneous value of preset current or voltage, direction variation of current or voltage, and frequency of current change.

It should be noted that, in the cleaning state of the electrical heating module, a working duration of the AC is less than or equal to a time interval threshold. By applying the AC to the electrical heating module and allowing the working duration of the AC within the time interval threshold, the electrical heating module is driven to generate physical oscillation to remove deposits on the surface of the electrical heating module during heating, so as to clean the electrical heating module.

In an embodiment, the time interval threshold may be 1-100 ms. Specifically, a millisecond shock oscillation generated by the electrical heating module can effectively reduce the deposits on the surface of the electrical heating module. For example, when applying the cleaning method of the electrical heating module to the e-cigarette, after each vaping, the heating wire (that is, the electrical heating module) of the e-cigarette generates a millisecond shock oscillation (e.g., mechanical oscillation, thermal oscillation, and magnetic oscillation) to reduce deposition time of deposits, thereby cleaning the heating wire.

In an embodiment, the AC can be applied to the electrical heating module during the normal working duration of the electrical heating module, or after heating of the electrical heating module is finished. For example, after the heating of the electrical heating module is finished, the electrical heating module is driven by modulating the current of the electrical heating module to generate the physical oscillation to remove deposits on the surface of the electrical heating module during heating.

In an embodiment, a heating end time of the electrical heating module can be determined by detecting a heating current in the electrical heating module. If the heating of the electrical heating module is finished, the electrical heating module is driven to generate the physical oscillation.

In an embodiment, if the heating current of the electrical heating module is 0 mA in a first time interval $t_1$, the heating of the electrical heating module is determined to end. For example, the heating current of the electrical heating module is continuously detected, if the heating current of the electrical heating module is 0 mA in the first time interval $t_1$, the heating of the electrical heating module is determined to end.

In an embodiment, a time point after a second time interval $t_2$ when the heating current of the electrical heating module is 0 mA is set as the heating end time. For example, by controlling delay through a software, after a button of the e-cigarette is released for the second time interval $t_2$, the AC is provided to the electrical heating module.

In this embodiment, by applying the AC to the electrical heating module after heating, the electrical heating module is driven to generate physical oscillation to remove deposits on the surface of the electrical heating module during heating. For example, after each vaping of the e-cigarette, the electrical heating module is driven by the AC to generate shock oscillation to reduce deposition time of deposits, thereby shedding the deposits.

In an embodiment, by providing the AC to the electrical heating module, the electrical heating module can be driven to generate mechanical oscillation, thermal oscillation, magnetic oscillation, and so on. For example, by controlling the on and off of a heating power supply or the sudden variation of a heating power, the heating assembly of the electrical heating module is capable of generating thermal expansion and contraction to create micro oscillation, so as to remove the deposits on the surface of the electrical heating module.

In an embodiment, the electrical heating module includes two heating wires, where the two heating wires are arranged opposite to each other. By regulating the direction of the current of the two heating wires, the direction of electric field in one of the two heating wires is alternately the same as or opposite to that in another of the two heating wires in an oscillation cycle. Therefore, the two heating wires are alternately attracted and repelled in one oscillation cycle to drive the electrical heating module to generate mechanical oscillation, so as to remove the deposits on the surface of the electrical heating module.

In an embodiment, the cleaning method of the electrical heating module is used to clean the electrical heating module of the e-cigarette (i.e., atomization core and heating wire) during working, which is performed on the e-cigarette or a control device of the e-cigarette, such as control assembly, control unit, control circuit and control chip. The control unit is taken as an example to implement the cleaning method of the electrical heating module. The control unit is connected to a driving unit. The control unit is configured to control the driving unit to output a corresponding current to drive the electrical heating module to generate physical oscillation, so as to remove the deposits on the surface of the electrical heating module.

In an embodiment, the electrical heating module may be a heating wire, a heating sheet, a heating net, or a heating resistor. The electrical heating module is arranged inside an oil-guiding cotton, that is, the oil-guiding cotton covers the electrical heating module. The oil-guiding cotton can be replaced by ceramic or other oil guiding parts. In an embodiment, the heating sheet covers the oil-guiding cotton. The voltage, the current, the duty cycle of the AC can be regulated. Furthermore, a position of the heating section on the heating assembly and a position of the non-heating section on the heating assembly can be regulated to achieve flexible use.

In an embodiment, the working duration of the AC includes multiple oscillation cycles. The cleaning method of the electrical heating module provided in this embodiment further includes the regulation of the current parameter of the AC in multiple oscillation cycles.

In addition, $R_{51}$, $R_{48}$ and $C_{37}$ shown in FIG. 22 are resistors configured to shunt, and $R_{39}$ and $R_{44}$ are resistors configured to filter, which will not be described in detail as they have no direct relationship with the embodiments of the present disclosure.

Another embodiment of the present disclosure is described below.

Figure 23:
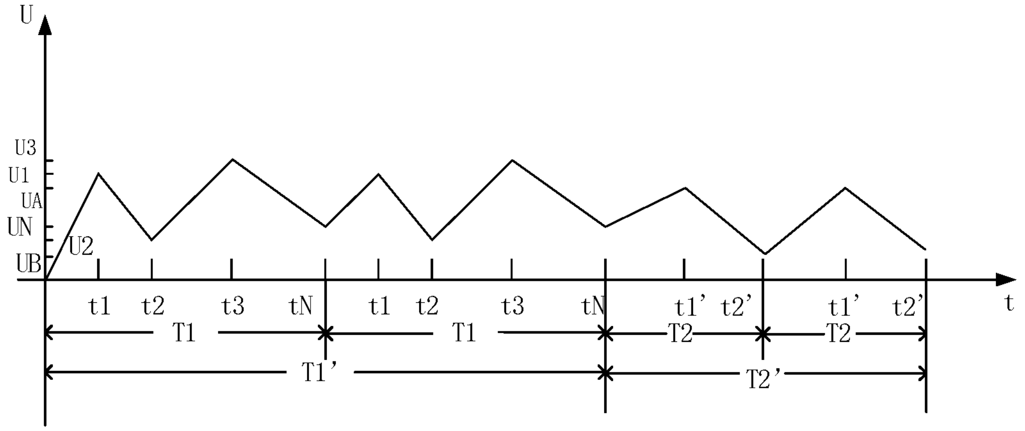
FIG. 23 is a timing diagram of an output voltage of another power supply method according to an embodiment of the present disclosure.

FIG. 23 is a timing diagram of a control method of another power supply control circuit according to an aspect of this embodiment of the disclosure. Based on the control method shown in FIGS. 17-20, the control method further includes the following steps.

The voltage U of the DC power supply is modulated by the boost control circuit to obtain a $1^{st'}$ voltage $U_1'$ and a $1^{st'}$ output current $I_1'$ according to a $1^{st'}$ preset parameter set sent by the microprocessor 2 in a $1^{st'}$ time interval $t_1'$ of a second duty cycle $T_2$ in a second time range $T_2'$.

The $1^{st'}$ voltage $U_1'$ is modulated by the buck circuit to obtain a $2^{nd'}$ voltage $U_2'$ and a $2^{nd'}$ output current $I_2'$ according to a $2^{nd'}$ preset parameter set sent by the microprocessor 2 in a second duty cycle $T_2$, where the $2^{nd'}$ voltage $U_2'$ is lower than the $1^{st'}$ voltage $U_1'$; and the second duty cycle $T_2$ includes at least one first time interval $t_1'$ and at least one $2^{nd'}$ time interval $t_2'$.

It should be noted that the first voltage $U_1'$ and the second voltage $U_2'$ are different from the first output voltage $U_1$ and the second output voltage $U_2$ which are shown in FIGS. 1-4. Obviously, a waveform of the output current in the second time range $T_2'$ is a regular repetition of a regular wave.

The electrical heating module is capable of heating by means of the first output voltage $U_1'$, the first output current $I_1'$, the second output voltage $U_2'$, and the second output current $I_2'$ output from the boost control circuit and the buck circuit.

It should be noted that the first preset parameter set may include a variation range of the $1^{st'}$ output voltage $U_1'$ and a frequency variation of the $1^{st'}$ output voltage $U_1'$. The second preset parameter set may include a variation range of the $2^{nd'}$ output voltage $U_2'$ and a frequency variation of the $2^{nd'}$ output voltage $U_2'$.

It should be noted that in this embodiment, in the control method of the power supply control circuit, the boosting and bucking of voltage are merely repeated in the $1^{st'}$ time interval and the $2^{nd'}$ time interval in the second duty cycle $T_2$ of the second time range $T_2'$. The boosting and bucking of voltage can also be repeated in the first time interval $t_1$ or the second time interval $t_2$ in the first duty cycle $T_1$ of the first time range $T_1'$, which is not limited herein.

In addition, the $1^{st'}$ time interval $t_1'$ can be equal to or different from the second time interval $t_2'$. Moreover, the second duty cycle $T_2$ can include multiple $1^{st'}$ time intervals $t_1'$ and multiple $2^{nd'}$ time intervals $t_2'$.

In an aspect of this embodiment, in the control method of the power supply control circuit, the boosting and bucking of voltage can not only be performed in different time intervals of the first duty cycle $T_1$ in the first time range $T_1'$, but also in different time intervals of the second duty cycle $T_2$ in the second time range $T_2'$. Therefore, the control method of the power supply control circuit can provide more output voltages and output currents that have various instantaneous values to the electrical heating module, which can further inhibit a quick rise of the temperature of the electrical heating module, and enable the electrical heating module to regulate its temperature after heating, thereby further enhancing the use performance of the electrical heating module and prolonging the service life of the electrical heating module. In addition, for a personal vaping device, different flavors of aerosols and non-combustible tobacco can be obtained to satisfy users.

Further, the control method of the power supply control circuit further includes the following contents.

Figure 24:
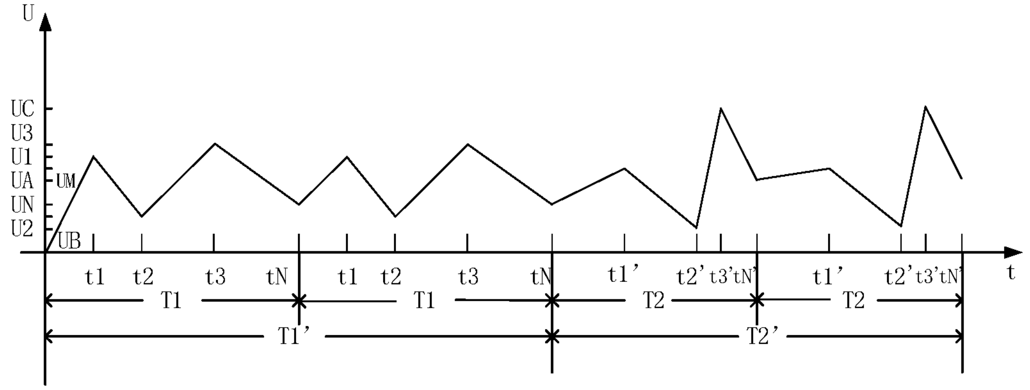
FIG. 24 is a timing diagram of an output voltage of another power supply method according to an embodiment of the present disclosure.

FIG. 24 illustrates a timing diagram of the control method of the power supply control circuit provided in an aspect in this embodiment.

The second duty cycle $T_2$ can further include a 3rd' time interval $t_3'$, or further include a 3rd' time interval $t_3'$, . . . , and an $N^{th}$ time interval $t_{N'}'$, where N' is an ordinal number, and $N' \geq 3$.

If the second duty cycle $T_2$ further includes the 3rd' time interval $t_3$', the boost control circuit is configured to modulate the voltage U to obtain a third voltage and a third output current according to a 3rd' preset parameter set sent by the microprocessor 2 in the $3^{rd'}$ time interval $t_3$' of the second duty cycle $T_2$ in the $2^{nd'}$ time range $T_2$'.

In an embodiment, if the second duty cycle $T_2$ further includes the $3^{rd'}$ time interval $t_3$', . . . , and the $N^{th'}$ time interval ty', the boost control circuit and the buck circuit are configured to alternatively modulate the voltage U to obtain output a $3^{rd'}$ output voltage, . . . , and an $N^{th'}$ output voltage and a $3^{rd'}$ output current, . . . , and an $N^{th'}$ output current according to a $3^{rd'}$ preset parameter set, . . . , and an $N^{th}$ preset parameter set sent by the microprocessor 2 in the third time interval $t_3$', . . . , and the $N^{th}$ time interval ty of the second duty cycle $T_2$ in the $2^{nd'}$ time range $T_2$'.

It should be noted that the third output voltage, . . . , and the $N^{th}$ output voltage are all higher than the voltage U, while instantaneous values of the third output voltage, . . . , and an $N^{th}$ output voltage obtained according to different operations of the boost control circuit and the buck circuit are different. Obviously, a waveform of the output current in the second time range $T_2$' is a regular repetition of an irregular wave. In addition, the second duty cycle $T_2$ may include at least one $3^{rd'}$ time interval $t_3$', or includes at least one $3^{rd'}$ time interval $t_3$', . . . , and one $N^{th'}$ time interval $t_N$'.

It should be noted that the unequal instantaneous values of the above-mentioned output current or output voltage are depended on the preset parameter set, which is fundamentally different from a non-predetermined ripple wave generated in general circuits or during voltage modulation.

The electrical heating module is capable of heating by the third output voltage $U_3$' and the third output current $I_3$', or the third output voltage $U_3$', . . . , and the $N^{th}$ output voltage UN' and the third output current $I_3$', . . . , and the $N^{th}$ output current IN'.

It should be noted that the third preset parameter set may include a variation range of the third voltage $U_3$' and a frequency variation of the third voltage $U_3$'. The $N^{th}$ preset parameter set may include a variation range of the $N^{th}$ voltage UN' and a frequency variation of the $N^{th}$ voltage UN'.

It should be noted that in this embodiment, in the control method of the power supply control circuit, when the boosting and bucking of voltage can not only be performed in the $1^{st'}$ time interval $t_1$', . . . , and the $3^{rd'}$ time interval $t_3$' of the second duty cycle $T_2$ in the $1^{st'}$ time range $T_1$', the boosting and bucking of voltage are also performed in the first time interval $t_1$, . . . , and the 3rd time interval $t_3$ of the first duty cycle $T_1$ in the second time range $T_1$, which is not limited herein. Other implementations can also be included for illustration.

In the above-mentioned embodiment, the boost control circuit and the buck circuit can be alternately operated in a preset sequence in at least one $1^{st'}$ time range $T_1$' and at least one $2^{nd'}$ time range $T_2$'.

In the embodiment shown in FIGS. 17-20, the boost control circuit and the buck circuit can be alternately operated in a preset sequence in at least one $1^{st}$ time interval $t_1$ and at least one $2^{nd}$ time interval $t_2$.

In an embodiment, the boost control circuit and the buck circuit can be alternately operated in a preset sequence in at least one $1^{st}$ time interval $t_1$, at least one $2^{nd}$ time interval $t_2$, and at least one $3^{rd}$ time interval $t_3$.

In an embodiment, the boost control circuit and the buck circuit can be alternately operated in a preset sequence in at least one $1^{st}$ time interval $t_1$, at least one $2^{nd}$ time interval $t_2$, at least one $3^{rd}$ time interval $t_3$, . . . , and at least one $N^{th}$ time interval $t_N$.

In the embodiment shown in FIGS. 23-24, the boost control circuit and the buck circuit can be alternately operated in a preset sequence in at least one $1^{st}$ time interval $t_1$' and at least one $2^{nd}$ time interval $t_2$'.

Further, the boost control circuit and the buck circuit can be alternately operated in a preset sequence in at least one $1^{st'}$ time interval $t_1$', at least one $2^{nd'}$ time interval $t_2$', and least one $3^{rd'}$ time interval $t_3$'.

In an embodiment, the boost control circuit and the buck circuit can be alternately operated in a preset sequence in at least one first time interval $t_1$', at least one $2^{nd'}$ time interval $t_2$', at least one $3^{rd'}$ time interval $t_3$', . . . , and at least one $N^{th'}$ time interval t'.

Figure 25:
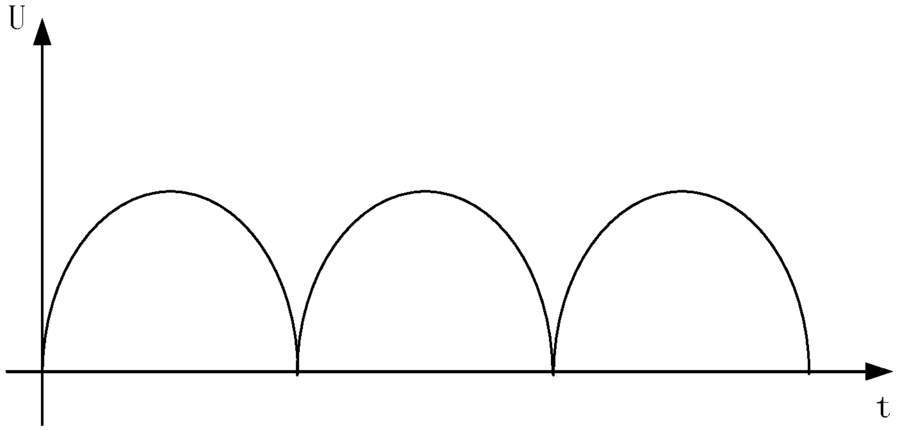
FIG. 25 is a timing diagram of an output voltage of another power supply method according to an embodiment of the present disclosure.
Figure 26:
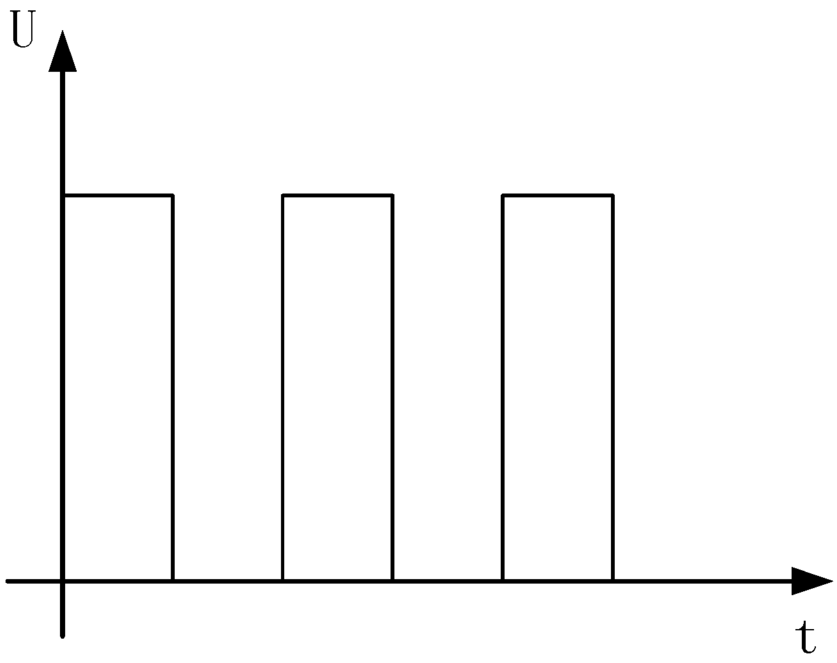
FIG. 26 is a timing diagram of an output voltage of another power supply method according to an embodiment of the present disclosure.
Figure 27:
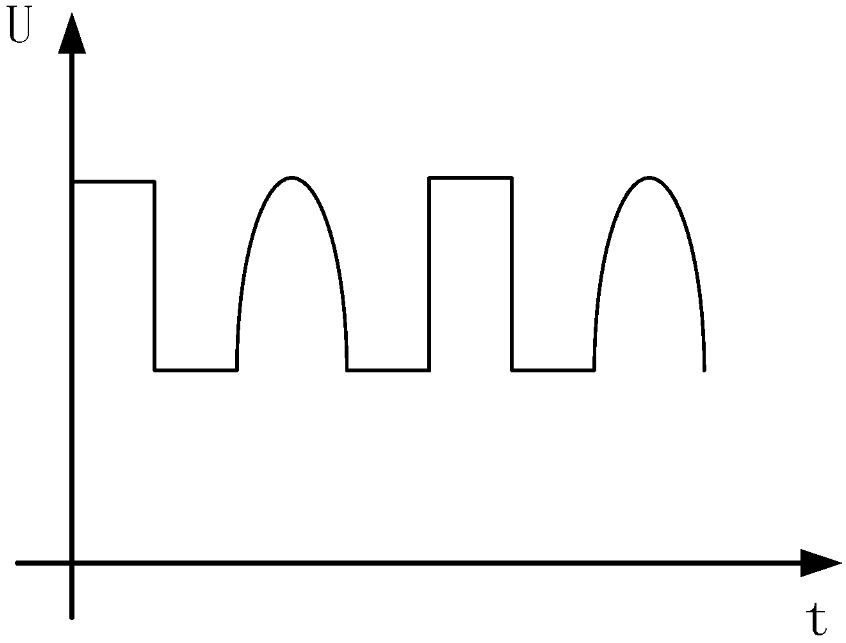
FIG. 27 is a timing diagram of an output voltage of another power supply method according to an embodiment of the present disclosure.
Figure 28:
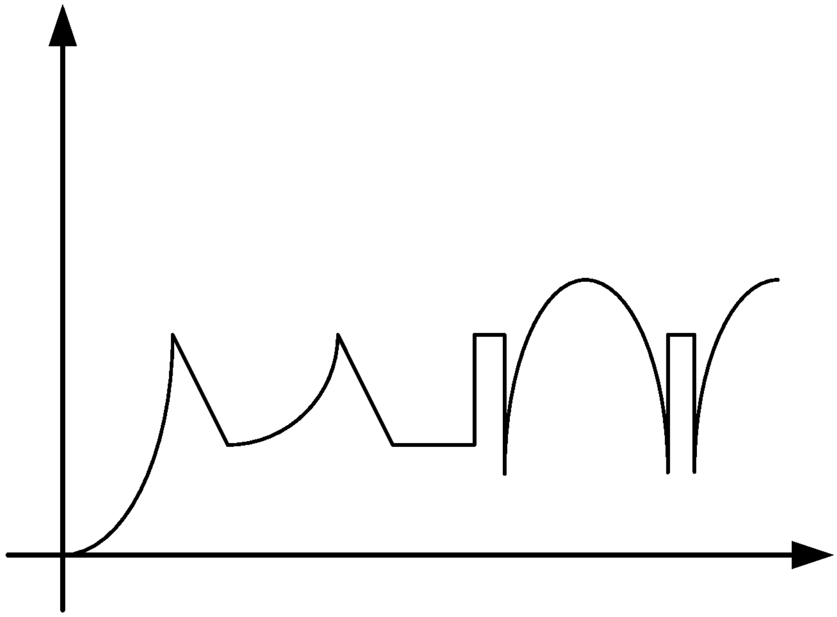
FIG. 28 is a timing diagram of an output voltage of another power supply method according to an embodiment of the present disclosure.

Further, referring to FIGS. 25-28, timing diagrams of a control method of another power supply control circuit according to an embodiment of the disclosure are illustrated. FIG. 25 depicts a continuous wave, presenting regular repetition of a regular wave. FIG. 26 depicts a pulsating wave, presenting regular repetition of a regular wave. FIG. 27 depicts another continuous wave, presenting regular repetition of a regular wave. FIG. 28 depicts a continuous wave, presenting irregular repetition of an irregular wave. In an aspect of this embodiment, the waveform of the output voltage of the electrical heating module is not limited by FIGS. 18, 20, and 23-24, which can also be the waveforms shown in FIGS. 10-13 generated by controlling the boost control circuit and the buck circuit through the microprocessor. The waveform of the output voltage is not limited herein.

An electrical heating device is provided in an embodiment, which includes at least a power supply control circuit.

The power supply control circuit includes a microprocessor and a voltage modulation module.

The control method of the power supply control circuit includes the above-mentioned control methods shown in FIGS. 17-24.

Since the power supply control circuit is able to control the voltage of the DC power supply to obtain different output voltages and output currents in different time intervals, and to heat the electrical heating module containing the heating assembly, a rise of the temperature of the electrical heating module can be suppressed to avoid continuously maintaining a high temperature, since the output voltage is continuously high, and the electrical heating module can be heated evenly, and thus improving the performance of the electrical heating module, reducing the local deposition on the electrical heating module, and improving the service life of the electrical heating module. For the personal vaping device, the restoration degree of e-cigarette oil and tobacco paste, and the taste of heated non-combustible tobacco and atomized aerosol are enhanced.

Figure 29:
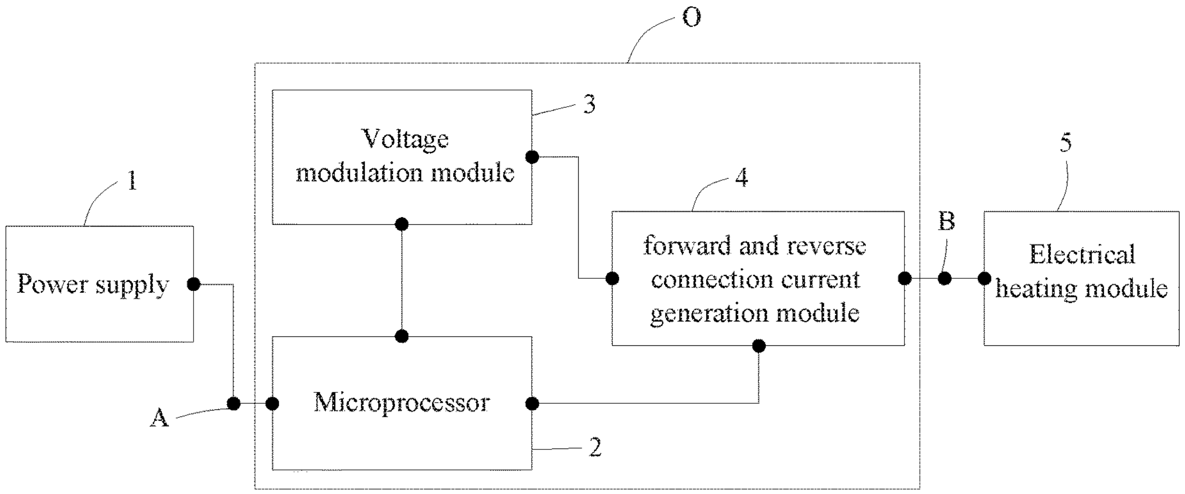
FIG. 29 is a schematic structural diagram of a power supply control circuit according to another embodiment of the present disclosure.

A structure of the power supply control circuit and a control method thereof is described below, as well as the technical solution to reduce a space occupied by the power supply control circuit by respectively integrating and packaging electronic components. FIG. 29 schematically depicts a structure of a power supply control circuit according to an embodiment of the disclosure.

In another aspect of this embodiment, the power supply control circuit is connected to a DC power supply 1 and an electrical heating module 5, respectively. A DC output from the DC power supply is modulated to a supply current having a periodic variation in at least one of direction, instantaneous value and on-state time to drive the electrical heating module 5 to generate heat. The power supply control circuit includes a current input terminal A, a current output terminal B, and a current control module 0. The current control module 0 includes a microprocessor 2, a voltage modulation module 3, and a forward and reverse connection current generation module 4.

The DC power supply 1 is configured to supply power to the microprocessor 2.

The microprocessor 2 is configured to control the voltage modulation module 3 and the forward and reverse connection current generation module 4.

The voltage modulation module 3 is configured to modulate a supply voltage into a first target voltage and a second target voltage, and couple the second target voltage to the forward and reverse connection current generation module 4. The first target voltage is configured to control on and off of the forward and reverse connection current generation module.

The forward and reverse connection current generation module 4 is configured to generate a forward connection current and a reverse connection current according to the second target voltage, and couple the forward connection current and the reverse connection current to the electrical heating module 5 at different time intervals within the same duty cycle of the second target voltage.

The electrical heating module 5 is configured to heat by using a working current. The working current includes the forward connection current and the reverse connection current.

It should be noted that the heating assembly can be a heating resistor, which is not limited herein.

It should be noted that the forward connection current and the reverse connection current are currents having opposite directions generated in different time intervals within the same duty cycle of the second target voltage. The forward connection current and the reverse connection current can be also named as positive current and negative current, respectively. The naming of the current is not limited herein.

In this embodiment of the power supply control circuit, the microprocessor is configured to control the voltage control module and forward and reverse connection current generation module. The voltage modulation module is configured to modulate the supply voltage to the first target voltage and the second target voltage, and couple the second target voltage to the forward and reverse connection current generation module. The forward and reverse connection current generation module is configured to generate the forward connection current and the reverse connection current according to the second target voltage, and couple the forward connection current and the reverse connection current to the electrical heating module at different time intervals within the same duty cycle of the second target voltage. Therefore, the electrical heating module is configured to generate a forward working current and a reverse working current, and alternatively heat by using the forward working current and the reverse working current at different time intervals. In this way, the electrical heating module has a more uniform temperature distribution, further enhancing the taste of the personal vaping device, raising the use performance of the electrical heating module, and prolonging the service life of the electrical heating module.

Figure 30:
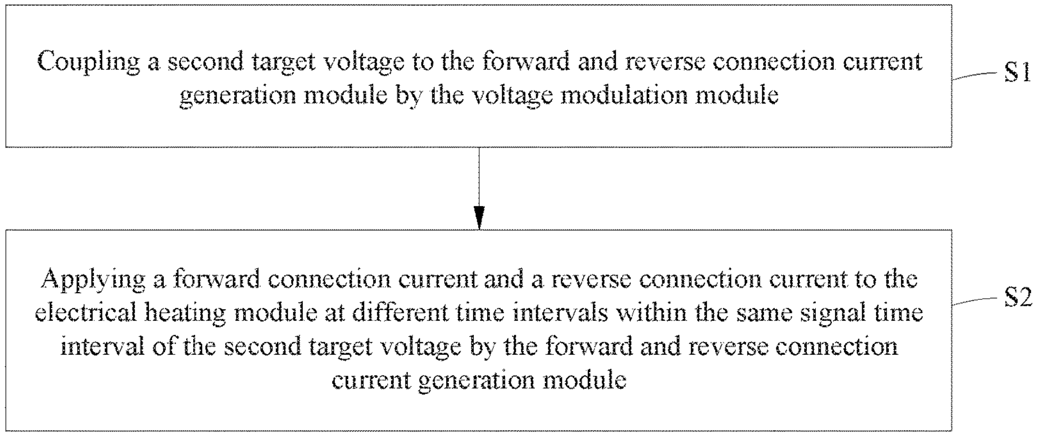
FIG. 30 is a schematic flowchart of a control method of a power supply control circuit according to another embodiment of the present disclosure.

FIG. 30 is a flow chart of a control method of the power supply control circuit shown in FIG. 29.

According to the power supply control circuit of FIG. 29, the control method of this embodiment includes the following steps.

(S1) The second target voltage is coupled to the forward and reverse connection current generation module by the voltage modulation module.

(S2) The forward connection current and the reverse connection current are coupled to the electrical heating module at different time intervals within the same duty cycle of the second target voltage by the forward and reverse connection current generation module.

In this embodiment, the working current includes the forward connection current and the reverse connection current.

In this embodiment, the forward and reverse connection current generation module is capable of generating the forward connection current and the reverse connection current according to the second target voltage, such that the electrical heating module is allowed to alternatively generate the forward working current and the reverse working current to heat. In this way, the electrical heating module is heated evenly, enhancing the use performance and the service life of the electrical heating module.

Figure 31:
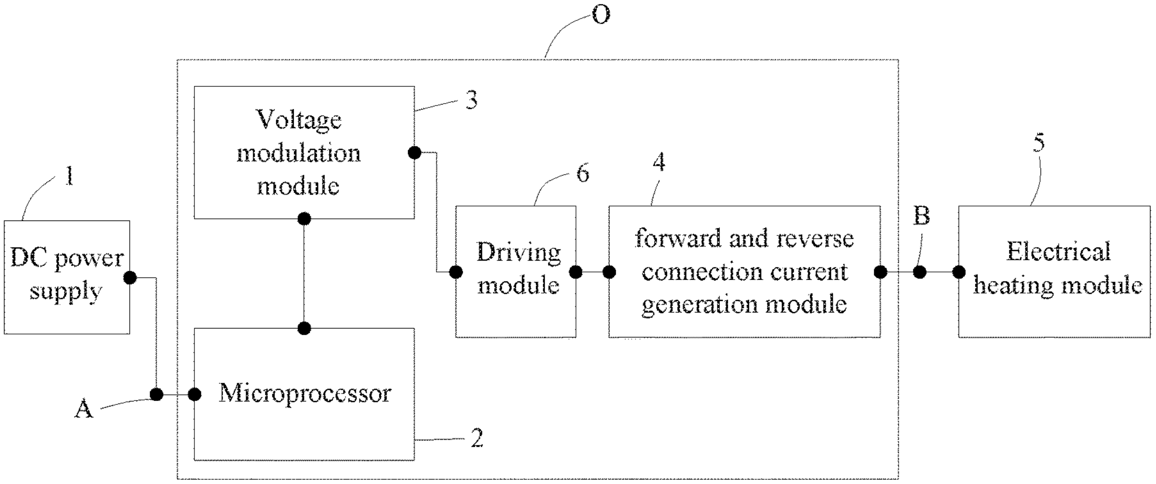
FIG. 31 is a schematic structural diagram of a packaged power supply control circuit according to another embodiment of the present disclosure.

FIG. 31 schematically depicts a structure of the power supply control circuit of FIG. 29, where the power supply control circuit is respectively integrated and packaged.

The power supply control circuit includes a current input terminal A, a current output terminal B, a current control module 0, and an electrical heating module 5. The power supply control circuit is connected to a DC power supply 1 through the current input terminal A. The current control module 0 includes a microprocessor 2, a voltage modulation module 3, a driving module 6, and a forward and reverse connection current generation module 4.

The electronic components of the microprocessor 2, the voltage modulation module 3, the driving module 6 and the forward and reverse connection current generation module 4, and the electrical heating module 5, are respectively integrated and packaged on a circuit board. The driving module 6 is formed by reassembling electronic components to facilitate the packaging of electronic components when assembling the packaging circuit according to the circuit structure shown in FIG. 29. This structural change is configured to reduce a space occupied by electronic components on the power supply control circuit, which has no influence on the function of the power supply control circuit. The electrical heating module 5 shown in FIG. 29 is not included in the power supply control circuit. Whereas, in this embodiment, the electronic components of the electrical heating module 5 are packaged with the power supply control circuit shown in FIG. 29 to reduce their occupied space, which has no influence on the function of the power supply control circuit. The packaging will be described below.

The packaging is performed by in-line packaging or surface mount packaging. The in-line packaging may further include a single in-line packaging, single in-curve packaging, dual in-line packaging, and ball grid array packaging. A packaging material is made of a metal, a plastic, or ceramic. A packaging formation and packaging material is not limited here.

Since the electronic components of the microprocessor, the voltage modulation module, the driving module, the forward and reverse connection current generation module, and the electrical heating module are respectively integrated and packaged on the circuit board, compared with the discrete packaging of each electronic component in each module, the occupied space on the circuit board and in an electronic terminal and the cost are greatly reduced, improving the practicality of the power supply control circuit.

In an embodiment, the microprocessor 2 is configured to control the voltage modulation module 3, the driving module 6, and the forward and reverse connection current generation module 4.

The voltage modulation module 3 is configured to modulate a supply voltage to a first target voltage and a second target voltage, and couple the second target voltage to the driving module. The first target voltage is configured to control on and off of the forward and reverse connection current generation module 4.

The driving module 6 is configured to couple the first target voltage to the forward and reverse connection current generation module 4 to drive the forward and reverse connection current generation module 5 to work.

The forward and reverse connection current generation module 4 is configured to generate a forward connection current and a reverse connection current according to the second target voltage, and couple the forward connection current and the reverse connection current to the electrical heating module 5 at different time intervals within a same duty cycle of the second target voltage.

The electrical heating module 5 is configured to alternatively heat by means of the forward connection current and the reverse connection current.

In an embodiment, the electrical heating module 5 is a heating resistor, which is not limited herein.

In the power supply control circuit provided in this embodiment, the microprocessor is configured to control a current control module consisting of the voltage modulation module, the driving module, and the forward and reverse connection current generation module. The voltage modulation module is configured to modulate the supply voltage to the first target voltage and the second target voltage, and couple the second target voltage to the driving module. The driving module is configured to control couple the first target voltage, which is configured to control on and off of the forward and reverse connection current generation module, to the forward and reverse connection current generation module to drive the forward and reverse connection current generation module to work. The forward and reverse connection current generation module is configured to generate the forward connection current and the reverse connection current according to the second target voltage, and couple the forward connection current and the reverse connection current to the electrical heating module at different time intervals within the same duty cycle of the second target voltage. The electrical heating module is configured to alternatively heat by means of the forward connection current and the reverse connection current. In this way, the electrical heating module has a more uniform temperature distribution, further enhancing the performance of the power supply control circuit and the service life of the electronic terminal having the electrical heating module.

The structure of the power supply control circuit and the packaging forms of the power supply control circuit are described above. The forward and reverse connection current generation module includes:

- a first switch control module and a second switch control module; or
- a third switch control element, a third switch control sub-module, a fourth switch control sub-module, and a transformer.

The forward and reverse connection current generation module including the first switch control module and the second switch control module, and a control method of the power supply control circuit having the forward and reverse connection current generation module will be described below.

Figure 32:
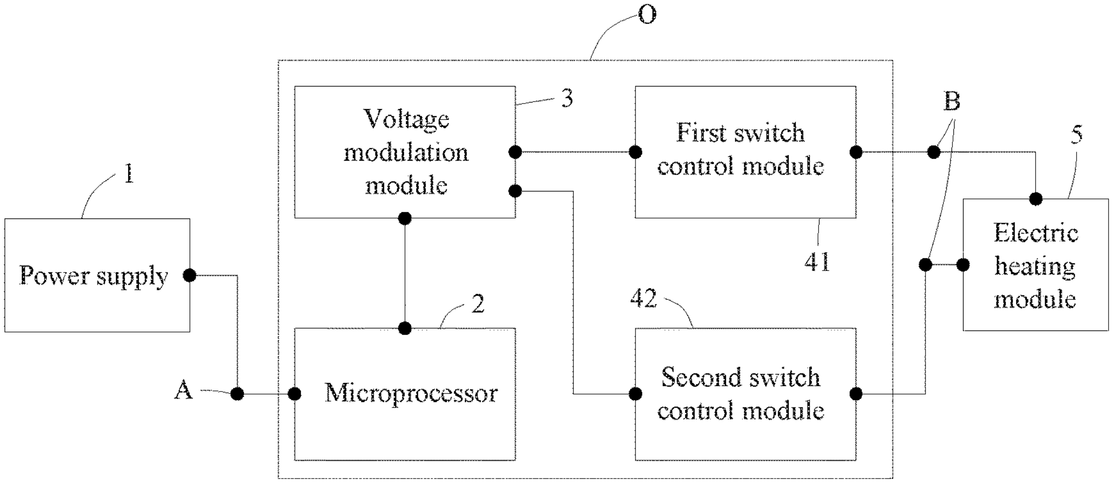
FIG. 32 is a schematic structural diagram of another power supply control circuit according to another embodiment of the present disclosure.

FIG. 32 schematically depicts a structure of a power supply control circuit according to an embodiment of the disclosure, in which the forward and reverse connection current generation module includes the first switch control module and the second switch control module.

As shown in FIG. 32, the power supply control circuit includes a current input terminal A, a current output terminal B, a current control module 0. The current control module 0 includes a microprocessor 2, a voltage modulation module 3, a first switch control module 41, and a second switch control module 42. The power supply control circuit is connected to a DC power supply 1 through the current input terminal A. The power supply control circuit is connected to an electrical heating module 5 through the current output terminal B.

The first switch control module 41 is configured to be switched on in the first time interval, generate a forward connection current according to the second target voltage, and couple the forward connection current to the electrical heating module. The first time interval is a first time interval of the second target voltage within the same duty cycle.

The second switch control module 42 is configured to be switched on in the second time interval, generate a reverse connection current according to the second target voltage, and couple the reverse connection current to the electrical heating module. The second time interval is a second time interval of the second target voltage within the same duty cycle. A sum of the first time interval and the second time interval is not larger than a duration threshold of the same voltage time interval.

Figure 33:
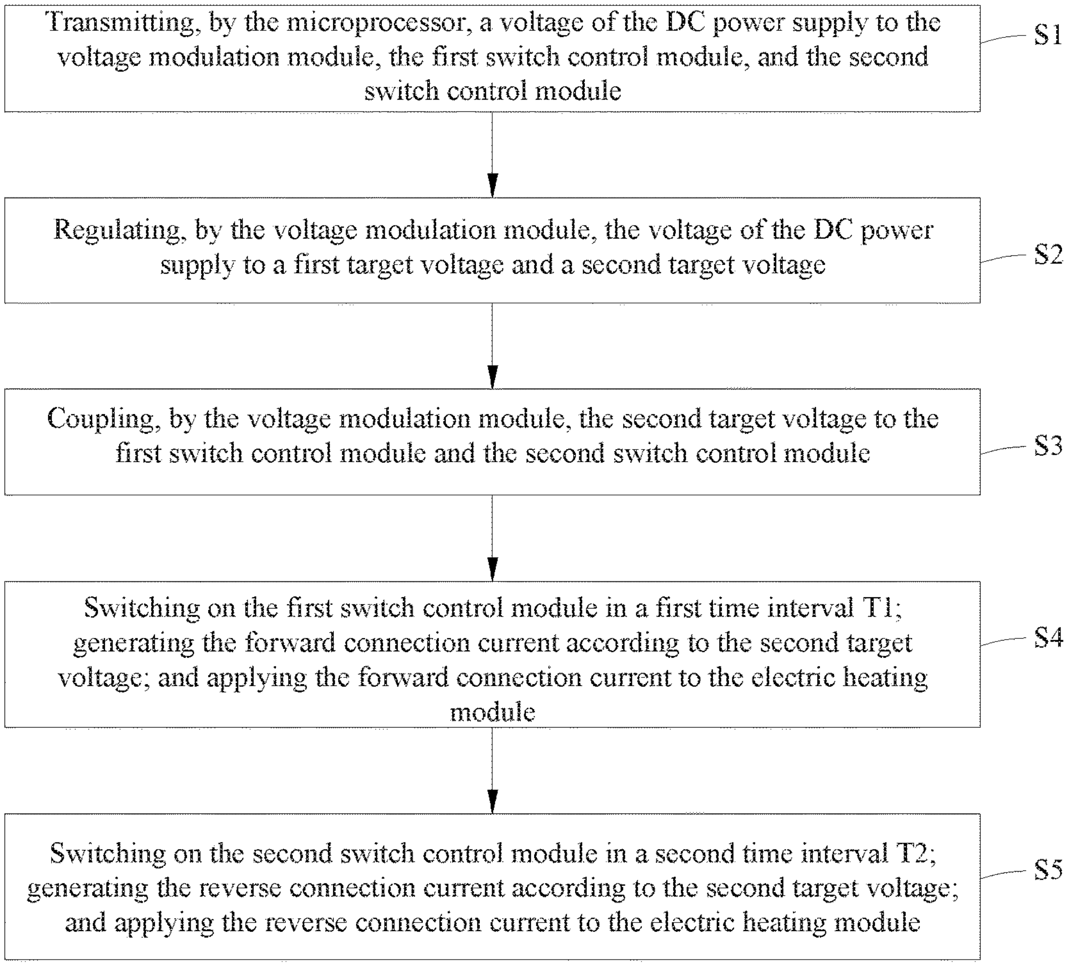
FIG. 33 is a schematic flowchart of another control method of the power supply control circuit according to another embodiment of the present disclosure.

FIG. 33 is a flow chart of a control method of the power supply control circuit.

The control method of the power supply control circuit includes the following steps.

(S1) A voltage of the DC power supply is transmitted to the voltage modulation module, the first switch control module, and the second switch control module by the microprocessor, respectively.

(S2) The voltage of the DC power supply is regulated to the first target voltage and the second target voltage by the voltage modulation module.

(S3) The second target voltage is coupled to the first switch control module and the second switch control module by the voltage modulation module.

(S4) The first switch control module is switched on in the first time interval $T_1$. The forward connection current is generated according to the second target voltage and then is coupled to the electrical heating module by the first switch control module.

(S5) The second switch control module is switched on in the second time interval $T_2$. The reverse connection current is generated according to the second target voltage and then is coupled to the electrical heating module by the second switch control module.

In this embodiment, the first switch control module and the second switch control module is capable of alternatively generating the forward connection current and the reverse connection current in different time intervals of the same duty cycle. Therefore, the electrical heating module is alternatively and evenly heated, improving performance and service life thereof.

Figure 34:
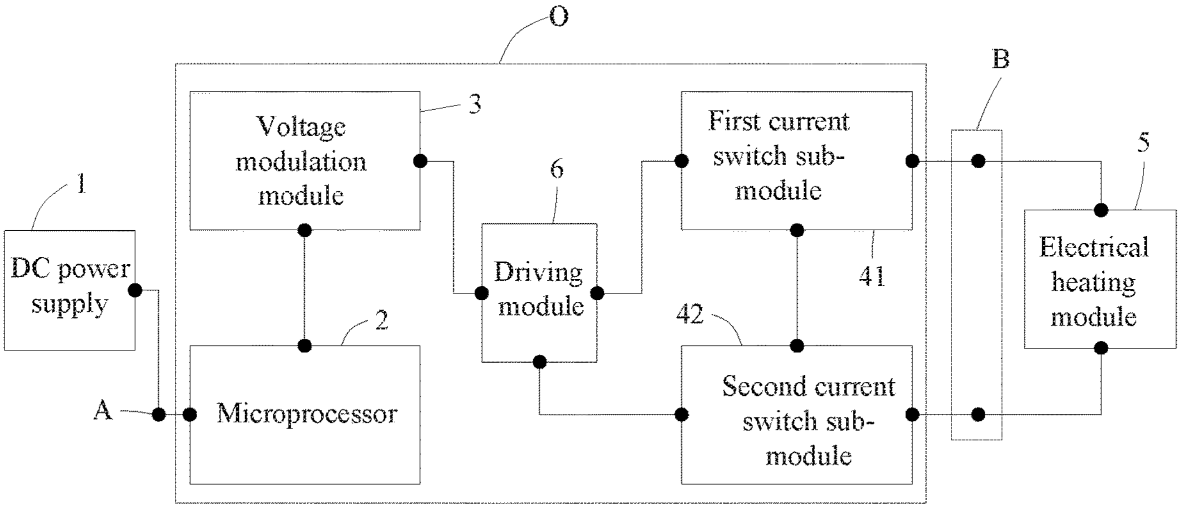
FIG. 34 is a schematic structural diagram of another packaged power supply control circuit according to another embodiment of the present disclosure.

The structure of the power supply control circuit is described above. Referring to FIG. 34, another power supply control circuit being respectively integrated and packaged is schematically depicted below.

A power supply control circuit being respectively integrated and packaged is provided in an embodiment, which includes a current input terminal A, a current output terminal B, a current control module 0, and an electrical heating module 5. The power supply control circuit is connected to a DC power supply 1 through the current input terminal A. The current control module 0 includes a microprocessor 2, a voltage modulation module 3, a driving module 6, a first current switch sub-module 41, and a second current switch sub-module 42.

In this embodiment, the forward and reverse connection current generation module includes the first current switch sub-module 41 and the second current switch sub-module 42.

It should be noted that different time intervals in the above-mentioned embodiment includes the first time interval and the second time interval.

In an embodiment, the first current switch sub-module 41 is configured to be switched on in the first time interval, and couple the forward connection current to the electrical heating module 5.

It should be noted that the first time interval is a first time interval of the second target voltage within the same duty cycle.

The second switch control module 42 is configured to be switched on in the second time interval, generate a reverse connection current, and couple the reverse connection current to the electrical heating module 5.

It should be noted that the second time interval is a second time interval of the second target voltage within the same duty cycle. A sum of the first time interval and the second time interval is not larger than a duration threshold of the same voltage time interval.

Further, the different time intervals can further include a third time interval $t_3$, or further include a third time interval $t_3$, . . . , and a $N^{th}$ time interval $t_N$, where N is an ordinal number. Therefore, the same duty cycle can include the first time interval, the second time interval and the third time interval; or include the first time interval, the second time interval, the third time interval, . . . , and the $N^{th}$ time interval. The number of time intervals in the duty cycle is not limited herein.

Further, the first time interval can be equal to or different from the second time interval. Similarly, all time intervals in the same duty cycle can be equal to or different from each other.

Further, a current magnitude of the forward connection current in the first time interval can be the same to or different from the current magnitude of the reverse connection current in the second time interval.

Further, a waveform of the forward connection current in the first time interval can be the same to or different from that of the reverse connection current in the second time interval.

In an embodiment, the first current switch sub-module 41 may include a first transistor and a second transistor. A second terminal of the first transistor is connected to a first end of the electrical heating module. A first terminal of the second transistor is connected to the ground. A second terminal of the second transistor is connected to a second end of the electrical heating module.

The second current switch sub-module 42 may include a third transistor and a fourth transistor. A second terminal of the third transistor is connected to the other end of the electrical heating module. A first terminal of the fourth transistor is connected to the ground. A second terminal of the fourth transistor is connected to one end of the electrical heating module.

Further, the driving module 6 includes a first driving element and a second driving element. A first terminal of the first driving element is connected to a third terminal of the first transistor. A second terminal of the first driving element is connected to the ground. A third terminal of the first driving element is connected to the microprocessor.

A first terminal of the second driving element is connected to a third terminal of the third transistor. A second terminal of the second driving element is connected to the ground. A third terminal of the second driving element is connected to the microprocessor.

Further, the voltage modulation module 3 may include a boost control circuit and a power conversion circuit.

The boost control circuit is configured to boost the supply voltage to obtain the first target voltage, and transmit the first target voltage to the first current switch sub-module and the second current switch sub-module. One end of the boost control circuit is connected to a third terminal of the second transistor and a third terminal of the fourth transistor, respectively, and the other end of the boost control circuit is connected to the DC power supply.

The power conversion circuit is configured to modulate the supply voltage to obtain the second target voltage. One end of the power conversion circuit is connected to the first terminal of the first transistor and the first terminal of the third transistor, respectively, and the other end of the power conversion circuit is connected to the DC power supply.

The first transistor, the second transistor, the third transistor and the fourth transistor are field-effect transistors or triodes, which are not limited herein.

The first driving element and the second driving element are field-effect transistors or triodes, which are not limited herein.

In an embodiment, the first transistor, the second transistor, the third transistor, and the fourth transistor of the forward and reverse connection current generation module can be integratedly packaged, which can reduce space occupied on the circuit board and in an electronic terminal and the production cost, and improve the practicality of the power supply control circuit. It should be noted that the first current switch sub-module and the second current switch sub-module both can include more transistors, and the number of the transistor of the first current switch sub-module can be the same to or different from that of the second current switch sub-module. Providing more transistors is able to divide a high-power voltage to reduce a burden on each transistor, extending the service life of each transistor.

In addition, the first driving element and the second driving element of the driving module are integratedly packaged, such that the driving module is solely packaged. Compared with packaging each driving element, this integrated packaging of the driving module reduces space occupied on the circuit board and in an electronic terminal, and improves the practicality of the power supply control circuit. It should be noted that the number of the driving elements (such as field-effect transistor or triode) can be more than two, which is not limited herein. Providing more derive elements is able to divide a high-power voltage to reduce a burden on each transistor, extending the service life of each transistor.

In an embodiment, the first transistor, the second transistor, the third transistor and the fourth transistor are all field-effect transistors. The first terminals of the first transistor, the second transistor, the third transistor, and the fourth transistor are all source electrodes. The second terminals of the first transistor, the second transistor, the third transistor, and the fourth transistor are all drain electrodes. The third terminals of the first transistor, the second transistor, the third transistor, and the fourth transistor are all grid electrodes. That is, the first transistor and the third transistor can be positive-channel metal oxide semiconductor (PMOS) transistors, and the second transistor and the fourth transistor can be N-channel metal-oxide-semiconductor (NMOS) transistors.

In an embodiment, the number of the PMOS transistor can be three or more. The number of the NMOS transistor can be three or more. The number of the PMOS transistor can be the same to or different from the number of the NMOS transistor, which is not limited herein.

In an embodiment, when the first transistor and the third transistor both are NMOS transistors, the second transistor and the fourth transistor are PMOS transistors.

In an embodiment, the first transistor, the second transistor, the third transistor and the fourth transistor are all triodes. The first transistor and the third transistor can be negative-positive-negative (NPN) triodes, and the second transistor and the fourth transistor can be PNP triodes. Meanwhile, in an embodiment, the first transistor and the third transistor can be PNP triodes, and the second transistor and the fourth transistor can be NPN triodes, which is not limited herein.

It should be noted that the first terminals of the first driving element and the second driving element can be collecting terminals, the second terminals of the first driving element and the second driving element can be emitting electrodes, and the third terminals of the first driving element and the second driving element can be base electrodes. That is, the first driving element and the second driving element can all be NPN triodes or PNP triodes, which is not limited here.

In an embodiment, one of the first driving element and the second driving element is PNP type triode, and another thereof is NPN type triode.

In an embodiment, the first driving element and the second driving element are field-effect transistors, which is not limited herein.

In an embodiment, the power conversion circuit is a full-bridge power conversion circuit, a half-bridge power conversion circuit, or a push-pull power conversion circuit, which is not limited herein.

Figure 35:
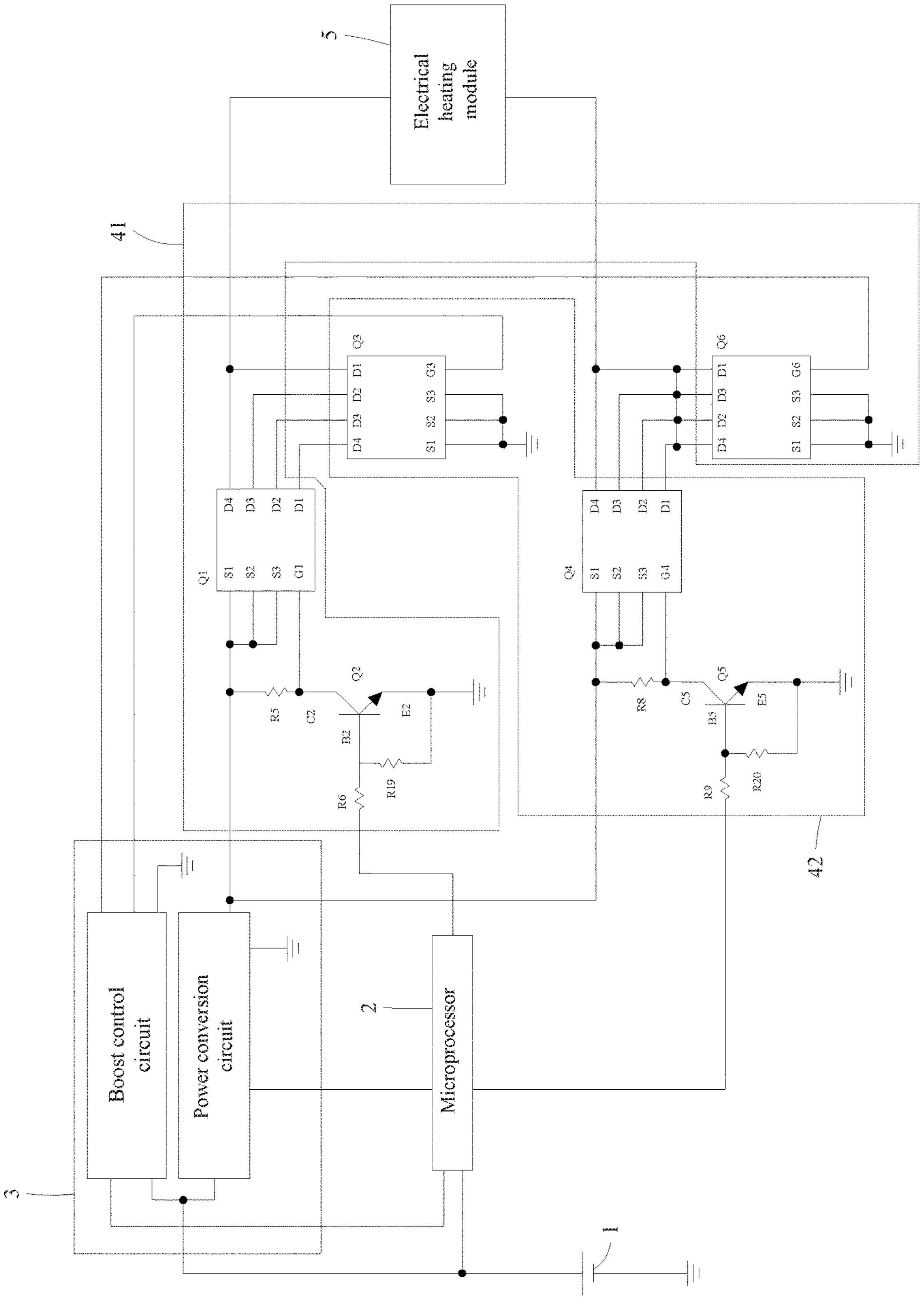
FIG. 35 is an equivalent schematic diagram of another power supply control circuit according to another embodiment of the present invention.

The power supply control circuit being integratedly packaged is schematically depicted above. FIG. 35 is an equivalent diagram of a power supply control circuit, which is a detailed depiction of the structure of the power supply control circuit shown in FIG. 32 in the electronic-component-level.

It should be noted that the electrical heating module in this embodiment is a heating resistor R of an atomizer.

Specifically, in the power supply control circuit provided in this embodiment, the first switch control module 41 includes a first PMOS transistor $Q_1$, a second NMOS transistor $Q_6$, and a first triode $Q_2$. A drain electrode $D_1$ of the first PMOS transistor $Q_1$ is connected to a first end of the heating resistor. A source electrode $S_6$ of the second NMOS transistor $Q_6$ is connected to the ground. A drain electrode $D_6$ of the second NMOS transistor $Q_6$ is connected to the other end of the heating resistor. A collecting terminal $C_2$ of the first triode $Q_2$ is connected to a grid electrode $G_1$ of the first PMOS transistor $Q_1$. An emitting terminal $E_2$ of the first triode $Q_2$ is connected to the ground. A base terminal $B_2$ of the first triode $Q_2$ is connected to the microprocessor.

The second switch control module 42 includes a third PMOS transistor $Q_4$, a fourth NMOS transistor $Q_3$, and a second triode $Q_5$. A drain electrode $D_4$ of the third PMOS transistor $Q_4$ is connected to the other end of the heating resistor. A source electrode $S_3$ of the fourth NMOS transistor $Q_3$ is connected to the ground. A drain electrode $D_3$ of the fourth NMOS transistor $Q_3$ is connected to one end of the heating resistor. A collecting terminal $C_5$ of the second triode $Q_5$ is connected to a grid electrode $G_4$ of the third PMOS transistor $Q_4$. An emitting terminal $E_5$ of the second triode $Q_5$ is connected to the ground. A base terminal $B_5$ of the second triode $Q_5$ is connected to the microprocessor.

The voltage modulation module 2 of the power supply control circuit includes a boost control circuit and a power conversion circuit. The boost control circuit is configured to boost the supply voltage to obtain the first target voltage, and respectively transmit the first target voltage to the first switch control module and the second switch control module. One end of the boost control circuit is connected to the grid electrode $G_6$ of the second NMOS transistor $Q_6$ and the grid electrode $G_3$ of the fourth NMOS transistor $Q_3$, and the other end of the boost control circuit is connected to the DC power supply.

The power conversion circuit is configured to modulate the supply voltage to obtain the second target voltage. One end of the power conversion circuit is connected to the source electrode $S_1$ of the first PMOS transistor $Q_1$ and the source electrode $S_4$ of the third NMOS transistor $Q_4$, and the other end of the power conversion circuit is connected to the DC power supply.

It should be noted that in another aspect of the embodiment, the first triode $Q_2$ and the second triode $Q_5$ are both NPN triode or PNP triode, or one of them is NPN triode and the other is PNP triode.

Referring to FIG. 35, each of the source electrodes of a first NMOS transistor, a second NMOS transistor, a third NMOS transistor, and a fourth NMOS transistor has three pins, each of the drain electrodes of the first NMOS transistor, the second NMOS transistor, the third NMOS transistor, and the fourth NMOS transistor has four pins. The number of pin of the source electrode and the drain electrode of each NMOS transistor is not limited, which can be one, two, or more. Providing multiple pins facilitates heat dissipation of the NMOS transistor, and protects the NMOS transistor from burning out. In addition, the $R_5$, $R_6$, $R_9$, $R_{19}$, and $R_{20}$ are auxiliary resistors for each triode and MOS transistor, which are not described herein.

Another embodiment of the power supply control circuit of the present application of the power supply control circuit is detailed described above.

Figure 36:
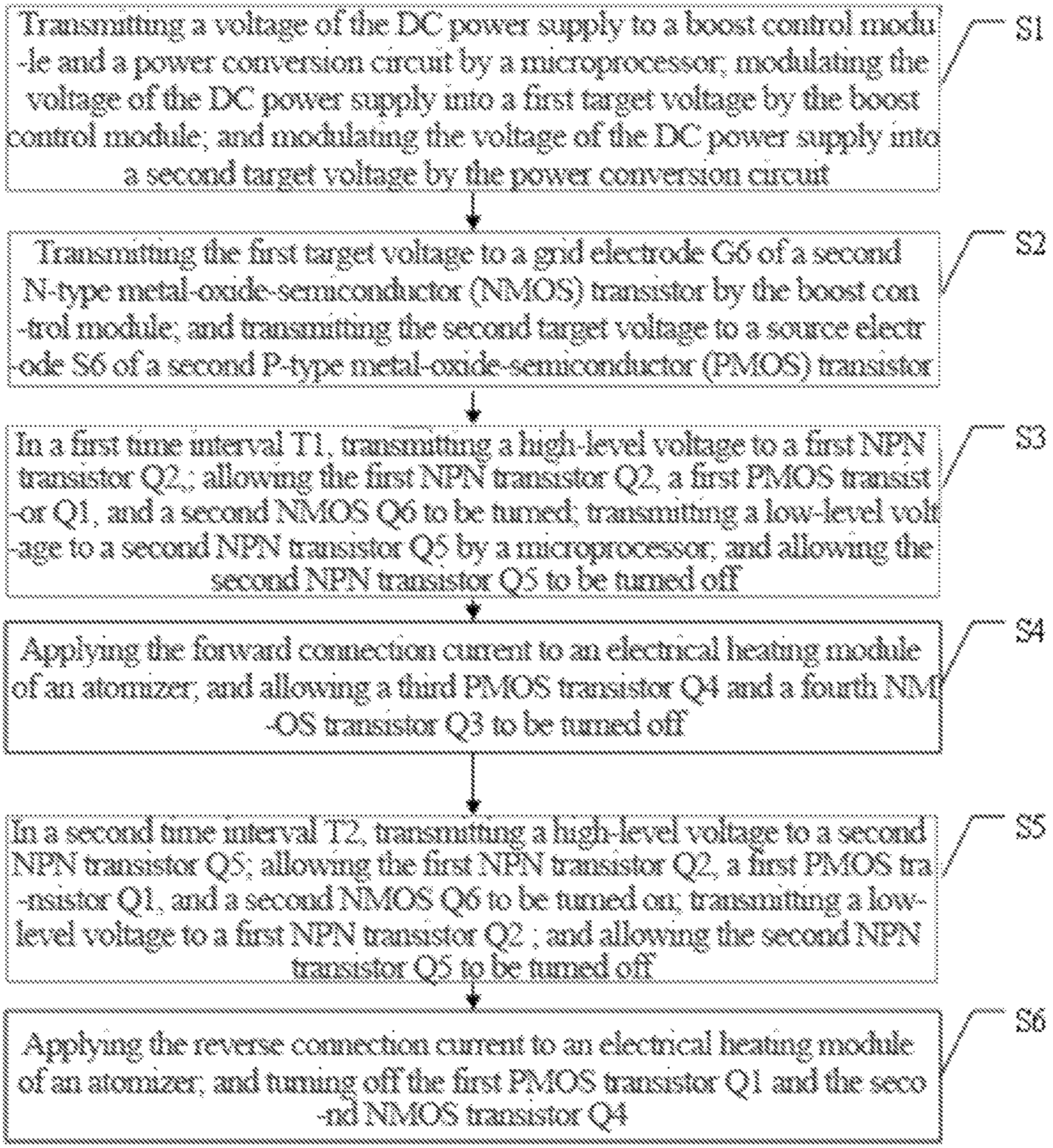
FIG. 36 is a schematic flowchart of another control method of the power supply control circuit according to another embodiment of the present disclosure.
Figure 37:
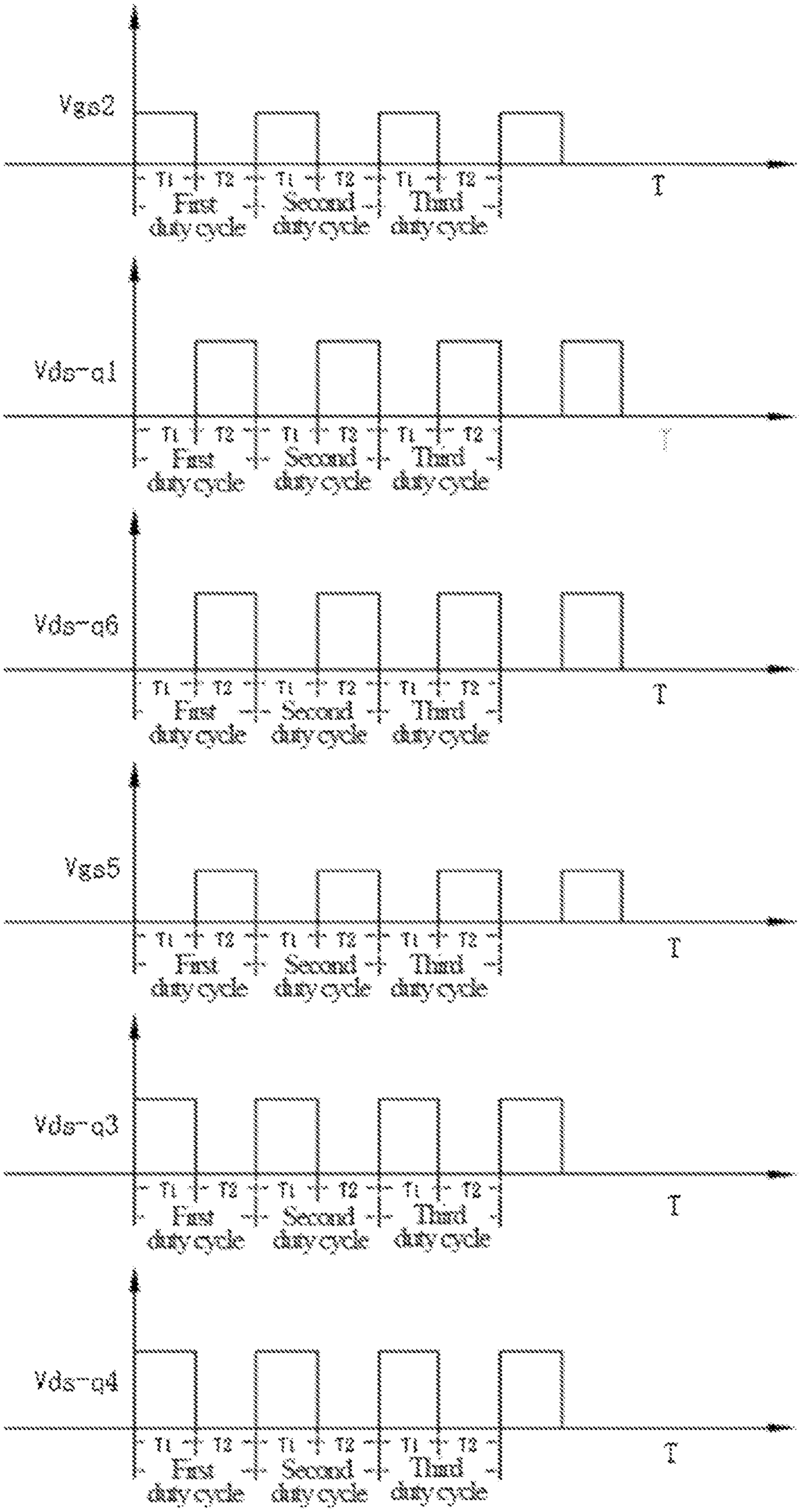
FIG. 37 is a timing diagram of a control method of a power supply control circuit according to another embodiment of the present disclosure.

FIG. 36 is a flow chart of a control method of the power supply control circuit. FIG. 37 is a timing diagram of the control method of the power supply control circuit according to an embodiment of the disclosure.

It should be noted that FIG. 37 illustrates timing diagrams of the control methods of the first NPN triode $Q_2$, the first PMOS transistor $Q_1$, the second NMOS transistor $Q_6$, the second NPN type triode $Q_5$, the third PMOS transistor $Q_4$, and the fourth NMOS transistor $Q_3$ from top to bottom, where the horizontal axis indicates a duration of the duty cycle, and the vertical axis indicates a voltage amplitude.

The control method of the power supply control circuit provided in this embodiment is performed through the following steps.

(S1) A voltage of the DC power supply is transmitted to the boost control circuit and the power conversion circuit by the microprocessor, respectively. The voltage of the DC power supply is regulated by the boost control circuit to the first target voltage. The voltage of the DC power supply is regulated to the second target voltage by the power conversion circuit.

A voltage threshold of the first target voltage is the same as or different from that of the second target voltage.

(S2) The first target voltage is transmitted to the grid electrode $G_6$ of the second NMOS transistor $Q_6$ and the grid electrode $G_3$ of the fourth NMOS transistor $Q_3$ through the boost control circuit. The second target voltage is transmitted to the source electrode of the first PMOS transistor $Q_1$ and the source electrode of the third PMOS transistor $Q_3$ by the power conversion circuit.

(S3) In the first time interval $T_1$, a high-level voltage is transmitted to the base terminal $B_2$ of the first NPN triode $Q_2$ by the microprocessor. At the same time, a low-level voltage is transmitted to the base terminal $B_5$ of the second NPN triode $Q_5$ by the microprocessor. In this way, the first NPN triode $Q_2$ is switched on, the first PMOS transistor $Q_1$ and the second NMOS transistor $Q_6$ are switched on, and at the same time the second NPN triode $Q_5$ is switched off.

(S4) A forward connection current is coupled to the heating resistor, and the third PMOS transistor $Q_4$ and the fourth NMOS transistor $Q_3$ are switched off.

(S5) In the second duty cycle $T_2$, a high-level voltage is transmitted to the base terminal $B_5$ of the second NPN triode $Q_5$ by the microprocessor. Meanwhile, a low-level voltage is transmitted to the first NPN triode $Q_2$ by the microprocessor. In this case, the second NPN triode $Q_5$ is switched on, the third PMOS transistor $Q_4$ and the fourth NMOS transistor $Q_3$ are switched on, and at the same time the first NPN type triode $Q_2$ is switched off.

(S6) A reverse connection current is coupled to the heating resistor, and at the same time the first PMOS transistor $Q_1$ and the second PMOS $Q_4$ are switched off.

It should be noted that in the same duty cycle, the first time interval can be equal to or different from the second time interval.

Furthermore, in the same duty cycle of the second target voltage, multiple forward connection currents and multiple reverse connection currents can be generated.

In addition, in the same duty cycle, a magnitude of the forward connection current can be the same to or different from that of reverse connection current.

Steps (S1)-(S7) are repeatedly executed. Since the power supply control circuit can generate the forward connection current and the reverse connection current through the forward and reverse connection current generation module, the heating resistor can be alternatively heated. In this way, the heating resistor can be heated evenly, which enhances the use performance of the heating resistor and the atomizer, improves the taste of personal vaping device and prolongs the service life of the atomizer provided with the heating resistor.

In the embodiments of this application, since the power supply control circuit can generate the forward connection current and the reverse connection current by alternatively switching on and off the first NPN triode $Q_2$ and the second NPN triode $Q_5$, the electrical heating module can be heated alternatively and evenly, which improves the use performance of the electrical heating module and prolongs the duration of the electrical heating module.

In an embodiment, a specific packaging solution of another power supply control circuit is described blow.

Figure 38:
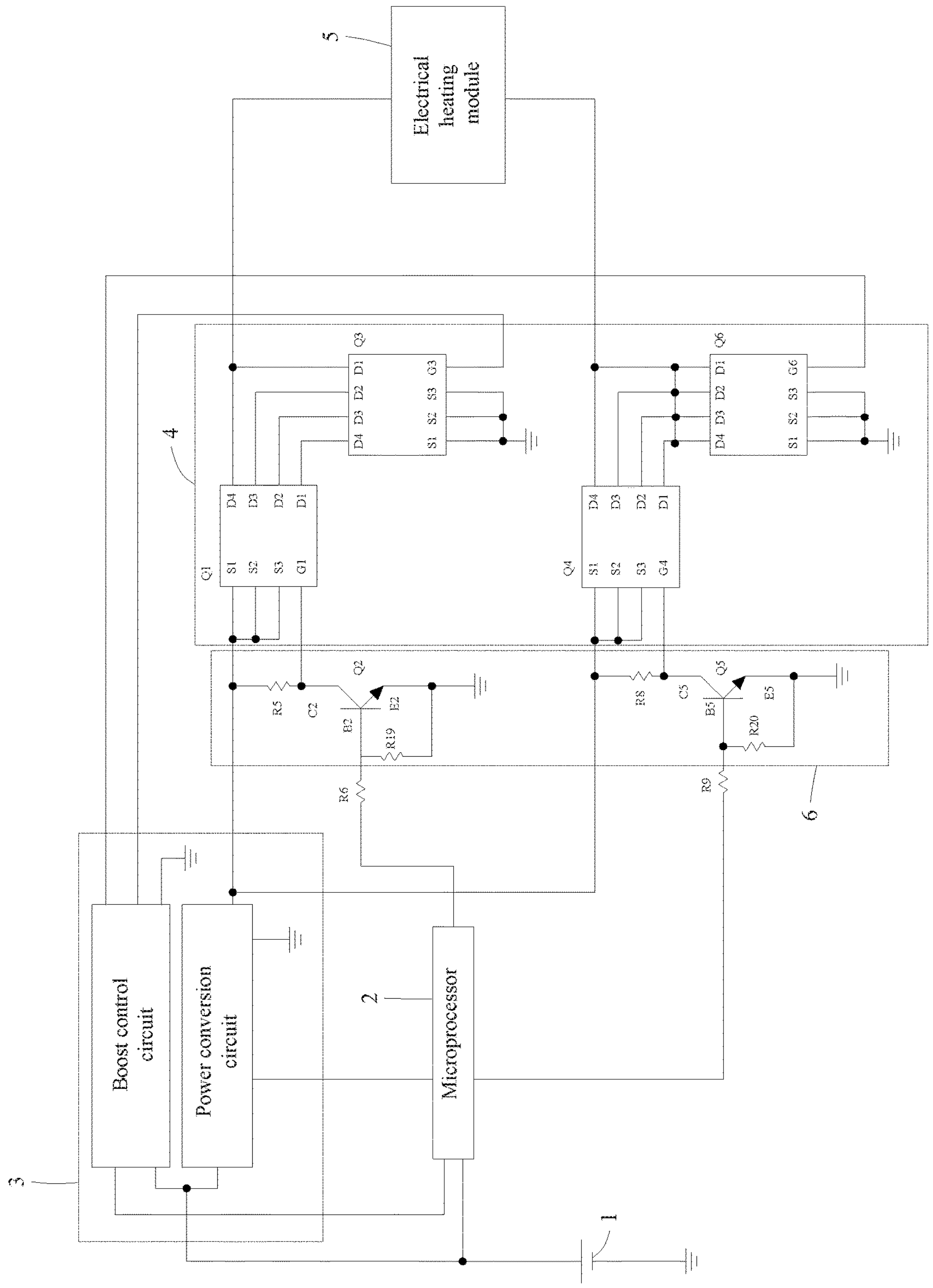
FIG. 38 is a schematic structural diagram of another packaged power supply control circuit according to another embodiment of the present disclosure.

FIG. 38 is an equivalent diagram of this power supply control circuit illustrating the specific packaging solution.

Referring to FIG. 38, the power supply control circuit is provided in an embodiment, which includes a current input terminal A, a current output terminal B, a current control module 0, and an electrical heating module 5. The current control module 0 includes a microprocessor 2, a voltage modulation module 3, a driving module 6, and a forward and reverse connection current generation module 4. The power supply control circuit is connected to a DC power supply 1 through the current input terminal A. Referring to FIG. 38, the voltage modulation module 3, the driving module 6, and the forward and reverse connection current generation module 4 are marked with dashed boxes. Each module is packaged independently according to different spatial arrangements.

In this embodiment, the first current switch sub-module of the power supply control circuit includes a first PMOS transistor $Q_1$ and a second NMOS transistor $Q_6$. A drain electrode $D_1$ of the first PMOS transistor $Q_1$ is connected to one end of the electrical heating module. A source electrode $S_6$ of the second NMOS transistor $Q_6$ is connected to the ground. A drain electrode $D_6$ of the second NMOS transistor $Q_6$ is connected to a second end of the electrical heating module.

The second current switch sub-module of the power supply control circuit includes a third PMOS transistor $Q_4$ and a fourth NMOS transistor $Q_3$. A drain electrode $D_4$ of the third PMOS transistor $Q_4$ is connected to the other end of the electrical heating module. A source electrode $S_3$ of the fourth NMOS transistor $Q_3$ is connected to the ground. A drain electrode $D_3$ of the fourth NMOS transistor $Q_3$ is connected to one end of the electrical heating module.

The driving module 6 includes a first triode $Q_2$ and a second triode $Q_5$. A collecting terminal $C_2$ of the first triode $Q_2$ is connected to a grid electrode $G_1$ of the first PMOS transistor $Q_1$. An emitting terminal $E_2$ of the first triode $Q_2$ is connected to the ground. A base terminal $B_2$ of the first triode $Q_2$ is connected to the microprocessor. A collecting electrode $C_5$ of the second triode $Q_5$ is connected to a grid electrode $G_4$ of the third PMOS transistor $Q_4$. An emitting terminal $E_5$ of the second triode $Q_5$ is connected to the ground. A base terminal $B_5$ of the second triode $Q_5$ is connected to the microprocessor.

The voltage modulation module 3 includes a boost control circuit and a power conversion circuit. The boost control circuit is configured to boost the supply voltage to obtain the first target voltage, and transmit the first target voltage to the first current switch sub-module and the second current switch sub-module, respectively. One end of the boost control circuit is connected to the grid electrode $G_6$ of the second NMOS transistor $Q_6$ and a grid electrode $G_3$ of the fourth NMOS transistor $Q_3$, and the other end of the boost control circuit is connected to the DC power supply.

The power conversion circuit is configured to modulate the supply voltage to obtain the second target voltage. One end of the power conversion circuit is connected to a source electrode $S_1$ of the first PMOS transistor $Q_1$ and a source electrode $S_4$ of the third NMOS transistor $Q_4$, and the other end of the power conversion circuit is connected to the DC power supply.

It should be noted that the first triode $Q_2$ and the second first triode $Q_5$ are both NPN triode or both PNP triode, or one of them is NPN triode and the other is PNP triode.

Referring to FIG. 38, although the source electrodes of a first NMOS transistor, a second NMOS transistor, a third NMOS transistor, and a fourth NMOS transistor all include three pins, the drain electrodes of the first NMOS transistor, the second NMOS transistor, the third NMOS transistor, and the fourth NMOS transistor all include four pins. The number of pin of the source electrode and that of the drain electrode of each NMOS transistor is not limited, which can be one, two, or more. Providing multiple pins facilitates heat dissipation of the NMOS transistor and protects the NMOS transistor from burning out.

In addition, as shown in FIG. 38, $R_5$, $R_6$, $R_8$ and $R_9$ are driving resistors, and $R_{19}$ and $R_{20}$ are ground resistors, which are not described herein.

The microprocessor 2 is configured to control the first triode $Q_2$ and the second triode $Q_5$ of the driving module 6 to alternatively switch on and off through the first target voltage output by the voltage modulation module 3, so as to enable the first current switch sub-module (the first PMOS transistor $Q_1$ and the second NMOS transistor $Q_6$) of the forward and reverse connection current generation module 4 to be switched on at the first time interval in the same duty cycle of the second target voltage, and to generate a forward connection current according to the second target voltage. At this time, the second current switch sub-module (the third PMOS transistor $Q_4$ and the fourth NMOS transistor $Q_3$) is switched off. Then the second current switch sub-module (the third PMOS transistor $Q_4$ and the fourth NMOS transistor $Q_3$) is switched on at the second time interval in the same duty cycle of the second target voltage, and to generate a reverse connection current according to the second target voltage. At this time, the first current switch sub-module (the first PMOS transistor $Q_1$ and the second NMOS transistor $Q_6$) is switched off. Consequently, the forward connection current and the reverse connection current are alternatively provided to the electrical heating module at different time intervals, which prolongs the service life of the electrical heating module and electronic terminal, reduces the production cost, and improves the practicality of the power supply control circuit. Since each module of the power supply control circuit is integratedly packaged independently, the space occupied of electronic components is reduced, realizing the miniaturization of electronic terminals, and improving the practicality of the power supply control circuit and electronic terminals.

Figure 39:
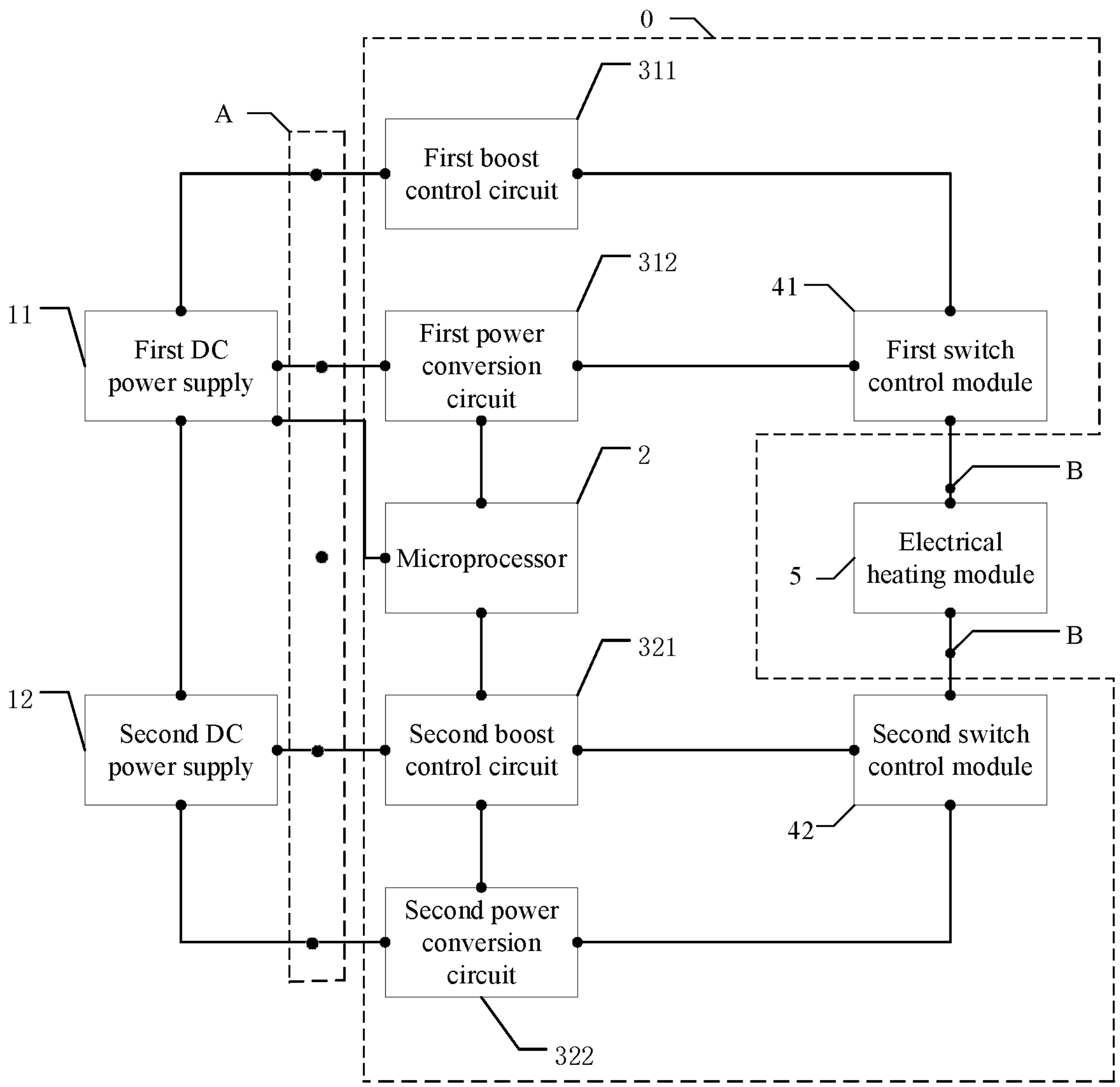
FIG. 39 is a schematic structural diagram of another power supply control circuit according to another embodiment of the present disclosure.

The specific packaging solution of the above-mentioned power supply control circuit is described above. Referring to FIG. 39, the power supply control circuit adopting a dual-DC power supplying method is schematically depicted below. This structure diagram describes a structure change of the power supply control circuit shown in FIG. 32 when the dual-DC power supplying method is adopted.

In this embodiment, compared with the power supply control circuit shown in FIG. 32, further, the power supply includes a first DC power supply 11 and a second DC power supply 12. A negative electrode of the first DC power supply 11 is connected to a negative electrode of the second DC power supply 12, and the negative electrodes of the first DC power supply and the second DC power supply are both connected to the ground. And the first DC power supply and the second DC power supply are both connected to the voltage modulation module. Accordingly, the first DC power supply is configured to provide a forward voltage and a forward connection current. The second DC power supply is configured to provide a reverse voltage and a reverse connection current.

It should be noted that the "forward connection current" and the "reverse connection current" are two currents having exactly opposite amplitude directions, which can be forward current and reverse current, or not, and merely refer to two currents having exactly opposite amplitude directions. Similarly, the "forward connection voltage" and the "reverse connection voltage" can be forward voltage and reverse voltage, or not, and merely refer to two voltages having exactly opposite amplitude directions.

In this embodiment, the voltage modulation module may include a first boost control circuit 311, a first power conversion circuit 312, a second boost control circuit 321, and a second power conversion circuit 322.

The first boost control circuit 311 is configured to boost a first power voltage to obtain the first target voltage, and transmit the first target voltage to the first switch control module 41. One end of the first boost control circuit 311 is connected to the first switch control module 41, and the other end of the first boost control circuit 311 is connected to the first DC power supply 11.

The first power conversion circuit 312 is configured to modulate the first power voltage to obtain the second target voltage. One end of the first power conversion circuit is connected to the first switch control module 41, and the other end of the first power conversion circuit is connected to the first DC power supply 11.

The second boost control circuit 321 is configured to boost a second supply voltage to obtain the first target voltage, and transmit the first target voltage to the second switch control module 42. One end of the second boost control circuit 321 is connected to the second switch control module 42, and the other end of the boost control circuit 321 is connected to the second DC power supply 12.

The second power conversion circuit 322 is configured to modulate the second supply voltage to obtain the second target voltage. One end of the second power conversion circuit 322 is connected to the second switch control module 42, and the other end of the second power conversion circuit 322 is connected to the second DC power supply 12.

The first boost control circuit 311, the first power conversion circuit 312, the second boost control circuit 321, and the second power conversion circuit 322 are controlled by the microprocessor 2, respectively. Therefore, the forward connection current is provided to the electrical heating module 5 at the first time interval, and the reverse connection current is provided to the electrical heating module 5 at the second time interval.

Regarding a power supply control circuit in another aspect of an embodiment of that present application, the microprocessor is configured to control the current control module consisting of the first boost control circuit, the first power conversion circuit, the second boost control circuit, and the second power conversion circuit. The first boost control circuit boosts the first power voltage to obtain the first target voltage. At the same time, the first power conversion circuit modulates the first power voltage to obtain the second target voltage that is transmitted to the first switch control module at the first time interval of the same duty cycle of the second target voltage. Meanwhile, the second switch control module is switched off. The first switch control module transmits the forward connection current to the electrical heating module. Otherwise, the second boost control circuit boosts the second supply voltage to obtain the first target voltage. Meanwhile, the second power conversion circuit modulates the second supply voltage to obtain the second target voltage that is transmitted to the second switch control module at the second time interval of the same duty cycle of the second target voltage. At this time, the first switch control module is switched off. The second switch control module transmits the second target voltage to the electrical heating module such that the electrical heating module is heated evenly by receiving the forward connection current and the reverse connection current in different duty cycles, and thus enhancing the use performance and service life of the electrical heating module.

Described above is the power supply control circuit adopting a dual-DC power supplying method in another aspect of the embodiment of the present application. A control method of the power supply control circuit in another aspect of the embodiment of the present application will be described below.

Figure 40:
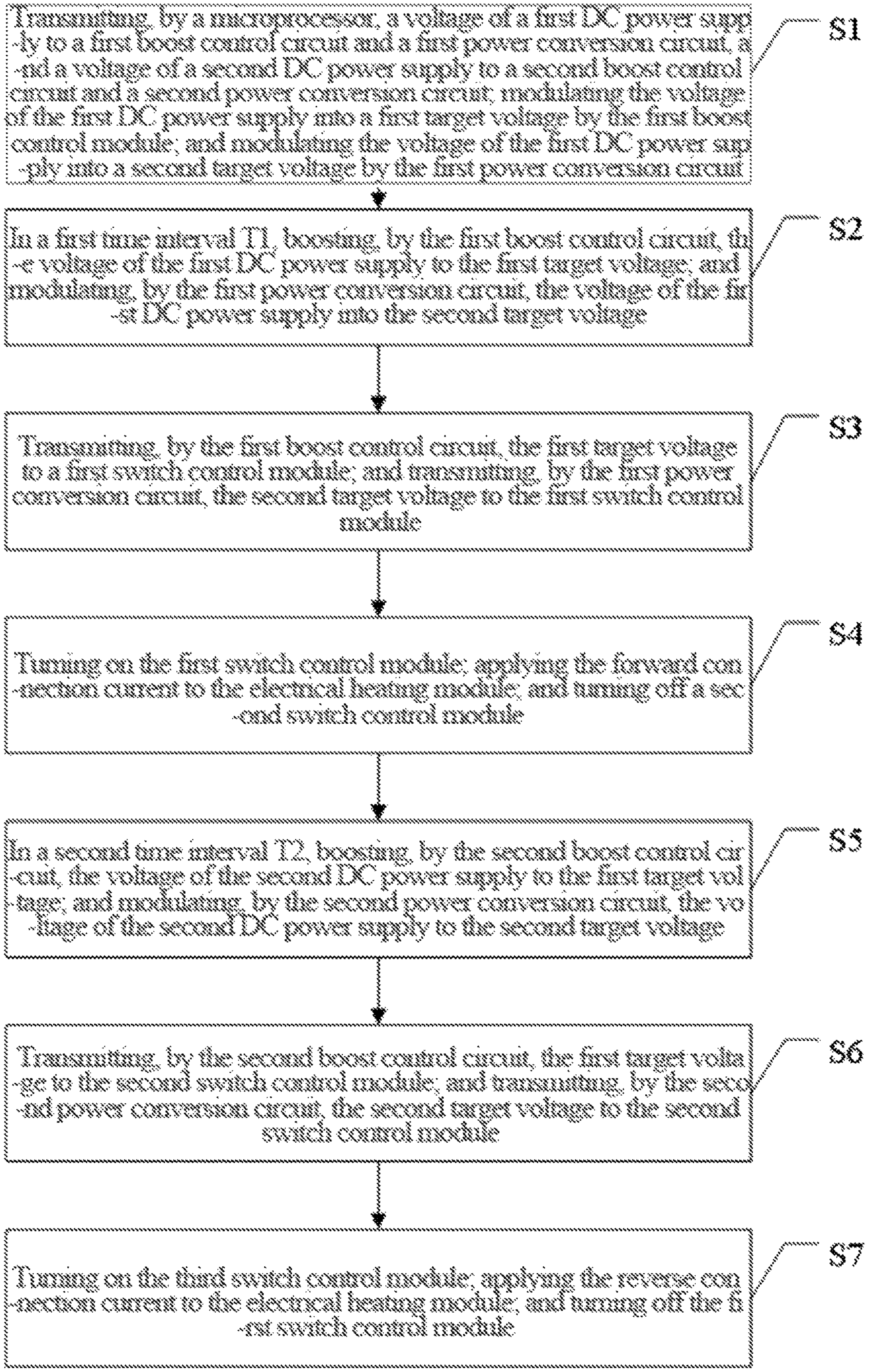
FIG. 40 is a schematic flowchart of another control method of a power supply control circuit according to an embodiment of the present disclosure.

FIG. 40 is a flow chart of the control method of the power supply control circuit.

Further, the control method of the power supply control circuit provided in this embodiment includes the following steps.

(S1) The first power voltage is transmitted to the first boost control circuit and the first power conversion circuit by the microprocessor. The second power voltage is transmitted to the second boost control circuit and the second power conversion circuit by the microprocessor.

(S2) In the first duty cycle $T_1$, the first power voltage is boosted to the first target voltage by the first boost control circuit, and the first power voltage is modulated to the second target voltage by the first power conversion circuit.

In this embodiment, a voltage threshold of the first target voltage is equal to or different from that of the second target voltage.

(S3) The first target voltage is transmitted to the first switch control module by the first boost control circuit. The second target voltage is transmitted to the first switch control module by the first power conversion circuit.

(S4) The first switch control module is switched on. The forward connection current is coupled to the electrical heating module, and the second switch control module is switched off.

(S5) In the second time interval $T_2$, the voltage of the second DC power supply is boosted to the first target voltage by the second boost control circuit, and is modulated to the second target voltage by the first power conversion circuit.

(S6) The first target voltage is transmitted to the second switch control module by the second boost control circuit. The second target voltage is transmitted to the second switch control module by the second power conversion circuit.

(S7) The second switch control module is switched on. The reverse connection current is coupled to the electrical heating module, and at the same time the first switch control module is switched off.

It should be noted that in the same duty cycle, the first duty cycle can be equal to or different from the second duty cycle.

Furthermore, in the same duty cycle of the second target voltage, multiple forward connection currents and reverse connection currents can be generated, which is not limited here.

In addition, in the same duty cycle, a magnitude of the forward connection current can be equal to or different from that of reverse connection current, which is not limited here.

The power supply control circuit can provide the forward voltage to the first power conversion circuit through the voltage of the first DC power supply, and generate the forward connection current at the first time interval of the same duty cycle of the second target voltage. The voltage of the second provides the reverse voltage to the second power conversion circuit and generates the reverse connection current at the second time interval of the same duty cycle of the second target voltage. In consequence, the electrical heating module is heated alternatively and evenly, which improves the use performance of the electrical heating module and prolongs the service life of the electrical heating module.

Figure 41:
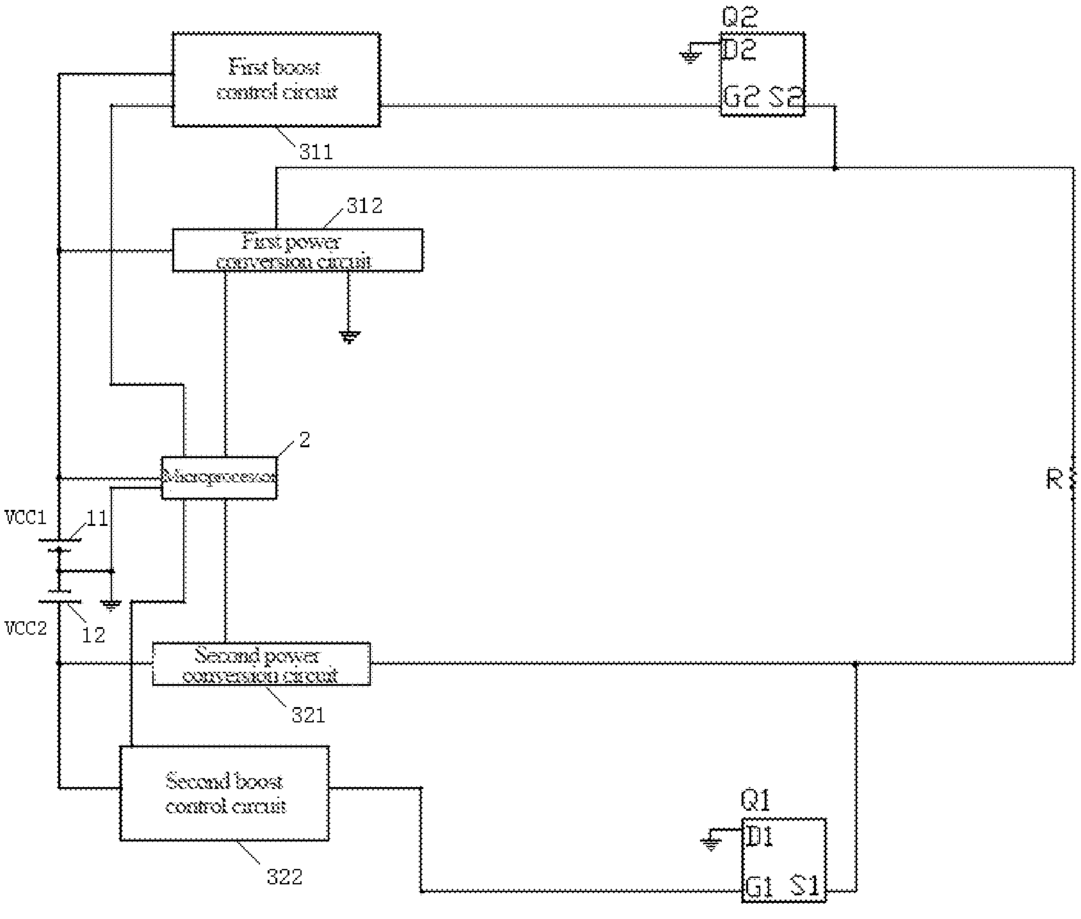
FIG. 41 is an equivalent schematic diagram of another power supply control circuit according to another embodiment of the present disclosure.

Referring to FIG. 41, an equivalent schematic diagram of the power supply control circuit using dual power supplies in another aspect of the embodiment. The above power supply control circuit shown in FIG. 39 is further described in an electronic-component level.

It should be noted that the electrical heating module is the heating resistor R of an atomizer.

The first switch control module may include a first DC power supply $VCC_1$ and a first transistor $Q_1$.

The first DC power supply is configured to provide a power voltage to the first boost control circuit at the first duty cycle.

A first terminal of the first transistor $Q_1$ is connected to the ground. A second terminal of the first transistor $Q_1$ is connected to the other end of the electrical heating module. A third terminal of the first transistor $Q_1$ is connected to an end of the first boost control circuit.

The second switch control module includes a second DC power supply $VCC_2$ and a second transistor $Q_2$.

The second DC power supply is configured to provide a second power voltage to the second boost control circuit at the second time interval.

A first terminal of the second transistor $Q_2$ is connected to the ground. A second terminal of the second transistor $Q_2$ is connected to the other end of the electrical heating module. A third terminal of the second transistor $Q_2$ is connected to an end of the second boost control circuit.

The first transistor $Q_1$ and the second transistor $Q_2$ are field-effect transistors or triodes, which is not limited herein.

In an embodiment, the first transistor $Q_1$ and the second transistor $Q_2$ are both field-effect transistors.

Further, when the first transistor $Q_1$ and the second transistor $Q_2$ are both field-effect transistors, the first transistor $Q_1$ and the second transistor $Q_2$ can be positive channel metal oxide (PMOS) semiconductor transistors or negative channel metal oxide (NMOS) semiconductor transistors, which are not limited here.

It should be noted that, as shown in FIG. 41, the electrical heating module is a heating resistor R.

In an embodiment, when the first transistor $Q_1$ and the second transistor $Q_2$ are both PMOS transistors, a drain electrode $D_1$ of the first transistor $Q_1$ and a drain electrode $D_2$ of the second transistor $Q_2$ are both connected to the ground. A source electrode $S_1$ of the second transistor $Q_1$ is connected to one end of the heating resistor R, and a source electrode $S_2$ of the first transistor $Q_2$ is connected to the other end of the heating resistor R.

On the contrary, when the first transistor $Q_1$ and the second transistor $Q_2$ are both NMOS transistors, the source electrode $S_1$ of the first transistor $Q_1$ and the source electrode $S_2$ of the second transistor $Q_2$ are both connected to the ground. The drain electrode $D_2$ of the second transistor $Q_2$ is connected to one end of the heating resistor R, and the drain electrode $D_1$ of the first transistor $Q_1$ is connected to the other end of the heating resistor R.

When the first transistor $Q_1$ and the second transistor $Q_2$ are both triodes, the first transistor $Q_1$ and the second transistor $Q_2$ are selected from the group consisting of NPN type triode and PNP type triode.

Further, the number of transistor in the first switch control module may be one, two, or more. The number of transistor in the second switch control module may be one, two or more.

It should be noted that the power conversion circuit is a full-bridge power conversion circuit, a half-bridge power conversion circuit, or a push-pull power conversion circuit, which is not limited here.

Figure 42:
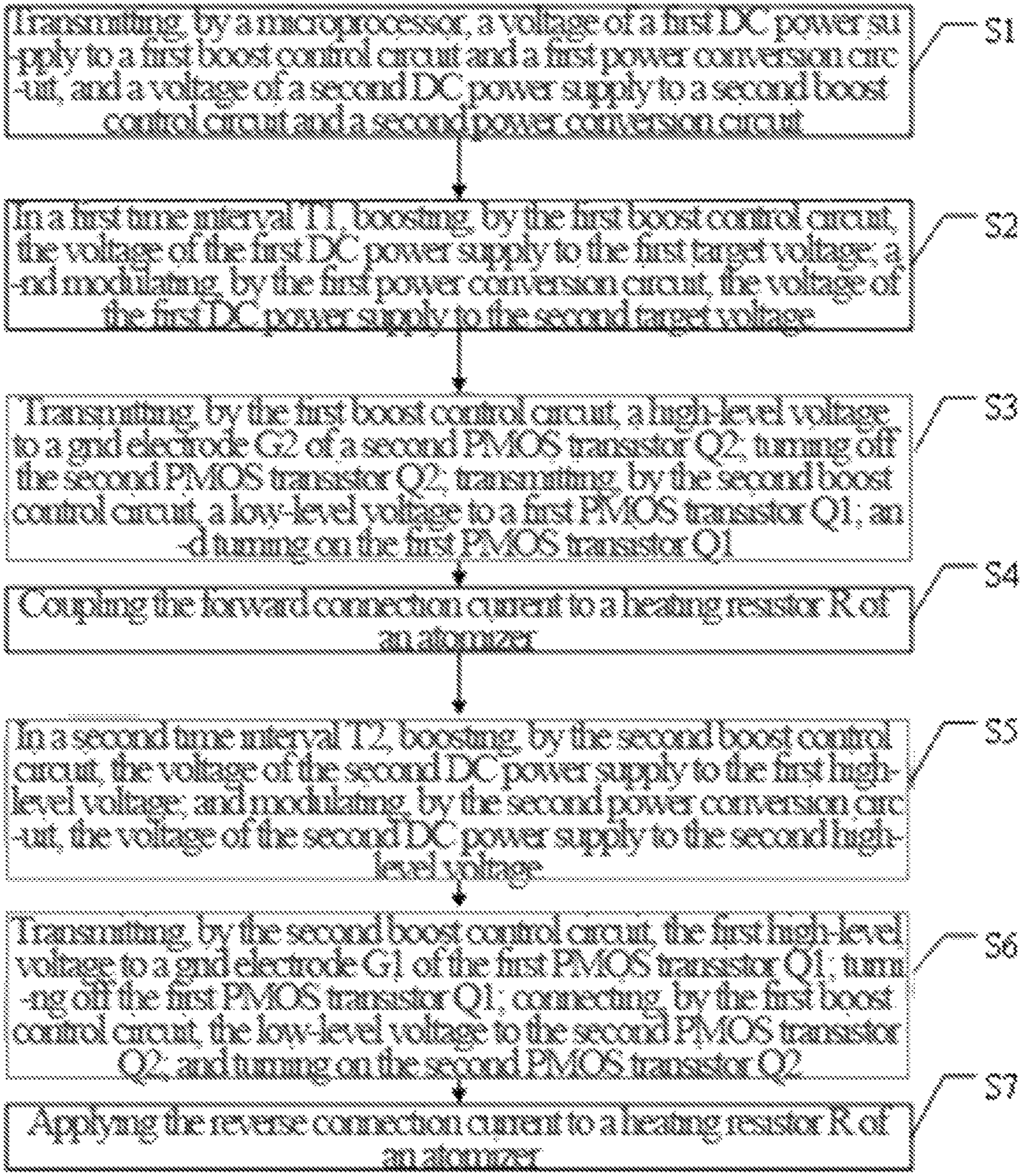
FIG. 42 is a schematic flowchart of a control method of power supply control circuit according to another embodiment of the present disclosure.
Figure 43:
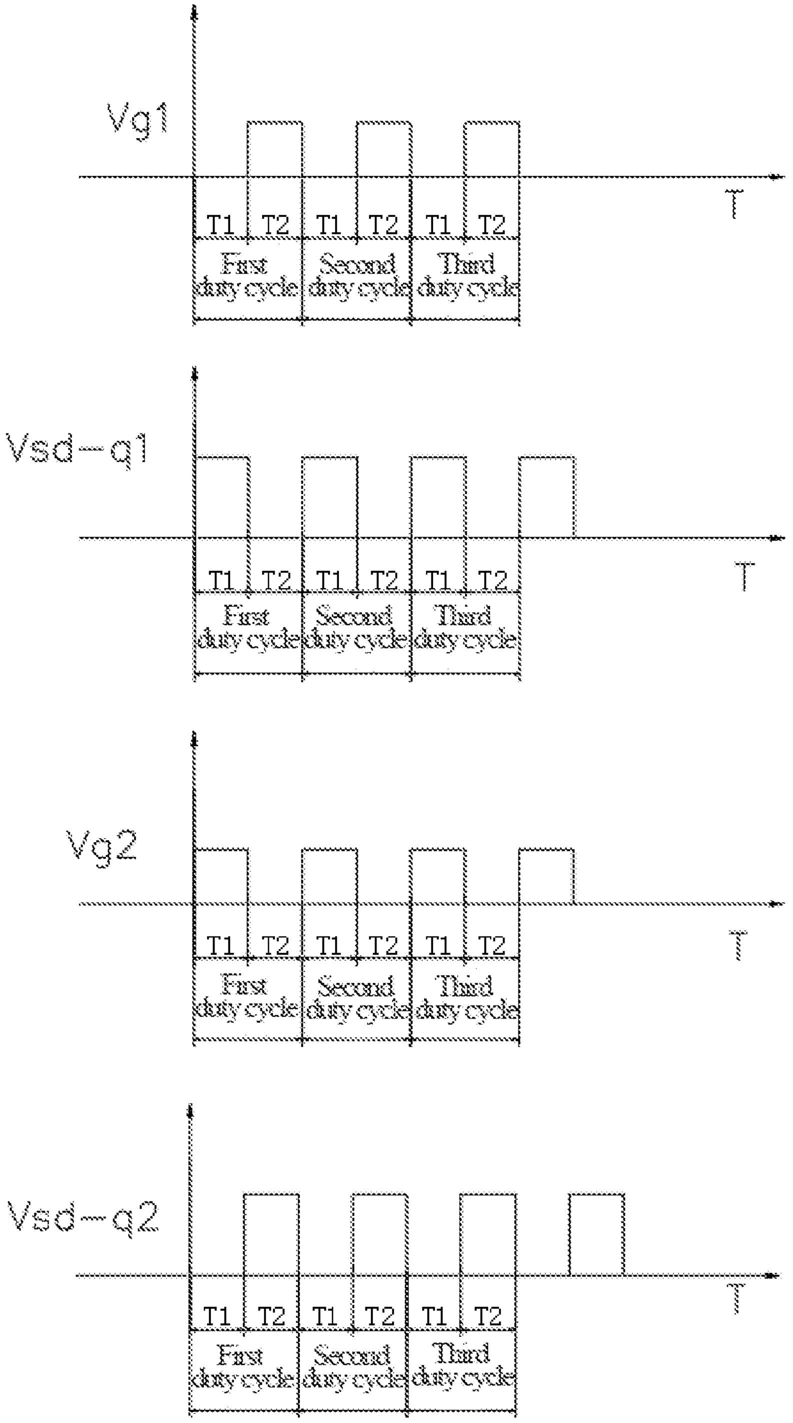
FIG. 43 is a timing diagram of a control method of a power supply control circuit according to another embodiment of the present disclosure.

FIG. 42 is a flow chart of another control method of the power supply control circuit shown in FIG. 41, where the $Q_1$ and the $Q_2$ are PMOS transistors. FIG. 43 is a timing diagram of the control method of the power supply control circuit shown in FIG. 41.

It should be noted that the electrical heating module is the heating resistor R of an atomizer.

The control method of the power supply control circuit provided in this embodiment is performed through the following steps.

(S1) The voltage of the first DC power supply is transmitted to the first boost control circuit and the first power conversion circuit by the microprocessor. The voltage of the second DC power supply is transmitted to the second boost control circuit and the second power conversion circuit by the microprocessor.

(S2) In the first time interval $T_1$, the voltage of the first DC power supply is boosted to a first high-level voltage by the first boost control circuit, and is modulated to a second high-level voltage by the first power conversion circuit.

In this embodiment, the first high-level voltage is the first target voltage which is mentioned in the above embodiment, and the second high-level voltage is the second target voltage which is mentioned in the above embodiment. Since the voltage of the first DC power supply is a forward voltage, the second high-level voltage is accordingly a forward voltage.

(S3) The first high-level voltage is transmitted to a grid electrode $G_2$ of the second PMOS transistor $Q_2$ through the first boost control circuit. The second PMOS transistor $Q_2$ is switched off, meanwhile a low level-voltage is input to the first PMOS transistor $Q_1$ through the second boost control circuit. The first PMOS transistor $Q_1$ is switched on.

(S4) The forward connection current is coupled to the heating resistor R of the atomizer.

(S5) In the second duty cycle $T_2$, the voltage of the second DC power supply is boosted to the first high-level voltage through the second boost control circuit, and is modulated to the second high-level voltage through the second power conversion circuit.

(S6) The first high-level voltage is transmitted to a grid electrode $G_1$ of the first PMOS transistor $Q_1$ through the second boost control circuit. The first PMOS transistor $Q_1$ is switched off. At the same time, the low-level voltage is transmitted to the second PMOS transistor $Q_2$ through the first boost control circuit. The second PMOS transistor $Q_2$ is switched on.

(S7) The reverse connection current is coupled to the heating resistor R of the atomizer.

The steps (S1)-(S7) are repeatedly executed. Since negative electrodes of the two DC power supplies are connected, in different time intervals of the same duty cycle of the second high level voltage, the forward connection current and the reverse connection current are enabled to be alternatively coupled to the heating resistor R of the atomizer. The heating resistor R is alternatively heated, thus the atomizer is heated evenly, which enhances the use performance of the heating resistor and the atomizer, and prolongs the service life of the atomizer provided with the heating resistor.

Figure 44:
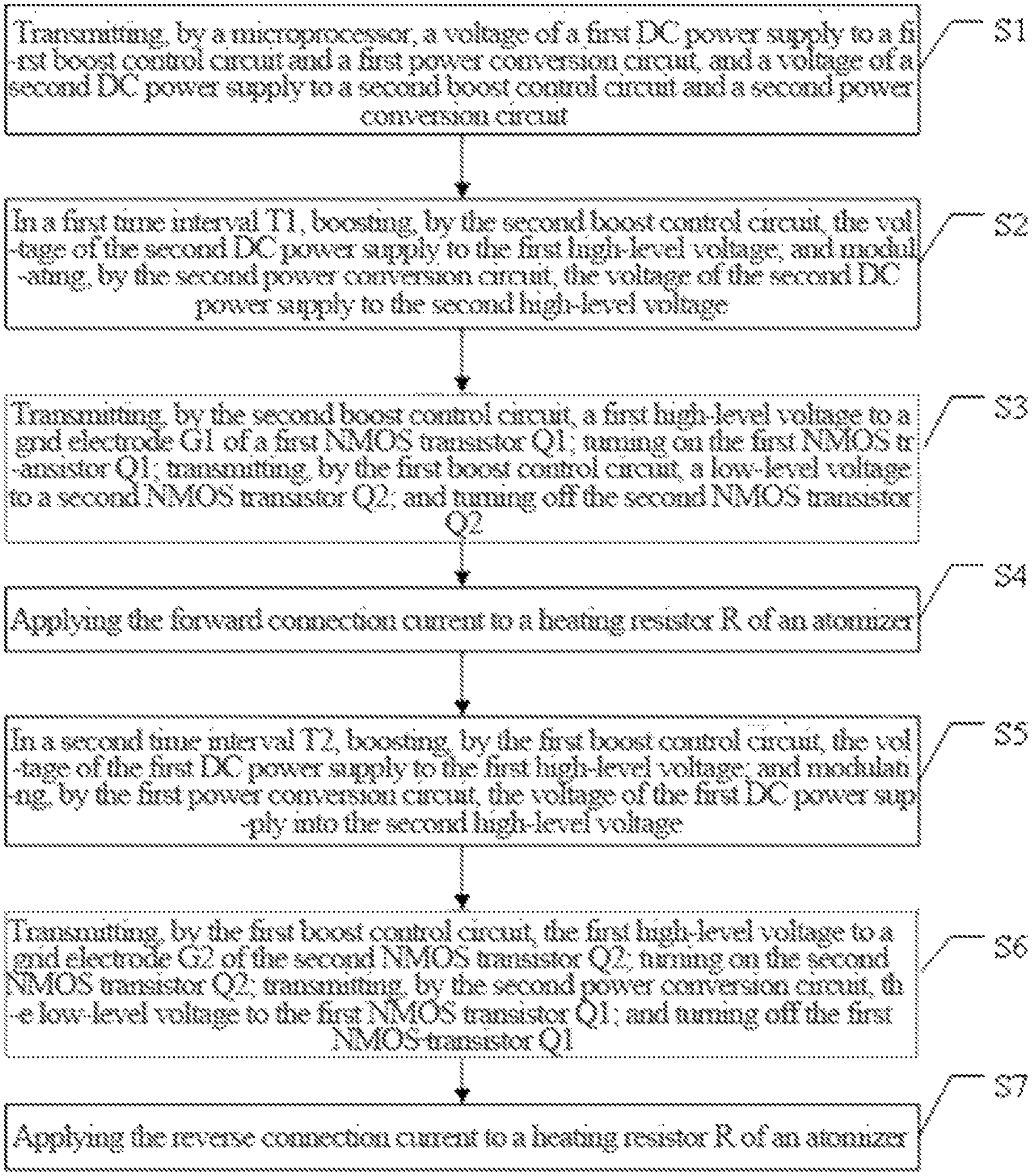
FIG. 44 is a schematic flowchart of another control method of a power supply control circuit according to another embodiment of the present disclosure.

It should be noted that the first PMOS transistor can be replaced with the first NMOS transistor, and the second PMOS transistor can be replaced with the second NMOS transistor, which are illustrated in FIG. 44. FIG. 44 is a schematic flowchart of another control method of a power supply control circuit shown in FIG. 41, where $Q_1$ and $Q_2$ are NMOS transistors.

It should be noted that the electrical heating module in this embodiment is the heating resistor R of an atomizer.

The control method of the power supply control circuit provided in this embodiment is performed through the following steps.

(S1) The voltage of the first DC power supply is transmitted to the first boost control circuit and the first power conversion circuit by the microprocessor. The voltage of the second DC power supply is transmitted to the second boost control circuit and the second power conversion circuit by the microprocessor.

(S2) In the first time interval $T_1$, the second power voltage is boosted to a first high level voltage by the second boost control circuit. The second power voltage is modulated to a second high level voltage by the second power conversion circuit.

(S3) The first high-level voltage is transmitted to a grid electrode $G_1$ of the first NMOS transistor $Q_1$ through the second boost control circuit, and the first NMOS transistor $Q_1$ is switched on. Meanwhile, a low-level voltage is input to the second NMOS transistor $Q_2$ through the first boost control circuit, and the second NMOS transistor $Q_2$ is switched off.

(S4) The forward connection current is coupled to the heating resistor R of the atomizer.

(S5) In the second time interval $T_2$, the first power voltage is boosted into the first high-level voltage through the first boost control circuit, and is modulated to the second high-level voltage through the first power conversion circuit.

(S6) The first high-level voltage is transmitted to a grid electrode $G_2$ of the second NMOS transistor $Q_2$ through the first boost control circuit, and the second NMOS transistor $Q_2$ is switched on. Meanwhile, the low-level voltage is input into the first NMOS transistor $Q_1$ through the second boost control circuit, and the first NMOS transistor $Q_1$ is switched off.

(S7) The reverse connection current is coupled to the heating resistor R of the atomizer.

The steps (S1)-(S7) are carried out repeatedly to alternatively generate the forward connection current and the reverse connection current by the power supply control circuit to heat the heating resistor in the atomizer. The negative electrodes of the two DC power supplies are connected, which enables the forward connection current and the reverse connection current to be coupled alternatively on the heating resistance in the atomizer at different time intervals in the same duty cycle of the second high-level voltage signal. In this way, the heating resistor is heated alternatively to make the atomizer heated evenly, improving the service performance of the atomizer and prolonging the service life of the atomizer equipped with the heating resistor.

The above embodiments have described a first structure of the forward and reverse connection current generation module in the power supply control circuit and a control method thereof.

A second structure of the forward and reverse connection current generation module in the power supply control circuit and a control method thereof are described below.

Figure 45:
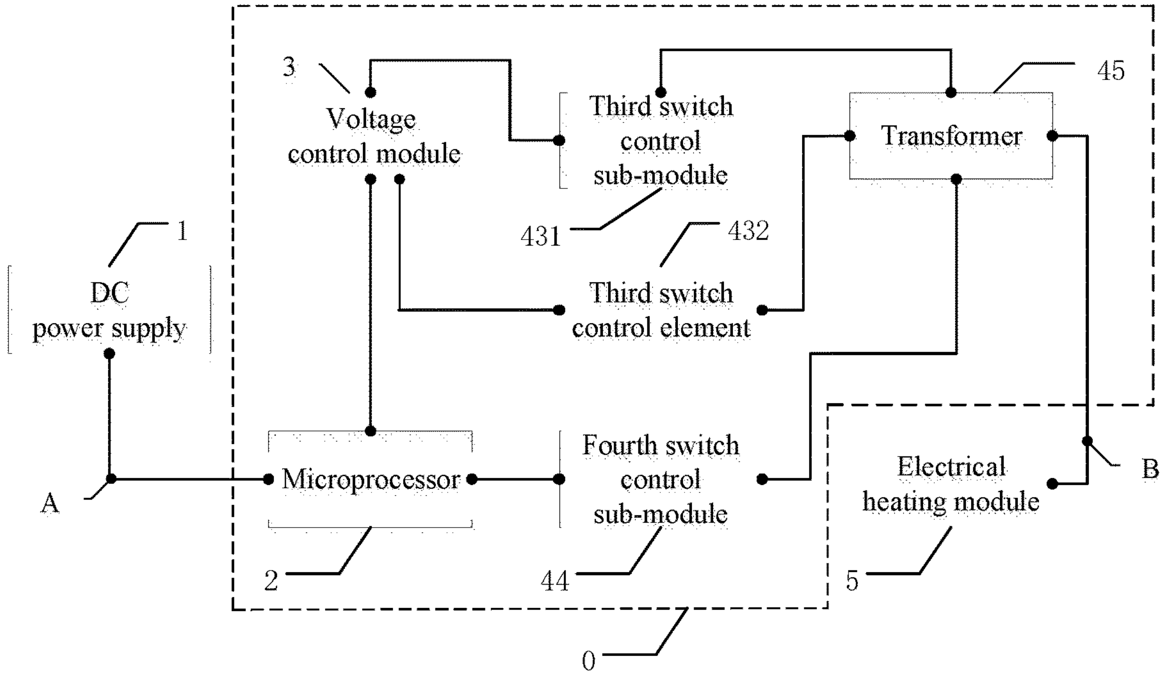
FIG. 45 is a schematic structural diagram of another power supply control circuit according to another embodiment of the present disclosure.

When the forward and reverse connection current generation module in the power supply control circuit is in the second structure, the forward and reverse connection current generation module includes a third switch control element, a third switch control sub-module, and a fourth switch control sub-module, and a voltage transformer. FIG. 45 is a schematic structural diagram of another power supply control circuit in this embodiment, which is a more refined structural depiction of the forward and reverse connection current generation module of the power supply control circuit shown in FIG. 29, when the forward and reverse connection current generation module adopts the second structure.

In this embodiment, the power supply control circuit is composed of a current input terminal A, a current output terminal B, and a current control module 0. The power supply control circuit is connected to the DC power supply 1 through the current input terminal A, and is connected to the electrical heating module 5 through the current output terminal B. The current control module 0 includes a microprocessor 2, a voltage modulation module 3, a third switch control element 432, a third switch control sub-module 431, a fourth switch control sub-module 44, and a voltage transformer 45.

In this embodiment, the third switch control element 432 is configured to couple a second target voltage to the third switch control sub-module 431, the fourth switch control sub-module 44, and the transformer 45.

The third switch control sub-module 431 is configured to be switched on in a first time interval, generate a forward connection current according to the second target voltage, and couple the forward connection current to the transformer 45. The first time interval is a first duration of the second target voltage preset in the same voltage duty cycle.

The fourth switch control sub-module 44 is configured to be switched on in the second time interval, generate a reverse connection current according to the second target voltage, and couple the reverse connection current to the transformer 45. The second time interval is a second duration of the second target voltage preset in the same voltage duty cycle. The sum of the first time interval and the second time interval is not larger than the duration threshold of the same voltage duty cycle.

The transformer 45 is configured to couple the forward connection current to the electrical heating module 5 during the first time interval.

Based on the above-mentioned power supply control circuit with the forward and reverse connection current generation module in the second structure, in another aspect of this embodiment, the control method and implementations of the power supply control circuit are also provided.

Figure 46:
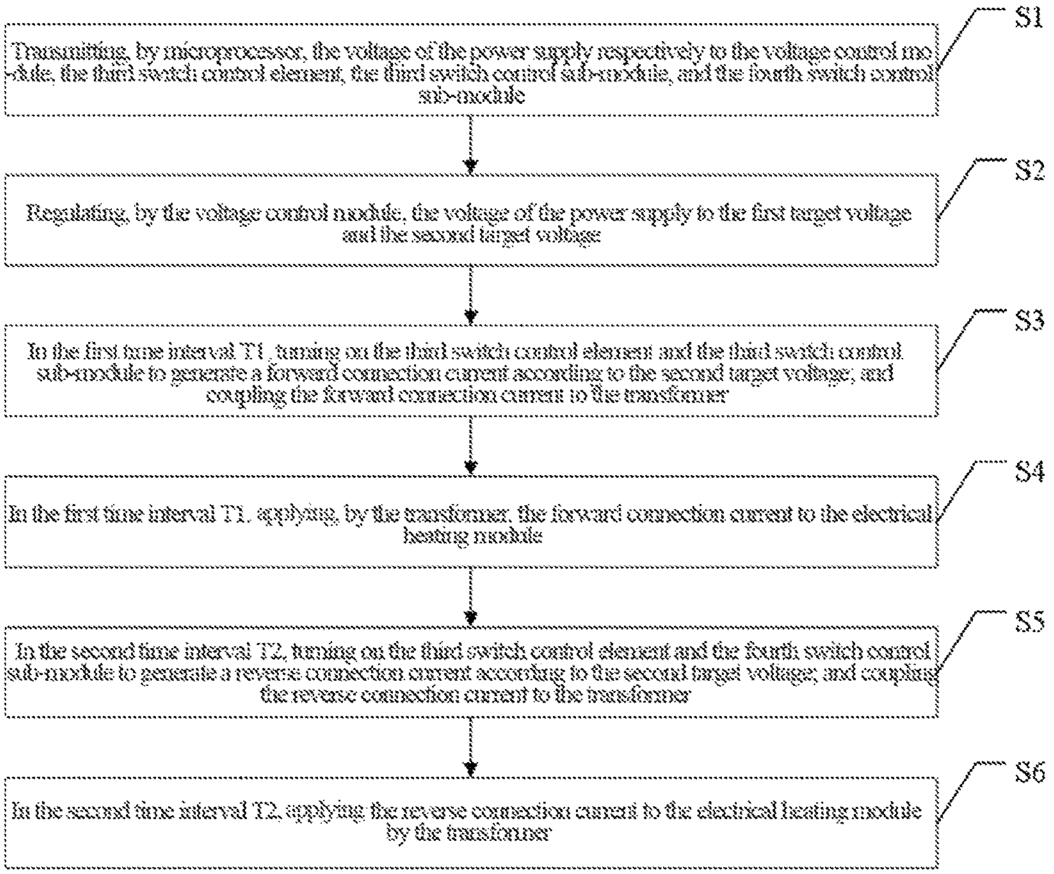
FIG. 46 is a schematic flowchart of a control method of another power supply control circuit according to another embodiment of the present disclosure.

Referring to FIG. 46, another flow chart of the control method of the power supply control circuit in another aspect of this embodiment is provided.

According to the above-mentioned power supply control circuit with the forward and reverse current generation module in the second structure, the control method of the power supply control circuit in another aspect of this embodiment includes the following steps.

(S1) The microprocessor transmits a voltage of the power supply to the voltage modulation module, the third switch control element, the third switch control sub-module, and the fourth switch control sub-module, respectively.

(S2) The voltage modulation module regulates the voltage of the power supply into the first target voltage and the second target voltage.

(S3) In the first time interval $T_1$, the third switch control element and the third switch control sub-module are turned on. A forward connection current is generated according to the second target voltage, and then coupled to the transformer.

In this embodiment, the first time interval is a first duration of the second target voltage preset in the same voltage duty cycle.

(S4) In the first time interval $T_1$, the transformer couples the forward connection current to the electrical heating module.

(S5) In the second time interval $T_2$, the third switch control element and the fourth switch control sub-module are turned on. A reverse connection current is generated according to the second target voltage, and then coupled to the transformer.

In this embodiment, the second time interval is a second duration of the second target voltage preset in the same voltage duty cycle. The sum of the duration of the first time interval and the duration of the second time interval is not larger than the duration threshold of the same voltage duty cycle.

(S6) In the second time interval $T_2$, the transformer couples the reverse connection current to the electrical heating module.

It should be noted that the first target voltage is configured to control the on and off of the third switch control sub-module and the fourth switch control sub-module.

In this embodiment, the third switch control element, the third switch control sub-module, and the fourth switch control sub-module are configured to alternately generate forward connection current and reverse connection current within different durations in the same voltage duty cycle of the second target voltage, so as to alternately and evenly heat the electrical heating module, thereby improving the service performance of the electrical heating module and prolonging the service life of the electrical heating module.

Figure 47:
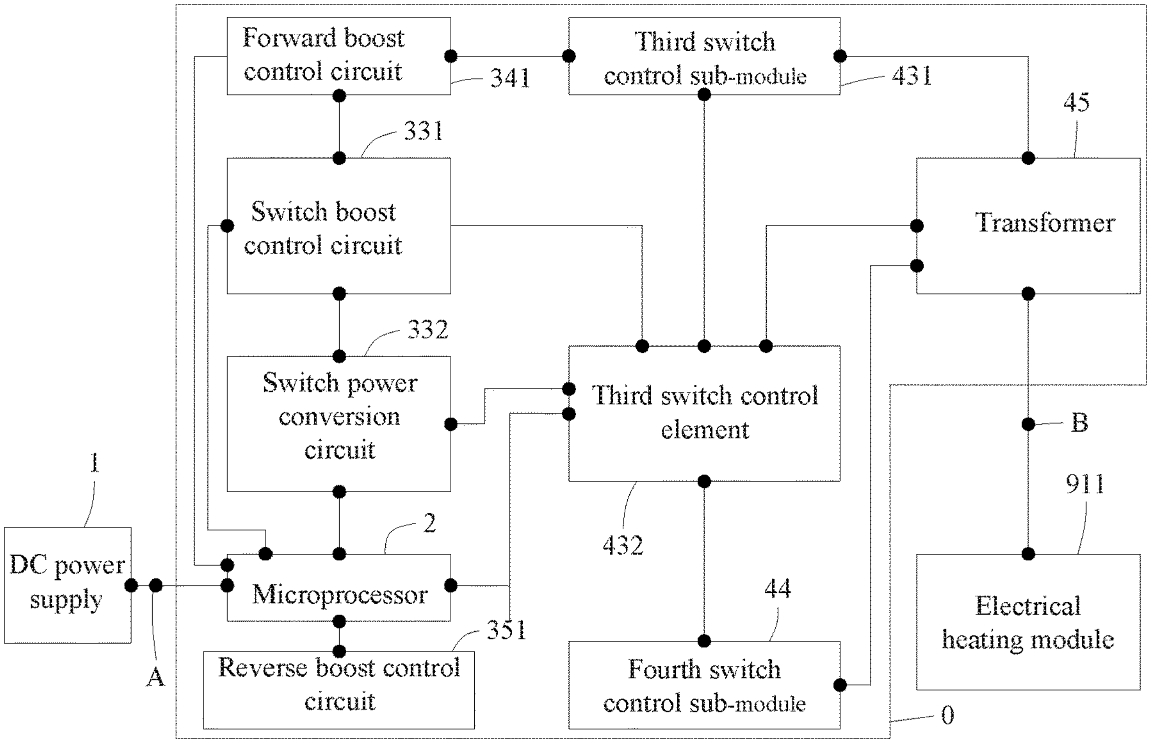
FIG. 47 is a schematic structural diagram of another power supply control circuit in an embodiment of the present disclosure.

Further, FIG. 47 is a schematic structural diagram of another power supply control circuit in another aspect of the embodiment of the present disclosure, which is a more detailed structural description of the voltage control module of the power supply control circuit shown in FIG. 45.

As shown in FIG. 47, the voltage modulation module 3 may include a forward boost control circuit 341, a reverse boost control circuit 351, a switch boost control circuit 331 and a switch power conversion circuit 332.

The forward boost control circuit 341 is configured to control the on and off of the third switch control sub-module 431, boost the voltage of the power supply to obtain the first target voltage in the first time interval, and transmit the first target voltage to the third switch control sub-module 431. One end of the forward boost control circuit 341 is connected to an end of the third switch control sub-module 431, and the other end of the forward boost control circuit 341 is connected to one end of the microprocessor 2.

The reverse boost control circuit 351 is configured to control the on and off of the fourth switch control sub-module 44, boost the voltage of the power supply to obtain the first target voltage in the second time interval, and transmit the first target voltage into the fourth switch control sub-module 44. One end of the reverse boost control circuit 351 is connected to an end of the fourth switch control sub-module 44, and the other end of the reverse boost control circuit 351 is connected to one end of the microprocessor 2.

The switch boost control circuit 331 is configured to boost the voltage of the power supply to obtain a first target voltage, and transmit the first target voltage to the third switch control element 432. One end of the switch boost control circuit 331 is connected to one end of the third switch control element 432, and the other end of the switch boost control circuit 331 is connected to one end of the microprocessor 2.

The switch power conversion circuit 332 is configured to modulate the voltage of the power supply to the second target voltage. One end of the switch power conversion circuit 332 is connected to the other end of the third switch control element 432, and the other end of the switch power conversion circuit 332 is connected to one end of the microprocessor 2.

In addition, the power supply control circuit further includes a direct DC power supply 1, a transformer 45, and an electrical heating module 5 that are similar to those mentioned in the above embodiments. The DC power supply 1 is connected to the other end of the microprocessor 2. One side of the transformer 45 is connected to the third switch control sub-module 431, the third switch control element 432, and the fourth switch control sub-module 44, respectively, and the other side of the transformer 45 is connected to the electrical heating module 5.

In this embodiment, the third switch control sub-module 431 may include a fifth transistor. A first terminal of the fifth transistor is grounded, a second terminal of the fifth transistor is connected to the one end of the first main coil in the transformer, and a third terminal of the fifth transistor is connected to an end of the forward boost control circuit.

The fourth switch control sub-module 44 may include a sixth transistor. A first terminal of the sixth transistor is connected to one end of the reverse boost control circuit, a second terminal of the sixth transistor is connected to one end of a second main coil in the transformer, and a third terminal of the sixth transistor is connected to an end of the reverse boost control circuit.

The third switch control element 432 may include a seventh transistor. A first terminal of the seventh transistor is connected to the other end of the first main coil of the transformer and the other end of the second main coil, a second terminal of the seventh transistor is connected to an end of the switch power conversion circuit, and the third terminal of the seventh transistor is connected to an end of the switch power conversion circuit.

The other end of the first main coil of the transformer and the other end of the second main coil are connected to the first connecting point. One end of a secondary coil of the transformer is connected to one end of the electrical heating module, and the other end of the secondary coil of the transformer is connected to the other end of the electrical heating module.

It should be noted that the fifth transistor, the sixth transistor, and the seventh transistor all can be field-effect transistors, or triodes. Or, the fifth transistor and the sixth transistor are field-effect transistors, and the seventh transistor is a triode, which is not specifically limited herein.

In this embodiment, if the fifth transistor, the sixth transistor, and the seventh transistor are all field-effect transistors, all of the fifth transistor, the sixth transistor and the seventh transistor may be NMOS transistors. When the grid electrode (G) of the NMOS transistor is connected to the high level, the NMOS transistor is turned on. When the grid electrode (G) of the NMOS transistor is connected to the low level, the NMOS transistor is turned off. Alternatively, both of the fifth transistor and the sixth transistor may be PMOS transistors, and the seventh transistor is an NMOS transistor, which are not limited herein. The characteristic of the PMOS transistor is that when the grid electrode (G) of the PMOS transistor is connected to a low level, the PMOS transistor is turned on, and when the grid electrode (G) of the PMOS transistor is connected to a high level, the PMOS transistor is turned off.

If the fifth transistor, the sixth transistor and the seventh transistor are all triodes, the fifth transistor, the sixth transistor and the seventh transistor can be to be NPN triodes. When the base terminal (B) of the NPN triode is connected to high level, the NPN triode is turned on, and when the base terminal (B) of the NPN triode is connected to low level, the NPN triode is turned off. In addition, all of the fifth transistor, the sixth transistor and the seventh transistor are triodes, can be PNP triodes, or the fifth transistor, the sixth transistor can be the NPN triodes and the seventh transistor can be a PNP triode, which are not limited herein.

Further, the third switch control sub-module 431 may have two or more transistors, and the fourth switch control sub-module may also have two or more transistors. Moreover, the number of the transistors in the third switch control sub-module can be the same as or different from the number of the transistors in the fourth switch control sub-module, which is not specifically limited herein.

In this embodiment, in the first time interval, the fifth transistor and the seventh transistor are both turned on, and the sixth transistor is turned off. The current flows from the seventh transistor through the transformer and the fifth transistor to form the forward connection current. Then, the transformer couples the forward connection current to the electrical heating module. In the second time interval, the sixth transistor and the seventh transistor are both turned on, and the fifth transistor is turned off. The current flows from the seventh transistor through the transformer and the sixth transistor to form a reverse connection current. Then, the transformer couples the reverse connection current to the electrical heating module. In this way, the electrical heating module is heated alternately by the forward connection current and the reverse connection current such that the electrical heating module is heated evenly, improving the service performance of the electrical heating module, and prolonging the service life of the electrical heating module.

Further, in another aspect of this embodiment, a dotted terminal of the first main coil and the secondary coil is a first dotted terminal, and a dotted terminal of the second main coil and the secondary coil is a second dotted terminal. The first dotted terminal of the first main coil is provided at the high electrical potential end of the first main coil, and the high electrical potential end is located at a connecting point of the first main coil. The second dotted terminal of the second main coil is provided at a low electrical potential end of the second main coil, and the low electrical potential end of the second main coil is located at an end of the second main coil that is connected to the second terminal of sixth transistor. The first dotted terminal and the second dotted terminal of the secondary coil are located at any of the same end of the secondary coil.

Preferably, another technical solution for achieving the above-mentioned embodiment of this disclosure is illustrated as follows.

Figure 48:
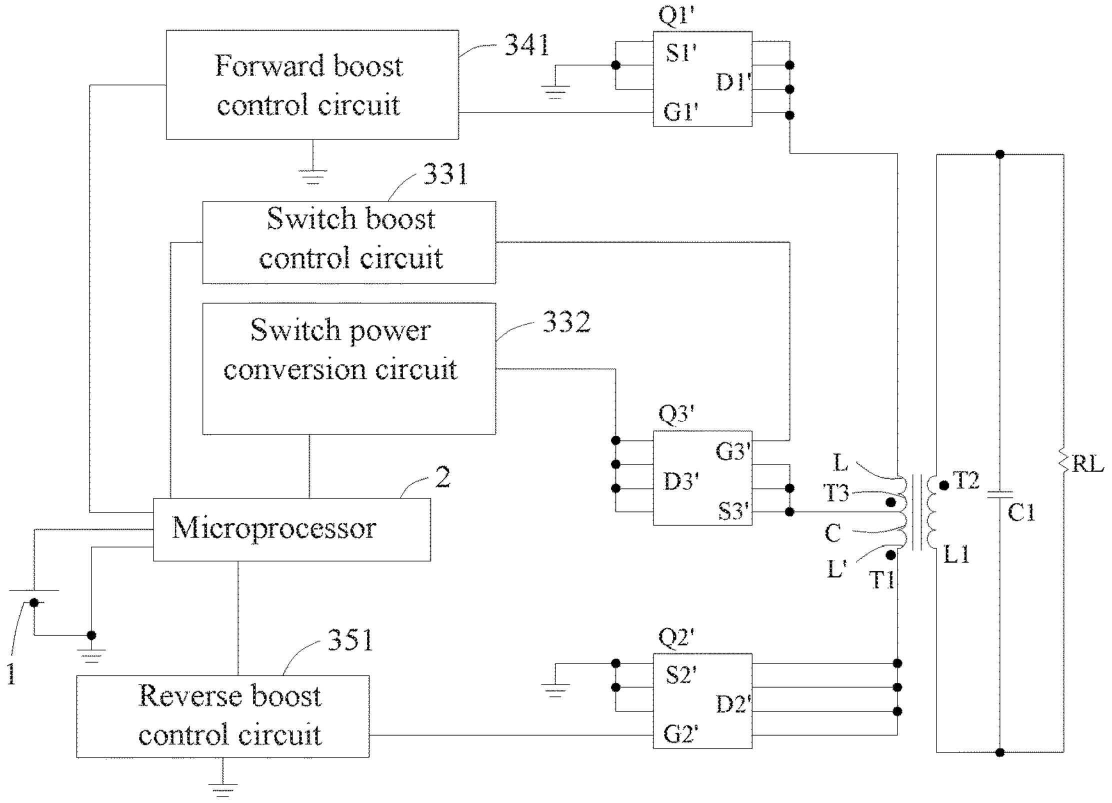
FIG. 48 is an equivalent schematic diagram of another power supply control circuit according to another embodiment of the present disclosure.

FIG. 48 is an equivalent schematic diagram of another power supply control circuit according to an embodiment of the present disclosure.

In this embodiment, it should be noted that the electrical heating module is the heating resistance $R_L$ of the atomizer.

The power supply control circuit provided in this embodiment is illustrated as follows.

A third switch control sub-module of the power supply control circuit includes an NMOS transistor $Q_1'$, where a source electrode $S_1'$ of the NMOS transistor $Q_1'$ is grounded, a drain electrode $D_1$' of the NMOS transistor $Q_1$' is connected to one end of the first main coil L of the transformer, and a grid electrode $G_1$' of the NMOS transistor $Q_1$' is connected to one end of the forward boost control circuit.

A fourth switch control sub-module of the power supply control circuit includes an NMOS transistor $Q_2$', where a source electrode $S_2$' of the NMOS transistor $Q_2$' is connected to one end of the reverse boost control circuit, a drain electrode $D_2$' of the NMOS transistor $Q_2$' is connected to one end of the second main coil L' of the transformer, and a grid electrode $G_2$' of the NMOS transistor $Q_2$' is connected to one end of the reverse boost control circuit.

A third switch control element includes an NMOS transistor $Q_3$', where a source electrode $S_3$' of the NMOS transistor $Q_3$' is connected to the other end of the first main coil L of the transformer and the other end of the second main coil L', and a drain electrode $D_3$' of the NMOS transistor is connected to one end of the switch power conversion circuit, and a grid electrode $G_3$' of the NMOS transistor $Q_3$' is connected to one end of the switch boost control circuit.

The other end of the first main coil L and the other end of the second main coil L' in the transformer are connected to a first connecting point C. One end of the secondary coil $L_1$ of the transformer is connected to one end of the heating resistance $R_L$ of the atomizer, the other end of the secondary coil $L_1$ of the transformer is connected to the other end of the heating resistance $R_L$ of the atomizer.

A terminal $TM_3$ of the first main coil L and a terminal $TM_2$ of the secondary coil $L_1$ are the first dotted terminals, a terminal $TM_1$ of the second main coil L' and the terminal $TM_2$ of the secondary coil are the second dotted terminals. The $TM_3$ of the first main coil L is arranged on a high electrical potential end of the first main coil that is located at the connecting point C. The terminal $TM_1$ of the second main coil L' is arranged on a low electrical potential end of the second main coil L', where the low electrical potential end is located at an end of the second main coil L' that is connected to the drain electrode $D_2$' of the NMOS transistor $Q_2$'. The first dotted terminal and the second dotted terminal of the secondary coil $L_1$ are both located at an upper terminal $TM_2$ of the secondary coil $L_1$.

It should be noted that the first dotted terminal and the second dotted terminal of the secondary coil $L_1$ can be both located at a lower terminal of the secondary coil $L_1$, which is not specifically limited here.

It should be noted that in the power supply control circuit provided in another aspect of this embodiment in FIG. 48, a capacitor $C_1$ is connected to the secondary coil $L_1$ of the transformer and the heating resistance $R_L$, respectively. The capacitor $C_1$ is configured to store electrical charges. However, in the power supply control circuit provided in an embodiment of this disclosure, the transformer c be not connected to the capacitor, but only designed to be connected to the heating resistor $R_L$ to form a current circuit between the transformer and the heating resistor $R_L$.

In this embodiment, in the first time interval, the NMOS transistor $Q_3$' and the NMOS transistor $Q_1$' are turned on, the NMOS transistor $Q_2$' is turned off, so that the forward connection current is coupled to secondary coil $L_1$ of the transformer via the first main coil L of the transformer, and then flows through the capacitor $C_1$ and the heating resistor $R_L$ in the atomizer from top to bottom. In the second time interval, the NMOS transistor $Q_3$' and the NMOS transistor $Q_2$' are turned on, and the NMOS transistor $Q_1$' is turned off, such that the reverse connection current is coupled to the secondary coil $L_1$ of the transformer via the second main coil L' of the transformer, and flows through the capacitor $C_1$ and the heating resistor $R_L$ in the atomizer from top to bottom, thereby heating the heating resistor $R_L$ alternately, allowing the atomizer to be heated evenly, improving the service performance of the atomizer, and prolonging the service life of the atomizer.

In another aspect of this embodiment, referring to FIG. 48, although the source electrode and the drain electrode of each NMOS transistor both have a plurality of pins, the number of the plurality of pins of the source and drain electrodes of each NMOS transistor are not limited, which can be one, two, or more.

Figure 49:
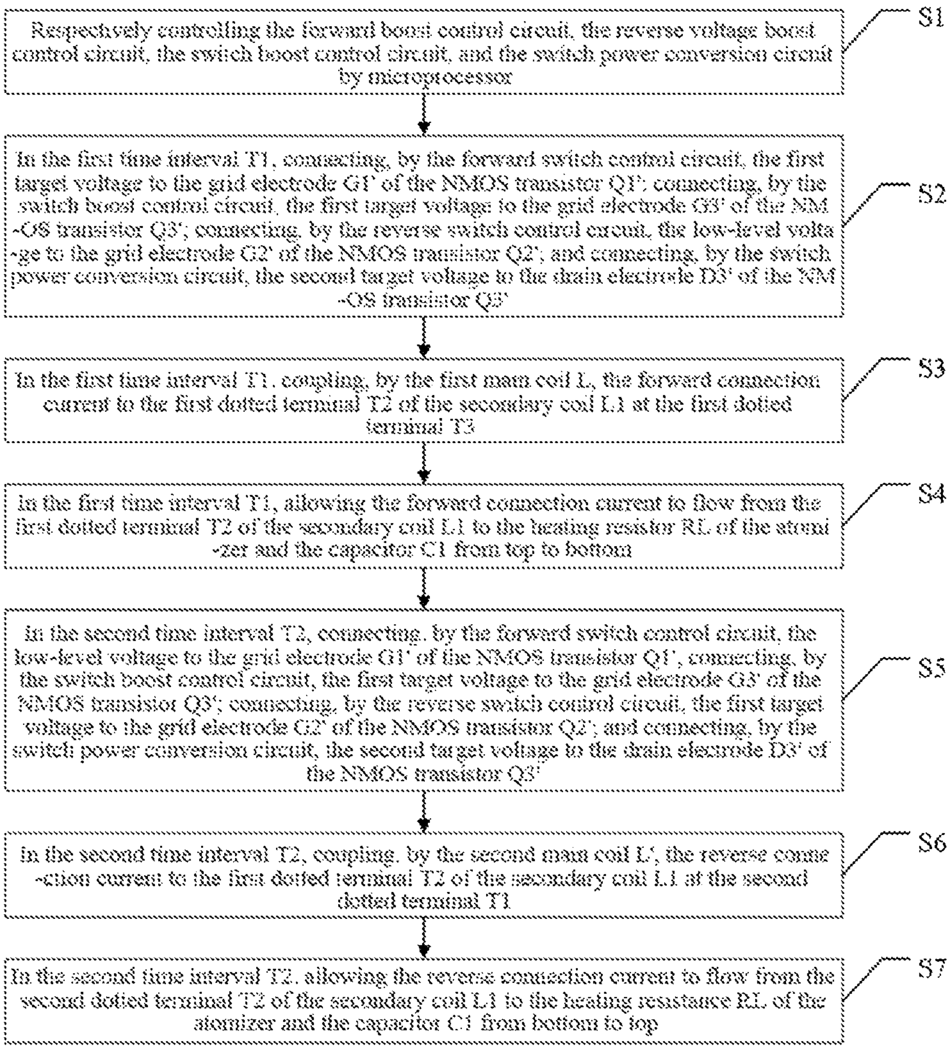
FIG. 49 is a schematic flowchart of a control method of another power supply control circuit according to another embodiment of the present disclosure.
Figure 50:
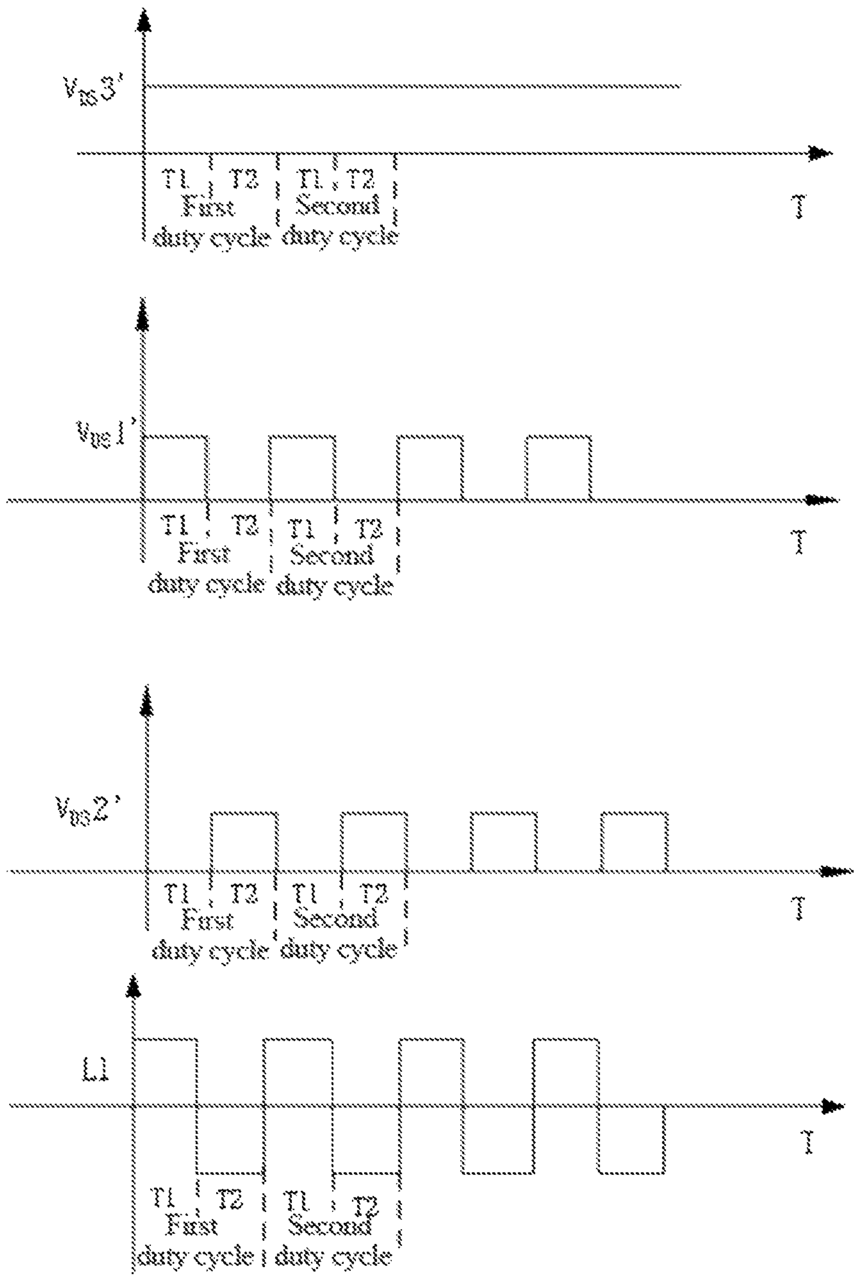
FIG. 50 is a timing diagram of the control method of another power supply control circuit according to another embodiment of the present disclosure.

Further, as shown FIGS. 48-50, FIG. 49 is a flowchart of a control method of the power supply control circuit shown in FIG. 48, where $Q_1$', $Q_2$' and $Q_3$' are NMOS transistors. FIG. 50 shows a timing diagram of the control method of the power supply control circuit.

It should be noted that FIG. 50 respectively shows timing diagrams of control methods of the NMOS transistor $Q_3$', the NMOS transistor $Q_1$', the NMOS transistor $Q_2$', and the secondary coil $L_1$ in the transformer from up to bottom, where the horizontal axis indicates the duration of the voltage cycle, and the vertical axis indicates the voltage amplitude.

In this embodiment, the control method of the power supply control circuit may include the following steps.

(S1) The microprocessor respectively controls the forward voltage boost control circuit, the reverse voltage boost control circuit, the switch boost control circuit, and the switch power conversion circuit.

(S2) In the first time interval $T_1$, the forward switch control circuit allows the first target voltage to be connected to the grid electrode $G_1$' of the NMOS transistor $Q_1$'. The switch boost control circuit allows the first target voltage to be connected to the grid electrode $G_3$' of the NMOS transistor $Q_3$'. The reverse switch control circuit allows the low-level voltage to be connected to the grid electrode $G_2$' of the NMOS transistor $Q_2$'. The switch power conversion circuit allows the second target voltage to be connected to the drain electrode $D_3$' of the NMOS transistor $Q_3$'.

In this embodiment, the first target voltage is the high-level voltage. In the first time interval $T_1$ in the same voltage duty cycle of the second target voltage, the NMOS transistors $Q_3$' and the NMOS transistor $Q_1$' are turned on, and the NMOS transistor $Q_2$' is turned off. When the NMOS transistors $Q_3$' and the NMOS transistor $Q_1$' are turned on, a voltage of the first connecting point C, where the first main coil L and the second main coil L' are connected, is higher than the voltage of the other end of the first main coil L, so as to generate a forward connection current according to the second target voltage that passes through the first main coil L of the transformer from up to bottom, that is, the forward connection current flows from the first connecting point C to the first main coil L and the NMOS transistor $Q_1$'.

(S3) In the first time interval $T_1$, the first main coil L couples the forward connection current to the first dotted terminal $T_2$ of the secondary coil $L_1$ at the first dotted terminal $T_3$.

In this embodiment, in the first time interval $T_1$, the voltage at the first dotted terminal $T_3$ of the first main coil L is the voltage at the first connecting point C. Namely, the voltage at the first dotted terminal $T_3$ of the first main coil L is the high voltage, consequently, the voltage coupled to the first dotted terminal $T_2$ of the secondary coil $L_1$ is also the high voltage.

(S4) In the first time interval $T_1$, the forward connection current flows from the first dotted terminal $T_2$ of the secondary coil $L_1$ to the heating resistor $R_L$ of the atomizer and the capacitor $C_1$ from top to bottom.

In this embodiment, the capacitor $C_1$ is configured for rectification and charge storage.

(S5) In the second time interval $T_2$, the forward switch control circuit allows the low-level voltage to be connected to the grid electrode $G_1$' of the NMOS transistor $Q_1$'. The switch boost control circuit allows the first voltage to be connected to the grid electrode $G_3$' of the NMOS transistor $Q_3$'. The reverse switch control circuit allows the first target voltage to be connected to the grid electrode $G_2$' of the NMOS transistor $Q_2$'. The switch power conversion circuit allows the second target voltage to be connected to the drain electrode $D_3$' of the NMOS transistor $Q_3$'.

In this embodiment, in the second time interval $T_2$ in the same voltage duty cycle of the second target voltage, the NMOS transistors $Q_3$' and $Q_2$' are turned on, and the NMOS transistor $Q_1$' is turned off to generate a reverse connection current according to the second target voltage. The reverse connection current flows through the second main coil L' of the transformer from top to bottom. Namely, the reverse connection current flows from the first connecting point C of the first main coil L and the second main coil L' of the transformer to the second main coil L' and the NMOS transistor $Q_2$'.

(S6) In the second time interval $T_2$, the second main coil L' couples the reverse connection current to the first dotted terminal $T_2$ of the secondary coil $L_1$ at the second dotted terminal $T_1$.

In this embodiment, in the second time interval $T_2$, the voltage at the second dotted terminal $T_1$ of the second main coil L' is the low voltage. Namely, at this time, the voltage at the second dotted terminal $TM_1$ of the second main coil L' is the low voltage, and consequently the voltage coupled to the first dotted terminal $TM_2$ of the secondary coil $L_1$ is also the low voltage.

In another aspect of this embodiment in this disclosure, the power supply control circuit is capable of generating a forward connection current through the switching-on of NMOS transistors $Q_3$' and $Q_1$' during the first time interval of the same voltage operating cycle of the second target voltage, and applying the forward connection current to the heating resistor of the atomizer from top to bottom through a transformer, and generating a reverse connection current through the switching-on of NMOS transistors $Q_3$' and $Q_2$' during the second time interval of the same voltage operating cycle of the second target voltage, and applying the reverse connection current to the atomizer from bottom to top through a transformer. In this way, the heating resistance of the atomizer is heated alternately, so that the atomizer can be uniformly heated, improving the service performance of the atomizer, and prolonging the service life of the atomizer equipped with the heating resistor.

(S7) In the second time interval $TM_2$, the reverse connection current flows from the first dotted terminal $TM_2$ of the secondary coil $L_1$ to the heating resistor $R_L$ of the atomizer and the capacitor $C_1$ from bottom to top.

In this embodiment, the power supply control circuit is configured to allow the forward connection current to be coupled to the heating resistor of the atomizer through the first dotted terminal $T_2$ of the secondary coil L of the transformer from top to bottom during the first time interval, and the reverse connection current is coupled to the heating resistor of the automizer from bottom to top during the second time interval, such that heating resistor of the atomizer is heated alternately, making the atomizer heated evenly, improving the service performance of the atomizer, and prolonging the service life of the atomizer equipped with the heating resistor.

This embodiment also provides a personal vaping device in which the electrical heating module is an atomizer or a heater. The personal vaping device includes at least one power supply control circuit. The power supply control circuit includes a current input terminal, a current output terminal, and a current control module.

The current control module is composed of a microprocessor, a voltage modulation module and a forward and reverse connection current generation module.

The voltage modulation module is configured to modulate the first target voltage and the second target voltage.

The forward and reverse connection current generation module is configured to generate the forward connection current and the reverse connection current according to the second target voltage. Both the forward connection current and the reverse connection current drives the atomizer or the heater to generate heat.

The control method of the power supply control circuit is performed as follows.

The voltage modulation module couples the second target voltage to the forward and reverse connection current generation module.

The forward and reverse connection current generation module couples the forward connection current and the reverse connection current to the atomizer or the heater at different time intervals in the same voltage duty cycle of the second target voltage.

In this embodiment, the power supply control circuit is allowed to generate the forward connection current and the reverse connection current through the forward and reverse connection current generation module, such that the atomizer or the heater is heated alternately, thereby uniformly heating the atomizer or the heater, boosting the service performance of the atomizer or the heater, improving the taste of the personal vaping device, and prolonging the service life of the atomizer or the heater provided with the heating resistor.

Even though this disclosure has been shown and illustrated with respect to one or more embodiments, equivalent changes and modifications can be made by those skilled in the art based on the description and the accompanying drawings. Any changes and modifications are included in this disclosure, and are limited by the protection scope of the appended claims. In particular, with respect to the various functions performed by the components described above, unless otherwise specified, the terms used to describe such components are intended to correspond to any component that performs the specified function (i.e., components with equivalent functions), even if the components are not structurally equivalent to the disclosed structure that performs the functions of the embodiments shown herein.

Described above are only parts of embodiments of this disclosure, and are not intended to limit the protection scope of this disclosure. Any transformations of equivalent structure or equivalent process made according to the description and accompanying drawings of this disclosure, such as mutual combination of the technical features, or direct or indirect application in other related technical fields, shall fall within the protection scope of this disclosure.

The above description illustrates specific details of the present disclosure for explanation. It should be understood by one ordinary of skill in the art that this disclosure can be implemented without those specific details. In some other embodiments, the structures and processes in the common knowledge are not described in detail to avoid obscuration of the description caused by the unnecessary details. Thus, this disclosure is not intended to be limited to the above embodiments, but to be consistent with the widest scope of the principles and technical features disclosed herein.

This disclosure further includes the following aspects.

Provided herein is a control method for heating the electrical heating module, which includes the following steps.

An electrical heating module is provided. The electrical heating module has a first end and a second end. In the first repetition cycle, the total energy provided by the electrical field to the electrical heating module is Q.

The first repetition cycle is composed of a first time interval and a second time interval. In the first time interval, a first current $I_1$ flows from the first end to the second end, and a first energy value generated by the first current $I_1$ passing through the electrical heating module is α*Q. In the second time interval, the second current $I_2$ flows from the second end to the first end, and the second energy generated by the second current $I_2$ passing through the electrical heating module is β*Q, where the total energy Q satisfies the following formulas:

$$Q=\alpha^*Q+\beta^*Q \quad (1); \text{ and}$$

$$\alpha+\beta=1 \quad (2);$$

where α is an energy coefficient of the first energy; and β is an energy coefficient of the second energy.

Based on the control method for heating the electrical heating module, in the first time interval, the total energy provided by the electric field to the electrical heating module is Q. A first current $I_1$ flows from the first end to the second end, and a first energy value generated by the first current $I_1$ passing through the electrical heating module is α*Q. In the second time interval, a second current $I_2$ flows from the second end to the first end, and a second energy value generated by the second current $I_2$ passing through the electrical heating module is β*Q, where Q=α*Q+β*Q, and α+β=1. When the total energy of the electrical heating module remains unchanged, the total energy is distributed to be in a forward energy state and in a reverse energy state to be distributed to the electrical heating device. The energy is randomly distributed on the electrical heating module. Compared with a traditional design, the electrical heating module provided herein is uniformly heated, which not only stabilizes the heating temperature, but also effectively prevents foreign substances (such as carbides) from accumulating on the surface of the electrical heating module and maintains the cleanliness of the electrical heating module, so that the pure taste of the atomized e-cigarette oil or the baked non-combustible tobacco is ensured.

In some embodiments of this disclosure, the voltage when the first current $I_1$ passes through the electrical heating module is a first voltage $U_1$, and the voltage when the second current $I_2$ passes through the electrical heating module is a second voltage $U_2$. Both the first voltage $U_1$ and the second voltage $U_2$ satisfy the following formula:

$$U_1 \neq U_2 \quad (3).$$

In some embodiments of this disclosure, the first time interval is not equal to the second time interval.

In a second repetition cycle, the total energy provided by the electrical field to the electrical heating module is Q. The second repetition cycle includes a third time interval and a fourth time interval. In the third time interval, a third current $I_3$ flows from the first end to the second end, and a third energy value generated by the third current $I_3$ passing through the electrical heating module is μ*Q. In the fourth time interval, a fourth current $I_4$ flows from the second end to the first end, and a fourth energy value $I_4$ generated by the fourth current $I_4$ passing through the electrical heating module is γ*Q, where the total energy Q satisfies the following formulas:

$$Q=\mu^*Q+\gamma^*Q \quad (4); \text{ and}$$

$$\mu+\gamma=1 \quad (5);$$

where μ is an energy coefficient of the third energy value; and γ is an energy coefficient of the fourth energy value.

In some embodiments, μ and γ satisfy the following formulas:

$$\mu \neq \alpha \quad (6); \text{ and}$$

$$\gamma \neq \beta \quad (7).$$

According to some embodiments of this disclosure, the voltage when the first current $I_1$ passes through the electrical heating device is a first voltage $U_1$. The voltage when the second current $I_2$ passes through the electrical heating device is a second voltage $U_2$. The voltage when the third current $I_3$ passes through the electrical heating module is a third voltage $U_3$, and a voltage when the fourth current $I_4$ passes through the electrical heating module is a fourth voltage $U_4$, where the first voltage $U_1$, the second voltage $U_2$, the third voltage $U_3$, and the fourth voltage $U_4$ satisfy the following formula:

$$U_3 \neq U_4 \quad (8);$$

$$U_3 \neq U_1 \quad (9); \text{ and}$$

$$U_4 \neq U_2 \quad (10).$$

In some embodiments, the duration of the first repetition cycle is not equal to the duration of the second repetition cycle.

In some embodiments of this disclosure, the third time interval and the fourth time interval are not equal.

In some embodiments, a first time range includes at least two first repetition cycles, and a second time range includes at least two second repetition cycles.

In some embodiments, the first voltage $U_1$ is variable and forms at least one peak or trough.

In some embodiments, the first voltage $U_1$ forms at least one constant-voltage section.

In some embodiments, the first voltage $U_1$ forms at least two peaks or at least two troughs.

In some embodiments, the second voltage $U_2$ is variable and forms at least one peak or trough.

In some embodiments, the second voltage $U_2$ forms at least one constant-voltage section.

In some embodiments, the second voltage $U_2$ forms at least two peaks or at least two troughs.

A control method for heating the electrical heating module is provided in another embodiment, which is performed as follows.

An electrical heating module is provided. The electrical heating module has a first end and a second end. The electrical heating module is applied with an AC. The direction of the current is defined as a direction along which the current flows from the high potential to the low potential.

The repetition cycles of the AC include a first repetition period and a second repetition period. One of repetition periods includes at least a first sub-period and a second sub-period. In the first sub-period, the current flows from the first end to the second end, and in the second sub-period, the current flows from the second end to the first end. Another repetition period includes a third sub-period, and the current flows from the first end to the second end or from the second end to the first end in the third sub-period.

According to the control method for heating the electrical heating module in this application, the total energy is distributed to be in a forward energy state and in a reverse energy state to be distributed to the electrical heating device. The energy is randomly distributed to the electrical heating module, combined with the variation of the direction of the current. Compared with the traditional design, the electrical heating module provided herein is uniformly heated, stabilizing the heating temperature, effectively preventing foreign substances (such as carbides) from accumulating on the surface of the electrical heating module and maintaining the cleanliness of the electrical heating module, so that the pure taste of the atomized e-cigarette oil and the baked non-combustible tobacco can be ensured.

In some embodiments, the voltage in at least one of the first sub-period, the second sub-period, and the third sub-period is constant.

In some embodiments, the voltage in at least one of the first sub-period, the second sub-period, and the third sub-period is variable.

A control method for heating the electrical heating module is provided in another embodiment, which includes the following steps.

The electrical heating module is provided, which has a first end and a second end. A positive direction is defined as a direction along which the current flows from the first end to the second end, and a negative direction is defined as a direction along which the current flows from the second end to the first end.

An AC is provided to supply the electrical heating module in an alternately forwarding and reversing manner in a minimum repetition cycle.

According to the control method for heating the electrical heating module provided herein, the electrical heating module is provided, and AC is provided to supply the electrical heating module in an alternately forwarding and reversing manner in a minimum repetition cycle, so that the heat energy of the electrical heating module can be uniformly distribute, preventing the oil-guiding cotton assembled with the electrical heating module from excessively being burned due to the high local temperature, and prolonging the service life of the automizer. At the same time, the electrical field also presents a positive direction and a negative direction alternatively on the electrical heating module, effectively preventing foreign substances such as carbides from accumulating on the surface of the electrical heating module, maintaining the cleanliness of the electrical heating module, and ensuring the pure taste of the atomized e-cigarette.

In some embodiments, the minimum repetition period includes a first period, a second period, a third period, and a fourth period. In the first period, the voltage or current of the AC in the positive direction slowly increases from zero to the peak value. In the second period, the voltage or current of the AC in the positive direction slowly decreases from the peak value to zero. In the third period, the voltage or current of the AC in the negative direction slowly increases from zero to the peak value. In the fourth period, the voltage or current of the AC in the negative direction slowly decreases from the peak value to zero.

In some embodiments, a voltage U of the AC meets the following formula:

$$U=U_m*\mathrm{Sin}(\omega t+\mu) \quad (11);$$

where $U_m$ is the peak value of the AC; ω is an angular frequency of the AC; u is an initial phase; and t is the time.

The minimum repetition cycle meets:

$$T=2\pi/\omega \quad (12),$$

where T is a duration of the minimum repetition cycle.

In some embodiments, the minimum repetition cycle includes a first power-on period when a forward connection current flows, and a second power-on period when a reverse connection current flows.

In some embodiments, an AC conforming to a triangular wave curve is provided, where a voltage U of the AC meets the following formula:

$$U=kt+b \quad (13);$$

where k is a slope of the curve of the triangular wave; b is a constant; and t indicates time.

In some embodiments, $U_m$, ω, and μ are regulable.

An electrical heating device includes a power supply circuit, an electrical heating module and a control module. The electrical heating module and the control module are electrically connected to the power supply circuit. The control module is configured to perform the control methods for heating the electrical heating module provided in the embodiments of this disclosure.

According to the electrical heating device provided herein, by using the control method for heating the electrical heating module provided in this embodiment, the heat energy can be distributed evenly on the electrical heating module, preventing the electrical heating module from being burned due to excessively high local temperature, and prolonging the service life of the automizer. The electric field presents the positive direction and the negative direction on the electrical heating module alternately, which can effectively prevent foreign matters such as carbides from accumulating on the surface of the electrical heating module, maintaining the cleaning of the electrical heating module, so as to ensure the pure taste of the atomized e-cigarette oil or the baked non-combustible tobacco.

A method for driving the power supply circuit is provided in an embodiment, which includes the following steps.

The power supply circuit is provided, which includes a microprocessor, a voltage modulation module, and a heating module.

The microprocessor is configured to control the voltage modulation module.

The voltage modulation module is configured to control the voltage of the DC power supply to obtain a first target voltage and a first target current based on a first preset parameter set sent by the microprocessor during a first time interval of the first repetition cycle in the first preset time interval, and obtain the second target voltage and the second target current based on the second preset parameter set sent by the microprocessor during a second time interval of the first repetition cycle. The first repetition cycle includes at least one first time interval and at least one second time interval.

The electrical heating module is configured to heat according to the first target voltage, the first target current, the second target voltage, and the second target current.

In this embodiment, the first preset parameter set includes a variation range of the first voltage and a frequency variation of the first voltage. The second preset parameter set includes a variation range of the second voltage and a frequency variation of the second voltage.

In this embodiment, the voltage modulation module includes a power conversion circuit configured to modulate the voltage of the DC power supply based on a modulation signal sent by the microprocessor, and output a boost voltage, a buck voltage, or a pass-through voltage according to the modulation signal.

In this embodiment, the power conversion circuit includes a boost control circuit and a buck circuit.

The boost control circuit is configured to modulate the voltage of the DC power supply to obtain the first target voltage and the first target current based on the first preset parameter set sent by the microprocessor during the first time interval of the first repetition cycle in the first time range. The first target voltage is higher than the voltage of the DC power supply.

The buck circuit is configured to modulate the first target voltage to obtain the second target voltage and the second target current based on the second preset parameter set sent by the microprocessor during the second time interval of the first repetition cycle in the second time range. The second target voltage is lower than the first target voltage.

Optionally, the first repetition period also includes a third time interval, or a third time interval, . . . , and the $N^{th}$ time interval, where N≥3, and N represents an ordinal number.

The boost control circuit modulates the voltage of the DC power supply to obtain a third target voltage and a third target current during the third time interval of the first repetition cycle in the first preset time interval according to the third preset parameter set sent by the microprocessor.

Or, the boost control circuit and the buck circuit alternately modulate the voltage of the DC power supply to obtain the third target voltage, . . . , and the $N^{th}$ target voltage and the third target current, . . . , and the $N^{th}$ target current in the third time interval, . . . , and the $N^{th}$ duration of the first repetition of the first preset time interval according to the third preset parameter set, . . . , and the $N^{th}$ preset parameter set sent by the microprocessor. The third target voltage, . . . , and the $N^{th}$ target voltage are all higher than the voltage of the DC power supply. However, the third target voltage, . . . , and the $N^{th}$ target voltage are different from each other based on different working modes of the boost voltage circuit and the buck voltage circuit. The first repetition cycle includes at least one third time interval, or at least one third time interval, . . . , and the $N^{th}$ time interval.

The electrical heating module is further configured to heat according to the third target voltage and the third target current, or the third target voltage, . . . , and the $N^{th}$ target voltage and the third target current, . . . , and the $N^{th}$ target current.

In this embodiment, the third preset parameter set includes a variation change of the third voltage and a frequency variation of the third voltage. The $N^{th}$ preset parameter set includes a variation change of the $N^{th}$ voltage and a frequency variation of the $N^{th}$ voltage.

In this embodiment, the boost control circuit modulates the voltage of the DC power supply to obtain the $A^{th}$ target voltage and the $A^{th}$ target current according to the $A^{th}$ preset parameter set sent by the microprocessor in $A^{th}$ time interval of the second repetition cycle in the second time range.

The buck circuit modulates the $B^{th}$ target voltage to obtain the $B^{th}$ target voltage and the B-th target current according to the $B^{th}$ preset parameter set sent by the microprocessor in the $B^{th}$ time interval of the second repetition cycle in the second time range. The $B^{th}$ target voltage is lower than the $A^{th}$ target voltage. The second repetition cycle includes at least one $A^{th}$ time interval and at least one $B^{th}$ time interval.

The electrical heating module is further configured to heat according to the $A^{th}$ target voltage, the $A^{th}$ target current, the $B^{th}$ target voltage and the $B^{th}$ target current.

In this embodiment, the $A^{th}$ preset parameter set includes the $A^{th}$ voltage variation amplitude and the $A^{th}$ voltage variation frequency. The $B^{th}$ preset parameter set includes the $B^{th}$ voltage variation amplitude and the $B^{th}$ voltage variation frequency.

In this embodiment, the second repetition cycle also includes a $C^{th}$ time interval, or the $C^{th}$ time interval, . . . , and the $M^{th}$ time interval, where M≥3, and M represents an ordinal number.

The boost control circuit modulates the voltage of the DC power supply to obtain the $C^{th}$ target voltage and the $C^{th}$ target current according to the $C^{th}$ preset parameter set sent by the microprocessor in the $C^{th}$ time interval of the second repetition cycle in the second preset time interval.

Or, the boost control circuit and the buck circuit alternately modulate the voltage of the DC power supply to obtain the $C^{th}$ target voltage, . . . , and the $M^{th}$ target voltage and the $C^{th}$ target current, . . . , and the $M^{th}$ target current based on the $C^{th}$ preset parameter set, . . . , and the $M^{th}$ preset parameter set sent by the microprocessor in the $C^{th}$ time interval, . . . , and the $M^{th}$ time interval of the second repetition cycle of the second time interval. The $C^{th}$ target voltage, . . . , and the $M^{th}$ target voltage are all higher than the voltage of the DC power supply, and the $C^{th}$ target voltage, . . . , and the $M^{th}$ target voltage are different from each other according to the different working modes of the boost control circuit and the buck circuit. The second repetition cycle includes at least one $C^{th}$ time interval, or at least one $C^{th}$ time interval, . . . , and at least one $M^{th}$ time interval.

The electrical heating module is further configured to heat according to the $C^{th}$ target voltage and the $C^{th}$ target current, or the $C^{th}$ target voltage, . . . , and the $M^{th}$ target voltage and the $C^{th}$ target current, . . . , and the $M^{th}$ target current.

In this embodiment, the $C^{th}$ preset parameter set includes a variation range of the $C^{th}$ voltage and a frequency variation of the $C^{th}$ voltage. The $M^{th}$ preset parameter set includes a variation range of the $M^{th}$ voltage and a frequency variation of the $M^{th}$ voltage.

In some embodiments, the boost control circuit and the buck circuit work alternately in at least one first preset time interval and at least one second preset time interval according to an order of the preset time intervals within the preset alternating time interval.

The boost control circuit and the buck circuit work alternately in at least one first time range and at least one second time range according to an order of the preset time intervals within the preset alternating sub-period.

Optionally, the boost control circuit and the buck circuit work alternately in at least one first preset time interval, at least one second preset time interval, at least one third preset time interval, . . . , and at least one $N^{th}$ preset time interval according to an order of the preset time intervals within the preset alternating sub-period.

In some embodiments, the boost control circuit and the buck circuit work alternately in at least one $A^{th}$ preset time interval and at least one $B^{th}$ preset time interval according to an order of the preset time intervals within the preset alternating sub-period.

In some embodiments, the boost control circuit and the buck circuit work alternately at least one $A^{th}$ preset time interval, at least one $B^{th}$ preset time interval and at least one $C^{th}$ preset time interval according to an order of the preset time intervals within the preset alternating sub-period.

In some embodiments, the boost control circuit and the buck circuit work alternately at least one $A^{th}$ preset time interval, at least one $B^{th}$ preset time interval, at least one $C^{th}$ preset time interval, . . . , and at least one $M^{th}$ preset time interval according to an order of the preset time intervals within the preset alternating sub-period.

An electronic atomization device is provided in an embodiment, which performs the method for driving the power supply circuit provided in the above-mentioned embodiments.

Referring to the above technical solutions, the embodiment of the application has the following advantages.

The microprocessor controls the voltage modulation module. The voltage modulation module controls the voltage of the DC power supply to obtain the first target voltage and the first target current according to the first preset parameter set sent by the microprocessor in the first time interval of the first repetition cycle of the first time interval, and obtain the second target voltage and the second target current according to the second preset parameter set sent by the microprocessor in the second time interval of the first repetition cycle. The first repetition cycle includes at least one first time interval and at least one second time interval. Then the electrical heating module is configured to heat according to the first target voltage, the first target current, the second target voltage, and the second target current. In conclusion, the first target voltage, the first target current, the second target voltage, and the second target current applied to the electrical heating module are different from each other, so that the electrical heating module provided with the electrical heating module is allowed to be heated based on the variable output voltage and output current, thereby limiting the temperature increase of the electrical heating module after energization, reducing the local carbide deposition in the electrical heating module. Moreover, the variable voltage enables the temperature of the electrical heating module to change with the voltage, such that the electrical heating module is not always at a high temperature, making the electrical heating module heated evenly, and prolonging the service life of the electrical heating module. The method provided herein effectively improves the restoration degree of the e-cigarette oil and the tobacco paste, and the taste of the baked non-combustible tobacco and the atomized aerosol.

A power supply circuit and an electric terminal thereof are provided herein. By arranging electronic components in a separately integrated manner, the space occupied by the electronic components in small-scale electronic terminals is reduced, which can decrease the production costs and improve the practicality of the power supply circuit provided with separately packaged structures.

In the first aspect of this disclosure, a power supply circuit is provided herein. The power supply circuit includes a microprocessor, a voltage modulation module, a driving module, a forward and reverse connection current switch module, and a heating module.

Based on the discrete integration of modules, the power supply circuit integrates and packages the electronic components of the microprocessor, the voltage modulation module, the forward and reverse connection current switch module, the driving module, and the electrical heating module on a circuit board according to the modules thereto.

In this embodiment, the microprocessor is configured to control the voltage modulation module, the driving module, and the forward and reverse connection current switch module.

The voltage modulation module is configured to modulate the voltage of the power supply into the first target voltage and the second target voltage. The second target voltage is coupled to the driving module, and the first target voltage is configured to control the on and off of the forward and reverse connection current switch module.

The driving module is configured to couple the first target voltage to the forward and reverse connection current switch module, so as to drive the forward and reverse connection current switch module to work.

The forward and reverse connection current switch module is configured to generate a forward connection current and a reverse connection current according to the second target voltage, and couple the forward connection current and the reverse connection current to the electrical heating module in the different time intervals of the same signal time interval of the second target voltage.

The electrical heating module is configured to alternately heat based on the forward connection current and the reverse connection current.

In this embodiment, the forward and reverse connection current switch module includes a first current switch sub-module and a second current switch sub-module.

The different time intervals include a first time interval and a second time interval.

The first current switch sub-module is configured to be turned on in the first time interval, generate the forward connection current according to the second target voltage, and couple the forward connection current to the electrical heating module. The first time interval is the first time interval in the same voltage signal time interval of the second target voltage.

The second current switch sub-module is configured to be turned on in the second time interval, generate the reverse connection current according to the second target voltage, and couple the reverse connection current to the electrical heating module. The second time interval is the second time interval in the same voltage signal time interval of the second target voltage. The sum of the first time interval and the second time interval is not larger to a duration threshold of the same voltage signal time interval.

In this embodiment, the different time intervals further include a third time interval, or the third time interval, . . . , and the $N^{th}$ time interval, where N represents an ordinal number.

In this embodiment, the first time interval and the second time interval are equal or unequal.

In this embodiment, the current amplitude of the forward connection current in the first time interval and the current amplitude of the reverse connection current in the second time interval are equal or unequal.

In this embodiment, the waveform of the forward connection current in the first time interval and the waveform of the reverse connection current in the second time interval are the same or different.

In this embodiment, the first current switch sub-module includes a first transistor and a second transistor.

The second terminal of the first transistor is connected to one end of the electrical heating module.

The first terminal of the second transistor is grounded, and the second terminal of the second transistor is connected to the other end of the electrical heating module.

The second current switch sub-module includes a third transistor and a fourth transistor.

The second terminal of the third transistor is connected to the other end of the electrical heating module.

The first terminal of the fourth transistor is grounded, and the second terminal of the fourth transistor is connected to one end of the electrical heating module.

In an embodiment, the first transistor and the third transistor are PMOS transistors, while the second transistor and the fourth transistor are NMOS transistors.

In an embodiment, the first transistor and the third transistor are NMOS transistors, while the second transistor and the fourth transistor are PMOS transistors.

In an embodiment, the first transistor and the third transistor are NPN triodes, while the second transistor and the fourth transistor are PNP triodes, or the second transistor and the fourth transistor are NPN triodes.

In an embodiment, the number of transistors in the first current switch sub-module is equal to or unequal to the number of transistors in the second current switch sub-module.

In an embodiment, both the first current switch sub-module and the second current switch sub-module contain more than three transistors.

In an embodiment, one sub-module of the first current switch sub-module and the second current switch sub-module contains more than three transistors, and the other sub-module of the first current switch sub-module and the second current switch sub-module contains less than three transistors.

In an embodiment, the driving module includes a first driving element and a second driving element.

The first terminal of the first driving element is connected to the third terminal of the first transistor. The second terminal of the first driving element is grounded, and the third terminal of the driving element is connected to the microprocessor.

The first terminal of the second driving element is connected to the third terminal of the third transistor, the second terminal of the second driving element is grounded, and the third terminal of the second driving element is connected to microprocessor.

In this embodiment, the first driving element and the second driving element are NPN triodes.

In an embodiment, the first driving element and the second driving element are both PNP triodes.

In an embodiment, the first driving element and the second driving element are both N-type metal oxide semiconductors.

In an embodiment, both the first driving element and the second driving element are PMOSs.

In an embodiment, the driving module includes more than three driving elements.

In an embodiment, the voltage modulation module includes a voltage boost control circuit and a power conversion circuit.

The voltage boost control circuit is configured to boost the voltage of the power supply to obtain the first target voltage, and transmit the first target voltage to the first current switch sub-module and the second current switch sub-module, respectively. One end of the voltage boost control circuit is connected to the third terminal of the second transistor and the third terminal of the fourth transistor respectively, and the other end of the voltage boost control circuit is connected to a power supply.

The power conversion circuit is configured to modulate the voltage of the power supply to the second target voltage. One end of the power conversion circuit is respectively connected to the first terminal of the first transistor and the first terminal of the third transistor, and the other end of the power conversion circuit is connected to the power supply.

In the second aspect of this disclosure, an electronic terminal is provided. The electronic terminal includes the power supply circuit provided in the above-mentioned embodiments of the first aspect.

As shown from the above-mentioned technical solutions, the power supply circuit provided with discrete packaging structures provided herein includes a microprocessor, a voltage modulation module, a driving module, a forward and reverse connection current switch module, and a heating module. By packaging each module of the power supply circuit separately, the electronic components of the microprocessor, the voltage modulation module, the forward and reverse connection current switch module, the driving module, and the electrical heating module can be separately integrated on the circuit board according to the modules thereof. In conclusion, compared with the packaging of each electronic component separately, the power supply circuit provided herein reduces the occupied area of the electronic components on the electronic terminal and the circuit board, lowering the production cost and improving the practicability of the power supply circuit with the discrete package structure.

A method for driving the power supply circuit and an electronic heating device thereof are provided herein. By using the method, the power supply control circuit can modulate a voltage of a DC power supply into a first target voltage and a second target voltage which are alternately changed, to heat the electrical heating module, and suppress the temperature rise of the electrical heating module, enabling the electrical heating module to be uniformly heated, prolonging the service life of the electrical heating module, and improving the use performance of the electrical heating module.

A method for driving the power supply circuit is provided in an embodiment, which includes the following steps.

A power supply circuit is provided, which includes a microprocessor, a voltage modulation module and a heating module.

The microprocessor is configured to control the voltage modulation module.

In this embodiment, the power conversion circuit includes a boost control circuit and a buck circuit.

The boost control circuit is configured to modulate the voltage of the DC power supply to obtain the first target voltage and the first target current according to the first preset parameter set sent by the microprocessor in the first time interval of the first repetition cycle in the first preset time interval. The first target voltage is higher than the voltage of the DC power supply. The voltage modulation module is configured to modulate the voltage of the DC power supply to obtain the first target voltage and the first target current based on the first preset parameter set sent by the microprocessor in the first time interval of the first repetition cycle of the first preset time interval, and obtain the second target voltage and the second target current based on the second preset parameter set sent by the microprocessor in the second time interval of the first repetition cycle in the first time range. The first repetition cycle includes at least one first preset time interval and at least one second time interval.

The electrical heating module is configured to heat according to the first target voltage, the first target current, the second target voltage and the second target current.

In this embodiment, the first preset parameter set includes a variation range of the first voltage and a frequency range of the first voltage variation. The second preset parameter set includes a variation range of the second voltage and a frequency range of the second voltage variation.

In this embodiment, the voltage modulation module includes a power conversion circuit. The power conversion circuit modulates the voltage of the DC power supply according to a modulation signal sent by the microprocessor, and outputs a boost voltage, a buck voltage, and a pass-through voltage according to the modulation signal.

The buck circuit is configured to modulate the first target voltage to obtain the second target voltage and the second target current based on the second preset parameter set sent by the microprocessor in the second time interval of the first repetition cycle in the second time range. The second target voltage is lower than the first target voltage.

In this embodiment, the first repetition cycle further includes a third time interval, or a third time interval, . . . , and an $N^{th}$ time interval, where N≥3, and N represents an ordinal number.

The boost control circuit is configured to modulate the voltage of the DC power supply to obtain the third target voltage and the third target current according to the third preset parameter set sent by the microprocessor in the third time interval of the first repetition cycle in the first preset time interval.

Or, the boost control circuit and the buck circuit alternately modulate the voltage of the DC power supply to obtain the third target voltage, . . . , and the N-th target voltage and the third target current, . . . , and the $N^{th}$ target current according to the third preset parameter set, . . . , and $N^{th}$ preset parameter set sent by the microprocessor in the third duration, . . . , and the $N^{th}$ duration of the first repetition cycle in the first preset time interval. The third target voltage, . . . , and the $N^{th}$ target voltage are higher than the voltage of the DC power supply, and are different from each other according to the different working modes of the boost control circuit and the buck circuit. The first repetition cycle includes at least one third time interval, or at least one third time interval, . . . , and at least one of the $N^{th}$ time interval.

The electrical heating module is further configured to perform heating based on the third target voltage and the third target current, or the third target voltage, . . . , and the $N^{th}$ target voltage, and the third target current, . . . , and the $N^{th}$ target current.

In this embodiment, the third preset parameter set includes a variation range of the third voltage and a frequency range of the third voltage variation. The $N^{th}$ preset parameter set includes a variation range of the $N^{th}$ voltage and a frequency range of the $N^{th}$ voltage variation.

In this embodiment, the boost control circuit modulates the voltage of the DC power supply to obtain the $A^{th}$ target voltage and the $A^{th}$ target current according to the $A^{th}$ preset parameter set sent by the microprocessor in the $A^{th}$ time interval of the second repetition cycle in the second preset time interval.

The buck circuit modulates the $B^{th}$ target voltage to obtain the B-th target voltage and the $B^{th}$ target current according to the $B^{th}$ preset parameter set sent by the microprocessor in the $B^{th}$ time interval of the second repetition cycle in the second time range. The $B^{th}$ target voltage is lower than the $A^{th}$ target voltage. The second repetition cycle includes at least one $A^{th}$ time interval and at least one $B^{th}$ time interval.

The electrical heating module is further configured to perform heating based on the $A^{th}$ target voltage, the $A^{th}$ target current, the $B^{th}$ target voltage and the $B^{th}$ target current.

In an embodiment, the $A^{th}$ preset parameter set includes a variation range of the $A^{th}$ voltage and a frequency range of the $A^{th}$ voltage variation, and the $B^{th}$ preset parameter set includes a variation range of the $B^{th}$ voltage and a frequency range of the $B^{th}$ voltage variation.

In an embodiment, the second repetition cycle further includes the $C^{th}$ time interval, or the $C^{th}$ time interval, . . . , and the $M^{th}$ time interval, where M≥3, and M represents an ordinal number.

The boost control circuit modulates the voltage of the DC power supply to obtain the $C^{th}$ target voltage and the $C^{th}$ target current according to the $C^{th}$ preset parameter set sent by the microprocessor in the $C^{th}$ time interval of the second repetition cycle in the second preset time interval.

Or, the boost control circuit and the buck circuit alternately modulate the voltage of the DC power supply to obtain the $C^{th}$ target voltage, . . . , and the $M^{th}$ target voltage, and the $C^{th}$ target current, . . . , and the $M^{th}$ target current based on the $C^{th}$ preset parameter set to the $M^{th}$ preset parameter set sent by the microprocessor in the $C^{th}$ time interval, . . . , and the $M^{th}$ time interval of the second repetition cycle of the second time interval. The $C^{th}$ target voltage, . . . , and the $M^{th}$ target voltage are all higher than the voltage of the DC power supply, and are different from each other according to the different working modes of the boost control circuit and the buck circuit. The second repetition cycle includes at least one $C^{th}$ time interval, or at least one $C^{th}$ time interval, . . . , and at least one $M^{th}$ time interval.

The electrical heating module is further configured to be heated according to the $C^{th}$ target voltage and the $C^{th}$ target current, or the $C^{th}$ target voltage, . . . , and the $M^{th}$ target voltage and the $C^{th}$ target current, . . . , and the $M^{th}$ target current.

In an embodiment, the $C^{th}$ preset parameter set includes a variation range of the $C^{th}$ voltage and a frequency range of the $C^{th}$ voltage variation, and the $M^{th}$ preset parameter set includes a variation range of the $M^{th}$ voltage and a frequency range of the $M^{th}$ voltage variation.

In an embodiment, the boost control circuit and the buck circuit work alternately in at least one first time interval and at least one second time interval according to an order of the preset time intervals within the preset alternating time interval.

In an embodiment, the boost control circuit and the buck circuit work alternately in at least one first time interval and at least one second time interval according to an order of the preset time intervals within the preset alternating sub-period.

In an embodiment, the boost control circuit and the buck circuit work alternately in at least one first time interval, at least one second time interval, and at least one third time interval according to an order of the preset time intervals within the preset alternating sub-period.

In an embodiment, the boost control circuit and the buck circuit work alternately in at least one first time interval, at least one second time interval, at least one third time interval, . . . , and at least one $N^{th}$ time interval according to an order of the preset time intervals within the preset alternating sub-period.

In an embodiment, the boost control circuit and the buck circuit work alternately in at least one $A^{th}$ time interval and at least one $B^{th}$ time interval according to an order of the preset time intervals within the preset alternating sub-period.

In some embodiments, the boost control circuit and the buck circuit work alternately at least one $A^{th}$ preset time interval, at least one $B^{th}$ preset time interval and at least one $C^{th}$ preset time interval according to an order of the preset time intervals within the preset alternating sub-period.

In an embodiment, the boost control circuit and the buck circuit work alternately in at least one $A^{th}$ time interval, at least one $B^{th}$ time interval, and at least one $C^{th}$ time interval, . . . , and at least one $M^{th}$ time interval according to an order of the preset time intervals within the preset alternating sub-period.

An electronic atomization device is provided in an embodiment. The electronic atomization device is configured to carry out the method for driving the power supply circuit in the above-mentioned embodiments.

As shown from the above technical solutions, this disclosure has the following advantages.

The microprocessor is configured to control the voltage modulation module. The voltage modulation module is configured to control the voltage of the DC power supply to obtain the first target voltage and the first target current according to the first preset parameter set sent by the microprocessor in the first time interval of the first repetition cycle of the first time interval, and obtain the second target voltage and the second target current according to the second preset parameter set sent by the microprocessor in the second time interval of the first repetition cycle in the first time range. The first repetition cycle includes at least one first time interval and at least one second time interval. Then the electrical heating module is configured to heat according to the first target voltage, the first target current, the second target voltage, and the second target current. In conclusion, the first target voltage, the first target current, the second target voltage, and the second target current output to the electrical heating module are different from each other, such that the electrical heating module provided with the electrical heating module is allowed to be heated based on the continuous variable output voltage and output current, thereby limiting the temperature increase of the electrical heating module after energization, reducing the local carbide deposition in the electrical heating module. Moreover, the variable voltage enables the temperature of the electrical heating module to change with the voltage such that the high temperature is not maintained consistently, and thus making the electrical heating module heated evenly, and prolonging the service life of the electrical heating module. The method provided herein effectively improves the restoration degree of the e-cigarette oil and the tobacco paste, and the taste of the baked non-combustible tobacco and the atomized aerosol.

In this embodiment, a power supply circuit and a method for driving the power supply circuit and the electronic cigarette are provided, which can achieve the uniform heating of the electrical heating module, enhance the service performance of the small-scale electronic terminals, and prolongs the service life of the electrical heating device.

Provided herein is a power supply circuit, which includes a microprocessor, a voltage modulation module, a forward and reverse connection current generation module, and an electrical heating module.

The microprocessor is configured to control the voltage modulation module and the forward and reverse connection current generation module.

The voltage modulation module is configured to regulate the voltage of the power supply to a first target voltage and a second target voltage, and couple the second target voltage to the forward and reverse connection current generation module. The first target voltage is configured to control on and off of the forward and reverse connection current generation module.

The forward and reverse connection current generation module is configured to generate a forward connection current and a reverse connection current according to the second target voltage, and couple the forward connection current and the reverse connection current to the electrical heating module at different time intervals within the same signal time interval of the second target voltage.

The electrical heating module is configured to generate a working current to heat. The working current includes the forward connection current and the reverse connection current.

In this embodiment, the forward and reverse connection current generation module includes a first switch control module and a second switch control module.

The first switch control module is configured to be switched on in a first time interval, generate the forward connection current according to the second target voltage, and couple the forward connection current to the electrical heating module. The first time interval is a first duration of the second target voltage preset in the same voltage signal time interval.

The second switch control module is configured to be switched on in a second time interval, generate the reverse connection current according to the second target voltage, and couple the reverse connection current to the electrical heating module. The second time interval is a second duration of the second target voltage preset in the same voltage signal time interval, and a sum of the first time interval and the second time interval is not larger than a duration threshold of the same voltage signal time interval.

In this embodiment, the voltage of the power supply includes a voltage of a first power supply and a voltage of a second power supply. The negative electrode of the first power supply and the negative electrode of the second power supply are connected and both grounded. Both the voltage of the first power supply and the voltage of the second power supply are connected to the voltage modulation module.

In this embodiment, the voltage modulation module includes a first boost control circuit, a first power conversion circuit, a second boost control circuit and a second power conversion circuit.

The first boost control circuit is configured to boost the voltage of the first power supply to obtain the first target voltage, and transmit the first target voltage to the first switch control module. One end of the first boost control circuit is connected to the first switch control module, and the other end of the first boost control circuit is connected to a first power supply.

The first power conversion circuit is configured to modulate the voltage of the first power supply to the second target voltage. One end of the first power conversion circuit is connected to the first switch control module, and the other end of the first power conversion circuit is connected to the first power supply.

The second boost control circuit is configured to boost the voltage of the second power supply to the first target voltage, and transmit the first target voltage to the second switch control module. One end of the second boost control circuit is connected to the second switch control module, and the other end of the second boost control circuit is connected to a second power supply.

The second power conversion circuit is configured to modulate the voltage of the second power supply to the second target voltage. One end of the second power conversion circuit is connected to the second switch control module, and the other end of the second power conversion circuit is connected to the second power supply.

In this embodiment, the first switch control module includes a first power supply and a first transistor.

The first power supply is configured to provide a voltage of the first power supply to the first boost control circuit within the first time interval.

The first terminal of the first transistor is grounded, the second terminal of the first transistor is connected to one end of the electrical heating module, and the third terminal of the first transistor is connected to the one end of the first boost control circuit.

In this embodiment, the second switch control module includes a second power supply and a second transistor.

The second power supply is configured to provide a voltage of the second power supply to the second boost control circuit within the second time interval.

The first terminal of the second transistor is grounded, the second terminal of the second transistor is connected to the other end of the electrical heating module, and the third terminal of the second transistor is connected to the one end of the second boost control circuit.

In this embodiment, the electrical heating module is a heating resistor.

In this embodiment, a method for driving the power supply circuit is provided herein. The method is performed as follows.

Provided herein is a power supply circuit, which includes a microprocessor, a voltage modulation module, a forward and reverse connection current generation module, and a heating module.

The microprocessor is configured to control the voltage modulation module and the forward and reverse connection current generation module.

The voltage modulation module is configured to regulate the voltage of the power supply to a first target voltage and a second target voltage. The first target voltage is configured to control on and off of the forward and reverse connection current generation module.

The forward and reverse connection current generation module is configured to generate a forward connection current and a reverse connection current according to the second target voltage.

The electrical heating module is configured to generate a working current to heat. The working current includes the forward connection current and the reverse connection current.

The driving method of the power supply control circuit includes the following steps.

The voltage modulation module is configured to couple the second target voltage to the forward and reverse connection current generation module.

The forward and reverse connection current generation module is configured to couple the forward connection current and the reverse connection current to the electrical heating module in the different time intervals of the same signal time interval of the second target voltage.

In an embodiment, the forward and reverse connection current generation module includes a first switch module and a second switch module.

In the driving method of the power supply control circuit, the first switch control module is switched on in a first time interval, generates the forward connection current according to the second target voltage, and couples the forward connection current to the heating module. The first time interval is a first duration of the second target voltage preset in the same voltage signal time interval.

The second switch control module is switched on in a second time interval, generates the reverse connection current according to the second target voltage, and couples the reverse connection current to the electrical heating module. The second time interval is a second duration of the second target voltage preset in the same voltage signal time interval, and a sum of the first time interval and the second time interval is not larger than a duration threshold of the same voltage signal time interval.

In an embodiment, the voltage of the power supply includes a voltage of the first power supply and a voltage of the second power supply. The negative electrodes of the first power supply and the second power supply are connected and both grounded. Both the positive electrodes of the first power supply and the second power supply are connected to the voltage modulation module. The microprocessor is connected to any one of the positive electrodes of the first power supply voltage and the second power supply voltage.

In the method for driving the power supply circuit, the voltage modulation module is connected to the voltage of the first power supply by the microprocessor in the first time interval.

The voltage modulation module is connected to the voltage of the second power supply by the microprocessor in the second time interval.

The voltage modulation module includes a first boost control circuit, a first power conversion circuit, a second boost control circuit, and a second power conversion circuit.

The first boost control circuit is configured to boost the voltage of the first power supply to obtain the first target voltage. One end of the first boost control circuit is connected to the first switch control module, and the other end of the first boost control circuit is connected to the first power supply.

The first power conversion circuit is configured to modulate the voltage of the first power supply to the second target voltage. One end of the first power conversion circuit is connected to the first switch control module, and the other end of the first power conversion circuit is connected to the first power supply.

The second boost control circuit is configured to boost the voltage of the second power supply to the first target voltage. One end of the second boost control circuit is connected to the second switch control module, and the other end of the second boost control circuit is connected to the second power supply.

The second power conversion circuit is configured to modulate the voltage of the second power supply to the second target voltage. One end of the second power conversion circuit is connected to the second switch control module, and the other end of the second power conversion circuit is connected to the second power supply.

In this embodiment, the first boost control circuit transmits the first target voltage to the first switch control module, and the first power conversion circuit transmits the second target voltage to the first switch control module during the first time interval.

The second boost control circuit transmits the first target voltage to the second switch control module, and the second power conversion circuit transmits the second target voltage to the second switch control module during the second time interval.

Optionally, the first switch control module includes a first power supply and a first transistor.

The first power supply is configured to provide the voltage of the first power supply to the first boost control circuit within the first time interval.

The first terminal of the first transistor is grounded, the second terminal of the first transistor is connected to one end of the electrical heating module, and the third terminal of the first transistor is connected to the one end of the first boost control circuit.

In this embodiment, the first transistor is turned on during the first time interval. The forward connection current is coupled to the electrical heating module, and the second transistor is turned off at the same time.

In this embodiment, the second switch control module includes a second power supply and a second transistor.

The second power supply is configured to provide the voltage of the second power supply to the second boost control circuit within the second time interval.

The first terminal of the second transistor is grounded, the second terminal of the second transistor is connected to the other end of the electrical heating module, and the third terminal of the second transistor is connected to the one end of the second boost control circuit.

In this embodiment, the second transistor is turned on during the second time interval. The reverse connection current is coupled to the electrical heating module, and the first transistor is turned off at the same time.

An e-cigarette is provided in an embodiment, which includes the power supply circuit and the driving method thereof provided herein.

As shown in the above technical solutions, this embodiment has the following advantages.

The microprocessor controls the voltage modulation module and the forward and reverse connection current generation module. The voltage modulation module regulates the voltage of the power supply to the first target voltage and the second target voltage, and couples the second target voltage to the forward and reverse connection current generation module. The forward and reverse connection current generation module generates the forward connection current and the reverse connection current according to the second target voltage, and couples the forward connection current and the reverse connection current to the electrical heating module in the different time intervals of the same signal time interval of the second target voltage. Thus, the electrical heating module can alternately generate the forward connection current and the reverse connection current to heat, so that the electrical heating device can be heated evenly, thereby improving the service performance of the small-scale electronic terminals and prolonging the service life of the electrical heating device.

What is claimed is:

1. A power supply control circuit for an electrical heating module of a personal vaping device, comprising:

- a current input terminal configured to be connected to a direct current (DC) power supply;
- a current output terminal separated from the current input terminal and configured to be connected to the electrical heating module; and
- a power supply control module arranged between the current input terminal and the current output terminal,
- wherein the power supply control module is configured to control connection and disconnection of the current output terminal with the electrical heating module, and to convert a DC from the DC power supply into a supply current having a periodic variation in at least one of a direction, an instantaneous value, or an on-state time,
- wherein the power supply control module comprises a voltage modulation module, a microprocessor, and a forward and reverse connection current generation module,
- wherein the microprocessor is configured to control the voltage modulation module and the forward and reverse connection current generation module; and
- wherein the voltage modulation module is configured to regulate a voltage of the DC power supply to a first target voltage and a second target voltage, and couple the second target voltage to the forward and reverse connection current generation module, wherein the first target voltage is configured to control on and off of the forward and reverse connection current generation module.

2. The power supply control circuit according to claim 1, wherein the power supply control module converts the DC from the DC power supply, the power supply control module is configured to:

- control the periodic variation of the supply current at a frequency within a range of 300-1000 Hz in a cleaning state, or within a range of 2-200 Hz in a vaping state.

3. The power supply control circuit according to claim 1,

- wherein the microprocessor is configured to provide an actuation signal to the voltage modulation module and output the actuation signal according to a plurality of preset parameters including a variation range of the instantaneous value and a frequency of the periodic variation,
- wherein the voltage modulation module is configured to convert the DC flowing from the current input terminal into the supply current by modulating the actuation signal, and to establish a circuit to connect the electrical heating module through the current output terminal,
- wherein the voltage modulation module comprises a power conversion circuit,
- wherein the power conversion circuit is configured to modulate a voltage of the DC power supply according to a modulation signal sent by the microprocessor, and to output a boost voltage, a buck voltage, or a pass-through voltage according to the modulation signal.

4. The power supply control circuit according to claim 3, wherein the power conversion circuit comprises a full-bridge circuit including an energy storage inductor and a plurality of switch components, wherein the microprocessor is configured to control the plurality of switch components such that the full-bridge circuit operates as a boost control circuit during a first time interval and operates as a buck circuit during a second time interval different from the first time interval; or

- the power conversion circuit comprises a boost control circuit and a buck circuit independent of each other.

5. The power supply control circuit according to claim 1, wherein in a duty cycle, the on-state time of the supply current varies.

6. The power supply control circuit according to claim 3, wherein the power supply control module is configured to continuously maintain the supply current in an on state,

- wherein the power supply control module is configured to reverse a direction of the supply current at least once in a duty cycle to form an AC,
- wherein a working duration of the AC is less than or equal to a time interval threshold, and
- wherein the power supply control module is configured to maintain an output energy of the supply current at a preset constant level during each duty cycle.

7. The power supply control circuit according to claim 1, wherein the forward and reverse connection current generation module comprises a first switch control module and a second switch control module, wherein the first switch control module is configured to be switched on during a first time interval, generate a forward connection current according to the second target voltage, and couple the forward connection current to the electrical heating module; and the second switch control module is configured to be switched on during a second time interval, generate a reverse connection current according to the second target voltage, and couple the reverse connection current to the electrical heating module, wherein the first time interval and the second time interval are different time intervals within a duty cycle of the second target voltage, and a sum of the first time interval and the second time interval is not larger than a duration threshold of the duty cycle of the second target voltage.

8. The power supply control circuit according to claim 3, wherein the power conversion circuit comprises a boost control circuit and a buck circuit;

the boost control circuit is configured to modulate the voltage of the DC power supply to obtain a first target voltage and a first target current according to a first preset parameter set sent by the microprocessor in a first time range, wherein the first target voltage is higher than the voltage of the DC power supply; and the buck circuit is configured to modulate the first target voltage to obtain a second target voltage and a second target current according to a second preset parameter set sent by the microprocessor in a second time range, wherein the second target voltage is lower than the first target voltage.

9. A personal vaping device, comprising:

an electrical heating module that is an atomizer configured to atomize electronic cigarette liquid; and a power supply control circuit configured to supply power to the electrical heating module, wherein the power supply control circuit comprises:

a current input terminal configured to be connected to a direct current (DC) power supply;

a current output terminal separated from the current input terminal and configured to be connected to the electrical heating module; and a power supply control module arranged between the current input terminal and the current output terminal, wherein the power supply control module is configured to control connection and disconnection of the current output terminal with the electrical heating module, and to convert a DC from the DC power supply into a supply current having a periodic variation in at least one of a direction, an instantaneous value, or an on-state time, wherein the power supply control module comprises a voltage modulation module, a microprocessor, and a forward and reverse connection current generation module, wherein the microprocessor is configured to control the voltage modulation module and the forward and reverse connection current generation module; and wherein the voltage modulation module is configured to regulate a voltage of the DC power supply to a first target voltage and a second target voltage, and couple the second target voltage to the forward and reverse connection current generation module, wherein the first target voltage is configured to control on and off of the forward and reverse connection current generation module.

10. The personal vaping device according to claim 9, wherein the power supply control module converts the DC from the DC power supply, the power supply control module is configured to:

control the periodic variation of the supply current at a frequency within a range of 300-1000 Hz in a cleaning state, or within a range of 2-200 Hz in a vaping state.

11. The personal vaping device according to claim 9, wherein the microprocessor is configured to provide an actuation signal to the voltage modulation module and output the actuation signal according to a plurality of preset parameters including a variation range of the instantaneous value and a frequency of the periodic variation, wherein the voltage modulation module is configured to convert the DC flowing from the current input terminal into the supply current by modulating the actuation signal, and to establish a circuit to connect the electrical heating module through the current output terminal, wherein the voltage modulation module comprises a power conversion circuit, wherein the power conversion circuit is configured to modulate a voltage of the DC power supply according to a modulation signal sent by the microprocessor, and to output a boost voltage, a buck voltage, or a pass-through voltage according to the modulation signal.

12. The personal vaping device according to claim 11, wherein the power conversion circuit comprises a full-bridge circuit including an energy storage inductor and a plurality of switch components, wherein the microprocessor is configured to control the plurality of switch components such that the full-bridge circuit operates as a boost control circuit during a first time interval and operates as a buck circuit during a second time interval different from the first time interval; or the power conversion circuit comprises a boost control circuit and a buck circuit independent of each other.

13. The personal vaping device according to claim 9, wherein in a duty cycle, the on-state time of the supply current varies.

14. The personal vaping device according to claim 11, wherein the power supply control module is configured to continuously maintain the supply current in an on state, wherein the power supply control module is configured to reverse a direction of the supply current at least once in a duty cycle to form an AC, wherein a working duration of the AC is less than or equal to a time interval threshold, and wherein the power supply control module is configured to maintain an output energy of the supply current at a preset constant level during each duty cycle.

15. The personal vaping device according to claim 9, wherein the forward and reverse connection current generation module comprises a first switch control module and a second switch control module, wherein the first switch control module is configured to be switched on during a first time interval, generate a forward connection current according to the second target voltage, and couple the forward connection current to the electrical heating module; and the second switch control module is configured to be switched on during a second time interval, generate a reverse connection current according to the second target voltage, and couple the reverse connection current to the electrical heating module, wherein the first time interval and the second time interval are different time intervals within a duty cycle of the second target voltage, and a sum of the first time interval and the second time interval is not larger than a duration threshold of the duty cycle of the second target voltage.

16. The personal vaping device according to claim 11, wherein the power conversion circuit comprises a boost control circuit and a buck circuit;

the boost control circuit is configured to modulate the voltage of the DC power supply to obtain a first target voltage and a first target current according to a first preset parameter set sent by the microprocessor in a first time range, wherein the first target voltage is higher than the voltage of the DC power supply; and the buck circuit is configured to modulate the first target voltage to obtain a second target voltage and a second target current according to a second preset parameter set sent by the microprocessor in a second time range, wherein the second target voltage is lower than the first target voltage.

* * * * *